(12) United States Patent
Truccolo et al.

(10) Patent No.: US 10,448,877 B2
(45) Date of Patent: Oct. 22, 2019

(54) METHODS FOR PREDICTION AND EARLY DETECTION OF NEUROLOGICAL EVENTS

(75) Inventors: Wilson Truccolo, Providence, RI (US); Leigh R. Hochberg, Brookline, MA (US); John P. Donoghue, Providence, RI (US); Sydney S. Cash, Cambridge, MA (US)

(73) Assignees: Brown University, Providence, RI (US); The General Hospital Corporation, Boston, MA (US); The United States Government as Represented by the Department of Veterans Affairs, Washington, DC (US)

( * ) Notice: Subject to any disclaimer, the term of this patent is extended or adjusted under 35 U.S.C. 154(b) by 1070 days.

(21) Appl. No.: 13/991,680

(22) PCT Filed: Dec. 5, 2011

(86) PCT No.: PCT/US2011/063269
§ 371 (c)(1),
(2), (4) Date: Jun. 5, 2013

(87) PCT Pub. No.: WO2012/078503
PCT Pub. Date: Jun. 14, 2012

(65) Prior Publication Data
US 2013/0261490 A1    Oct. 3, 2013

Related U.S. Application Data

(60) Provisional application No. 61/538,358, filed on Sep. 23, 2011, provisional application No. 61/419,863, filed on Dec. 5, 2010.

(51) Int. Cl.
*A61B 5/0476* (2006.01)
*A61B 5/00* (2006.01)
(Continued)

(52) U.S. Cl.
CPC ............ *A61B 5/4094* (2013.01); *A61B 5/048* (2013.01); *A61B 5/04012* (2013.01);
(Continued)

(58) Field of Classification Search
CPC ... A61B 5/04012; A61B 5/048; A61B 5/4094; A61B 5/0482
See application file for complete search history.

(56) References Cited

U.S. PATENT DOCUMENTS 3,826,244 A * 7/1974 Salcman ................ A61B 5/042
29/874
6,658,287 B1  12/2003 Litt et al.
(Continued)

FOREIGN PATENT DOCUMENTS

WO    WO 2010048613 A2 *  4/2010   ........... A61B 5/0478

OTHER PUBLICATIONS

Shlens et al. The structure of multi-neuron firing patterns in primate retina. J. Neurosci. 2006; 26, 8254-8266.
(Continued)

*Primary Examiner* — Meredith Weare
(74) *Attorney, Agent, or Firm* — Adler Pollock & Sheehan P.C.

(57) ABSTRACT

Several methods for prediction and detection of neurological events are proposed based on spatiotemporal patterns in recorded neural signals. The methods are illustrated with examples from neural data recorded from human and non-human primates.

29 Claims, 31 Drawing Sheets

(51) Int. Cl.
    *A61B 5/0482* (2006.01)
    *A61B 5/04* (2006.01)
    *A61B 5/048* (2006.01)

(52) U.S. Cl.
    CPC .......... *A61B 5/0476* (2013.01); *A61B 5/0482* (2013.01); *A61B 5/7282* (2013.01)

(56) References Cited

U.S. PATENT DOCUMENTS

| | | | | |
|---|---|---|---|---|
| 7,212,851 | B2* | 5/2007 | Donoghue | A61B 5/04001 600/378 |
| 8,521,294 | B2* | 8/2013 | Sarma | A61B 5/0478 607/45 |
| 8,615,311 | B2* | 12/2013 | Langhammer | A61N 1/0529 435/325 |
| 2003/0176905 | A1* | 9/2003 | Nicolelis | A61N 1/0529 607/116 |
| 2004/0006264 | A1* | 1/2004 | Mojarradi | A61B 5/0478 600/378 |
| 2004/0082875 | A1* | 4/2004 | Donoghue | A61B 5/04001 600/544 |
| 2005/0203366 | A1* | 9/2005 | Donoghue | A61B 5/04002 600/378 |
| 2007/0067003 | A1* | 3/2007 | Sanchez | A61N 1/36082 607/45 |
| 2009/0124965 | A1* | 5/2009 | Greenberg | A61N 1/0531 604/67 |
| 2009/0171168 | A1* | 7/2009 | Leyde | A61B 5/048 600/301 |
| 2009/0319451 | A1 | 12/2009 | Mirbach et al. | |
| 2010/0292602 | A1* | 11/2010 | Worrell | A61B 5/0478 600/544 |
| 2011/0224752 | A1* | 9/2011 | Rolston | A61B 5/04001 607/45 |
| 2012/0004716 | A1* | 1/2012 | Langhammer | A61N 1/0529 607/148 |
| 2012/0016436 | A1* | 1/2012 | Sarma | A61B 5/0478 607/46 |

OTHER PUBLICATIONS

Staba et al. Sleep states differentiate single neuron activity recorded from human epileptic hippocampus, entorhinal cortex, and subiculum. J Neurosci 2002; 22: 5694-5704.

Tang et al. A maximum entropy model applied to spatial and temporal correlations from cortical networks in vitro. J. Neurosci. 2008; 28, 505-518.

Truccolo et al. A point process framework for relating neural spiking activity to spiking history, neural ensemble and extrinsic covariate effects. J. Neurophysiol. 2005; 93, 1074-1089.

Truccolo et al. Primary motor cortex tuning to intended movement kinematics in humans with tetraplegia. J Neurosci 2008; 28: 1163-1178.

Truccolo et al., "Single-neuron dynamics in human focal epilepsy", Nature Neuroscience 2011; 14(5) 635-641.

Truccolo et al.. Collective dynamics in human and monkey sensorimotor cortex: predicting single neuron spikes. Nature Neurosci 2010; 13: 105-111.

Ulbert et al. Laminar analysis of human neocortical interictal spike generation and propagation: current source density and multiunit analysis in vivo. Epilepsia 2004; 45 (Suppl 4): 48-56.

Vargas-Irwin et al. Reconstructing reach and grasp actions using neural population activity from primary motor. cortex. Soc. Neurosci. Abstr. 673.18, 2008.

Delgado-Escueta et al. The selection process for surgery of intractable complex partial seizures: Surface EEG and depth electrography. In: Ward AA Jr, Penry JK, Purpura DP, editors. 1983; Epilepsy. New York: Raven press, p. 295-326.

Wessberg et al. Real-time prediction of hand trajectory by ensembles of cortical neurons in primates. 2000 Nature 408, 361-365.

Wyler et al. Neurons in human epileptic cortex: correlation between unit and EEG activity. Ann Neurol 1982; 11: 301-308.

Yousry et al. Localization of the motor hand area to a knob on the precentral gyrus. A new landmark. Brain 1997; 120,141-157.

Yu et al. A small world of neuronal synchrony. Cereb. Cortex 2008; 18, 2891-2901.

International Search Report and Written Opinion of the International Searching Authority dated Aug. 24, 2012 in PCT/US11/063269 (10 pages).

Amritkar et al. Spatially synchronous extinction of species under external forcing. Physical Review Letters 2006; 96: 258102.

Amritkar et al. Stability of multicluster synchronization. International J Bifurc Chaos 2009; 19(12): 4263-4271.

Arieli et al. Dynamics of ongoing activity: explanation of the large variability in evoked cortical responses. Science 1996; 273, 1868-1871.

Ashe et al. Movement parameters and neural activity in motor cortex and area-5. Cereb. Cortex 1994; 4, 590-600.

Babb et al. Firing patterns of human limbic neurons during stereoencephalography (SEEG) and clinical temporal lobe seizures. Electroencephalography Clin Neurophysiol 1987; 66: 467-482.

Bamber. The area above the ordinal dominance graph and the area below the receiver operating characteristic graph. J. Math. Psychol. 1975; 12, 387-415.

Bartho et al. Characterization of neurocortical principal cells and interneurons by network interactions and extracellular features. J Neurophysiol 2004; 92: 600-608.

Besag. Statistical analysis of non-lattice data. Statistician 1975; 24, 179-195.

Bragin et al. Termination of epileptic afterdischarge in the hippocampus. J Neurosci 1997; 17(7): 2567-2579.

Buckmaster. Laboratory animal models of temporal lobe epilepsy. Comp Medicine 2004; 54(5): 473-485.

Connors. Initiation of synchronized neuronal bursting in neocortex. Nature 1984; 310: 685-687.

Destexhe et al. The high-conductance state of neocortical neurons in vivo. Nat. Rev. Neurosci. 2003; 4, 739-751.

Elston et al. The pyramidal cell of the sensorimotor cortex of the macaque monkey: phenotypic variation. Cereb. Cortex 2002; 12, 1071-1078.

Engel et al. Invasive recordings from the human brain: clinical insights and beyond. Nature Rev Neurosci 2005; 6: 35-47.

Fawcett. An introduction to ROC analysis. Pattern Recognit. Lett. 2006; 27, 861-874.

Fisher et al. Epileptic seizures and epilepsy: definitions proposed by the Internation League Against Epilepsy (ILAE) and the International Bureau for Epilepsy (IBE). Epilepsia 2005; 46(4): 470-472.

Geman et al. Stochastic relaxation, Gibbs distributions, and the Bayesian restoration of images. IEEE Trans. Pattern Anal. Mach. Intell. 1984; 6, 721-741.

Geman et al. Markov random field image models and their application to computer vision. Proc. Int. Congr. Math. 1986; 1496-1517.

Geweke. Measurement of linear dependence and feedback between multiple time series.J. Am. Stat. Assoc. 1982; 77, 304-314.

Halgren et al. Post-EEG seizure depression of human limbic neurons is not determined by their response to probable hypoxia. Epilepsia 1977; 18(1): 89-93.

Hatsopoulos et al. Encoding of movement fragments in the motor cortex. 2007; J. Neurosci. 27, 5105-5114.

Hochberg et al. Neuronal ensemble control of prosthetic devices by a human with tetraplegia. Nature 2006; 442: 164-171.

Hyvärinen. Consistency of Pseudolikelihood Estimation of Fully Visible Boltzmann Machines. Neural Comput. 2006; 18, 2283-2292.

Jacobs et al. Curing epilepsy: progress and future directions. Epilepsy & Behavior 2009; 14: 438-445.

Jaynes. On the rational of maximum-entropy methods. Proc. IEEE, 1982; 70, 939-952.

Jefferys. Models and mechanisms of experimental epilepsies. Epilepsia 2003; 44(suppl. 12): 44-50.

(56) References Cited

OTHER PUBLICATIONS

Jiruska et al. High-frequency network activity, global increase in neuronal activity, and synchrony expansion precede epileptic seizures in vitro. J Neurosci 2010; 30(16): 5690-5701.

Jones. et al. Intracortical connectivity of architectonic fields in the somatic sensory, motor and parietal cortex of monkeys. J. Comp. Neurol. 1978; 181(2) 291-347.

Kalaska et al. Cortical control of reaching movements. 1997 Curr. Opin. Neurobiol. 7, 849-859.

Keller et al. Heterogeneous neuronal firing patterns during interictal epileptiform discharges in the human cortex. Brain 2010; 133(6): 1668-1681.

Kim et al. Neural control of computer cursor velocity by decoding motor cortical spiking activity in humans with tetraplegia. J Neural Eng 2008; 5: 455-476.

Lado et al. How do seizures stop? Epilepsia 2008; 49(10): 1651-1664.

Lewicki. Bayesian modeling and classification of neural signals. Neural Comput 1994; 6: 1005-1030.

Lopes Da Silva et al. Dynamical diseases of brain systems: different routes to epilepsy. IEEE Trans Biomed Eng 2003; 50:540-549.

Marre et al. Prediction of spatiotemporal patterns of neural activity from pairwise correlations. Phys. Rev. Lett. 2009;102, 138101.

Moran et al. Motor cortical representation of speed and direction during reaching. J. Neurophysiol. 1999; 82, 2676-2692.

Mormann et al. Seizure prediction: the long and winding road. Brain 2007; 130: 314-333.

Paninski et al. Spatiotemporal tuning of motor neurons for hand position and velocity. J. Neurophysiol. 2004; 91, 515-532.

Paninski et al. Statistical models for neural encoding, decoding, and optimal stimulus design. Prog. Brain Res. 2007; 165, 493-507.

Philip et al. Continuous manual pursuit tracking of familiar and unfamiliar sequences through visual occlusions. Soc. Neurosci. Abstr. 2008; 672.22.

Pillow et al. Spatio-temporal correlations and visual signalling in a complete neuronal population. Nature 2008; 454, 995-999.

Pinto et al. Initiation, propagation, and termination of epileptiform activity in rodent neocortex in vitro involve distinct mechanisms. J Neurosci 2005; 25(36): 8131-8140.

Rosenberg et al. The partial epilepsies. The Clinical Neurosciences. 1983; New York: Churchill Livingston, vol. 2, Chapter 15pp. 1349-1380.

Santhanam et al. Hermes B: a continuous neural recording system for freely behaving primates. IEEE Trans Biomed Eng 2007; 54 (11): 2037-2050.

Schevon et al. Microphysiology of epileptiform activity in human neocortex. J Clin Neurophysiol 2008; 25; 321-330.

Schneidman et al. Weak pair-wise correlations imply strongly correlated network states in a neural population. Nature 2006; 440, 1007-1012.

Schwartzkroin. Basic mechanisms of epileptogenesis. In E. Wyllie, editor, the treatment of Epilepsy. 1993 Philadelphia: Lea and Febiger, pp. 83-98.

Serruya. et al. Instant neural control of movement signal. Nature 2002; 416, 141-142.

Shadmehr et al. A computational neuroanatomy for motor control. Exp. Brain Res. 2008; 185, 359-381.

Shimazu et al. Macaque ventral premotor cortex exerts powerful facilitation of motor cortex outputs to upper limb motoneurons. J. Neurosci. 2004;24, 1200-1211.

Amit, "Modeling Brain Function: The World of Attractor Neural Networks", Cambridge University Press, 1989, 504 pages.

Beal, "Single-Neuron Activity in Epilepsy", Nature Reviews Neurology, vol. 7, No. 243, 2011, 1 page.

Braitenberg et al., "Cortex: Statistics and Geometry of Neuronal Connectivity", Springer-Verlag, New York, 1998.

Cover et al., "Elements of Information Theory", Wiley and Sons, 1991, 563 pages.

Daley et al., "An Introduction to Theory of Point Processes", Springer, New York, vol. I: Elementary Theory and Methods, Second Edition, 2003, 493 pages.

Dayan et al., "Theoretical Neuroscience: Computational and Mathematical Modeling of Neural Systems", MIT Press, Cambridge, Massachusetts, 2001, 476 pages.

Gidas, "Consistency of Maximum Likelihood and Pseudo-Likelihood Estimators for Gibbs Distributions", Stochastic Differential Systems, Stochastic Control Theory and Applications, Springer, New York, 1988, pp. 129-130.

Landau et al., "Statistical Physics", 3rd Edition, Butterworth & Heinemann, Oxford, vol. 5, 1980, 544 pages.

Lowenstein, "Edging Toward Breakthroughs in Epilepsy Diagnostics and Care", Nature Reviews, Neurology, vol. 11, Nov. 2015, 2 pages.

Penfield et al., "Epilepsy and the Functional Anatomy of the Human Brain", Neurology, vol. 4, No. 6, Jun. 1, 1954, 896 pages.

Trimble, "The Treatment of Epilepsy-Principles and Practice", E. Wyllie. Lippincott, Williams and Wilkins: Philadelphia, 2001, 1328 pages.

Truccolo, "Stochastic Models for Multivariate Neural Point Processes: Collective Dynamics and Neural Decoding", Analysis of Parallel Spike Trains, eds Grun, S. and Rotter, S., Springer, New York, 2010, pp. 321-322.

\* cited by examiner

METHODS FOR PREDICTION AND EARLY DETECTION OF NEUROLOGICAL EVENTS

RELATED APPLICATIONS

This application claims the benefit of international application PCT/US2011/063269 filed Dec. 5, 2011 in the PCT Receiving Office of the U.S. Patent and Trademark Office, which claims the benefit of U.S. provisional application 61/419,863 filed Dec. 5, 2010, which are entitled 'Methods for prediction and early detection of neurological events', inventors Truccolo W. et al., and U.S. provisional application 61/538,358 filed Sep. 23, 2011, entitled 'Methods for prediction and early detection of neurological events', inventors Truccolo W. et al., which are hereby incorporated herein by reference in their entireties.

GOVERNMENT SUPPORT

The invention was made with government support under contract number NINDS 5K01NS057389-03 awarded by the National Institutes of Health. The government has certain rights in the invention.

TECHNICAL FIELD

Methods for prediction, prognosis, detection, diagnosis, and closed-loop prediction/detection and control of neurological events (e.g., single neuron action potentials; seizure prediction and detection, etc.) are provided and illustrated with the analysis of substantial numbers of neocortical neurons in human and non-human primates.

BACKGROUND

Prediction, detection and control of neurological events, as for example events in neurological disorders remain important medical concerns. Epilepsy is a common type of neurological disorder. Seizures and epilepsy have been recognized since antiquity, yet the medical community continues to struggle with defining and understanding these paroxysms of neuronal activity. Epileptic seizures are commonly considered to be the result of monolithic, hypersynchronous activity arising from unbalanced excitation-inhibition in large populations of cortical neurons (Penfield W G, Jasper H H. Epilepsy and the functional anatomy of the human brain. 1954 Boston: Little Brown; Schwartzkroin P A. Basic mechanisms of epileptogenesis. In E. Wyllie, editor, The treatment of Epilepsy. 1993 Philadelphia: Lea and Febiger, pp. 83-98; Fisher R S, et al. 2005 Epilepsia 46(4): 470-472). This view of ictal activity is highly simplified and the level at which it breaks down is unclear. It is largely based on electroencephalogram (EEG) recordings, which reflect the averaged activity of millions of neurons.

In animal models, sparse and asynchronous neuronal activity evolves, at seizure initiation, into a single hyper-synchronous cluster with elevated spiking rates (Jiruska P, et al. 2010 J Neurosci 30(16): 5690-5701; Pinto D J, et al. 2005 J Neurosci 25(36): 8131-8140), as the canonical view would suggest. How well these animal models capture mechanisms operating in human epilepsy remains an open question (Jefferys J G R. 2003 Epilepsia 44(suppl. 12): 44-50; Buckmaster P S. 2004 Comp Medicine 54(5): 473-485). Very few human studies have gone beyond macroscopic scalp and intracranial EEG signals to examine neuronal spiking underlying seizures (Halgren E, et al. 1977 Epilepsia 18(1): 89-93; Wyler A R, et al. 1982 Ann Neurol 11: 301-308; Babb T L, et al. 1987 Electroencephalography Clin Neurophysiol 66: 467-482; Engel A K, et al. 2005 Nature Rev Neurosci 6: 35-47). The relationship between single neuron spiking and interictal discharges showed 1-2 single units recorded from two patients, and neuronal activity during the ictal state was not exathined (Wyler A R, et al. 1982 Ann Neurol 11: 301-308). A few recorded neurons tended to increase their spiking rates during epileptiform activity (Babb T L, et al. 1987 Electroencephalography Clin Neurophysiol 66: 467-482). However, these recordings were limited to the amygdala and hippocampal formation, not neocortex, and mostly auras and subclinical seizures. Hence the behavior of single neurons in human epilepsy remains largely unknown.

Single-neuron action potential (spiking) activity depends on intrinsic biophysical properties and the neuron's interactions in neuronal ensembles. In contrast with ex vivo/in vitro preparations, cortical pyramidal neurons in intact brain each commonly receive thousands of synaptic connections arising from a combination of short- and long-range axonal projections in highly recurrent networks (Braitenberg, V et al., Cortex: Statistics and Geometry of Neuronal Connectivity, Springer-Verlag, New York, 1998; Elston, G. N. et al., 2002 Cereb. Cortex 12, 1071-1078; Dayan, P. et al., Theoretical Neuroscience, MIT Press, Cambridge, Mass., 2001). Typically, a considerable fraction of these synaptic inputs is simultaneously active in behaving animals, resulting in 'high-conductance' membrane states (Destexhe, A. et al., 2003 Nat. Rev. Neurosci. 4, 739-751); that is, lower membrane input resistance and more depolarized membrane potentials. The large number of synaptic inputs and the associated high-conductance states contribute to the high stochasticity of spiking activity and the typically weak correlations observed among randomly sampled pairs of cortical neurons.

SUMMARY

In all of the following, a method is used for prediction or detection of a neurological event depending on whether the information extracted from the neural signals is judged to be predictive of an upcoming neurological event or whether the information reflects an already occurring neurological event. A feature of the invention herein provides a method for predicting or detecting an occurrence of a neurological event in a subject, the method including steps of: recording continuous signals generated from single cells (for example neurons in the brain of the subject), identifying electrical signals generated from the single cells and measuring spiking activity of at least one recorded single neuron or other cell and characterizing the measured spiking activity of each recorded single neuron or other single cell as a collection of individual neural point process sample paths; estimating a sample path probability distribution of a collection of sample paths of length T computed in the time interval (t−T−W,t−T], for one or more neurons or cells, such that t is the current time, and W equals a time period of specified duration such that W>T>0; and determining, for each neuron or cell, whether a sample path measured in the time interval (t−T,t] for the given neuron or cell falls outside a given confidence interval of the current sample path distribution, such that the occurrence of the neurological event is predicted or detected by whether the measured sample path falls outside of the given confidence interval. The sample path distribution can be estimated based on histogram methods, or via parametric or nonparametric methods.

In a related embodiment, the sample paths of length T are overlapping sample paths.

In a related embodiment, the sample paths of length T are non-overlapping sample paths.

In a related embodiment the neurological event is predicted to occur or detected if the measured sample path falls outside of the given confidence interval. For example, the neurological event is predicted to occur or detected if a certain fraction of a plurality of measured sample paths in the time interval (t−T,t] from a corresponding set of recorded cells falls outside of the given confidence interval.

In a related embodiment, a neurological event is predicted to occur or detected if the weighted sum of the neurons, whose sample paths were computed on the interval (t−T, t] falls outside a given confidence interval of their corresponding sample path probability distributions computed on the interval (t−T−W, t−T], is above a given threshold. The weight for a given neuron is based on how important or reliable that neuron is judged to be for the event prediction or detection.

An embodiment of the method further provides that a neurological event is detected to occur if a certain fraction of a plurality of measured sample paths in the time interval (t−T, t] falls outside of the given confidence interval.

An embodiment of the method further provides a weight to each measured sample path based on how much the recorded neuron or other cell affects the sample path.

An embodiment of the method provides treating the subject based on the prediction, detection or diagnosis. For example, the subject is a patient having symptoms of the neurological event. Embodiments of the method further provide an early warning to the patient and/or medical personnel that a neurological event is predicted to occur or is occurring. For example, predicting an occurrence of the neurological event includes predicting and detecting epileptic seizures; diagnosing epilepsy; detecting changes in neuronal activity that indicate a disordered, diseased or injured state, including epilepsy, encephalopathy, neural oligemia or ischemia. For example, the method further includes predicting, detecting, making a diagnosis, monitoring, and making a prognosis of a disorder including but not limited to spreading cortical dysfunction following traumatic brain injury; incipient ischemia in cerebral vasospasm following subarachnoid hemorrhage; depth of pharmacologically-induced anesthesia, sedation, or suppression of brain activity; resolution of status epilepticus as determined during the treatment and emergence from pharmacology-induced burst-suppression behavior; and severity of metabolic encephalopathy in critical medical illness, including liver failure.

Another feature of the invention provides a method for continuously predicting or detecting an occurrence of a neurological event in a subject's body, the method including steps of: recording signals generated from single neurons or other cells in the brain of the subject and detecting electrical signals generated from the single neurons or other cells; measuring spiking activity of at least one recorded single neuron or other cell, such that the spiking activity of each neuron or other cell is represented as a spike train, and a conditional intensity function model of the spike train is estimated for each neuron or other cell and a probability of a given neuron or other cell spiking at a given time is calculated using the estimated conditional intensity function model; and, computing a receiver operating characteristic curve for each neuron or other cell from its corresponding spike train and calculated probability, and deriving a relative predictive power measure from the receiver operating characteristic curve, in such a way that the occurrence of the neurological event is determined from the measured relative predictive power.

For example, predicting an occurrence of the neurological event includes predicting and detecting epileptic seizures; diagnosing epilepsy; detecting changes in neuronal activity that indicate a disordered, diseased or injured state, including epilepsy, neural oligemia or ischemia. For example, the method further includes predicting, detecting, making a diagnosis and making a prognosis of at least one of the disorders that include spreading cortical dysfunction following traumatic brain injury; incipient ischemia in cerebral vasospasm following subarachnoid hemorrhage such as resolution of status epilepticus as determined during the treatment and emergence from pharmacology-induced burst-suppression behavior; and severity of metabolic encephalopathy in critical medical illness, including liver failure.

An embodiment of the method after representing the spike train further includes steps of: fitting a history point process model to each recorded neuron or cell using the spike train.

Another embodiment of the method after computing the receiver operating characteristic curve, further includes measuring the area under the curve (AUC).

Another embodiment of the method further includes predicting or detecting the occurrence of a neurological event if the relative predictive power calculated within the time interval (t−T,t] falls outside of a confidence interval of a prior determined relative predictive power.

For example, the step of calculating the probability of the ith neuron spiking at discrete time t, includes using the following equation:

$$Pr(x_{i,t}=1|H_t)=\lambda(t|H_t)\Delta+o(\Delta)\approx\lambda_i(t|H_t)\Delta, \quad \text{equation (1)}$$

where $x_{i,t}\in\{0,1\}$ denotes the state (0=no spike, 1=spike) of the ith neuron or cell at time t, $H_t$ is the spiking history up to, but not including, time t of all recorded neurons or other cells, $\lambda_i(t|H_t)$ is the conditional intensity function model of the ith neuron or cell, conditioned on all of the recorded spiking histories, $\Delta$ is the bin size for the discretization of time, and $o(\Delta)$ relates to the probability of observing more than one spike in a specified time interval.

For example, the step of fitting a history point process model includes using the following equation:

$$\log[\lambda_i(t|H_t)\Delta]=\mu_i+\sum_{k=1}^{p}K_{1,i,k}\cdot x_i+\sum_{j\neq i}^{C}\sum_{k=1}^{q}K_{2,i,j,k}\cdot x_j, \quad \text{equation (2)}$$

where $\mu_i$ relates to a background level of spiking activity; $x_i$ denotes the spiking history or spike train for the ith neuron or other cell, i=1, . . . , C recorded neurons or other cells; $K_{1,i,k}$ and $K_{2,i,j,k}$ comprise temporal basis functions with coefficients that are estimated. For example, when using raised cosine functions, ten (p=10) and four (q=4) basis functions can be used for the intrinsic and ensemble history filters, respectively. The conditional intensity function model is fitted based on data collected in a time window (not to be confused with the length of the spiking history) in the time interval (t−T−W,t], W>T>0.

For example, the relative predictive power (RPP) for the ith neuron or other cell is calculated according to the formula:

$$RPP_i=2(AUC_i-AUC_i^*), \quad \text{equation (3)}$$

wherein $AUC_i^*$ is the area under the ROC curve corresponding to a chance level predictor for a particular neuron or other cell and model, estimated via random permutation methods.

Another embodiment of the method further includes steps: fitting the conditional intensity function models to each recorded neuron or other cell based on data collected during a first time interval, (t−T,t], and fitting the multiple conditional intensity function models to each recorded neuron or other cell based on data collected during overlapping or non-overlapping time windows from a second time interval (t−T−W,t−T]; determining a relative predictive power for all of the recorded neurons or other cells during the first time interval under a cross-validation scheme; determining a probability distribution of relative predictive powers from each of the recorded neurons or other cells based on the RPPs computed from the multiple models fitted to data from the second time interval (also under a cross-validation scheme); and predicting or detecting the occurrence of the neurological event if at least a certain fraction of neurons or other cells have their RPPs, computed based on data from the interval (t−T,t] to fall outside a given confidence interval of their corresponding RPP probability distribution.

Another embodiment of the method comprises: fitting the conditional intensity function models to each recorded neuron or other cell based on data collected during a first time interval, (t−T, t], and fitting the multiple conditional intensity function models to each recorded neuron or other cell based on data collected during overlapping or non-overlapping time windows from a second time interval (t−T−W, t−T]; determining a relative predictive power for all of the recorded neurons or other cells during the first time interval; determining a probability distribution of relative predictive powers from each of the recorded neurons or other cells based on the RPPs computed from the multiple models fitted to data from the second time interval; and predicting or detecting the occurrence of the neurological event if the weighted sum of neurons, whose RPPs computed from data in (t−T, t] fall outside a given confidence interval of their corresponding RPP probability distributions, is above a given threshold. The weight for a given neuron is based on how important or reliable that neuron is judged to be for the event prediction.

Another embodiment of the method consists of fitting the conditional intensity function models to each recorded neuron or other cell based on data collected during a first time interval, (t−T,t], and fitting the multiple conditional intensity function models to each recorded neuron or other cell based on data collected during overlapping or non-overlapping time windows from a second time interval (t−T−W,t−T]; determining a probability distribution of relative predictive powers (computed under a cross-validation scheme) from all of the recorded neurons or other cells during the first time interval; determining a probability distribution of relative predictive powers (computed under a cross-validation scheme) from all of the recorded neurons or other cells during the second time interval; and predicting or detecting the occurrence of the neurological event if the two probability distributions are determined to be statistically different.

For example, predicting and detecting the occurrence of a neurological event includes predicting and detecting epileptic seizures; diagnosing epilepsy; detecting changes in neuronal activity that indicate a disordered, diseased or injured state, including epilepsy, neural oligemia or ischemia. For example, the method further includes predicting, detecting, and making a diagnosis and making a prognosis of at least one the disorders that include spreading cortical dysfunction following traumatic brain injury; incipient ischemia in cerebral vasospasm following subarachnoid hemorrhage such as resolution of status epilepticus as determined during the treatment and emergence from pharmacology-induced burst-suppression behavior; and severity of metabolic encephalopathy in critical medical illness, including liver failure.

An embodiment of the method provides treating the subject based on the prediction, detection or diagnosis. For example, the subject is a patient having symptoms of the neurological event. Embodiments of the method further provide an early warning to the patient and/or medical personnel that a neurological event is predicted to occur or is occurring.

An embodiment of the invention herein provides a method for continuously predicting or detecting an occurrence of a neurological event in a patient, the method including steps: recording signals generated from a plurality of single neurons or other cells in the brain of the patient and detecting electrical signals generated from the single neurons or other cells; measuring spiking activity of a corresponding plurality of recorded single neurons or other cells, such that the spiking activity of each neuron or other cell is represented as a spike train; estimating a conditional intensity function model of the spike train for each neuron or other cell, and deriving a graphical model from estimated conditional intensity functions for the set of recorded neurons or other cells during the time interval (t−T,t], wherein t is the current time and T>0, such that a parameter is determined from the graphical model; and, comparing the parameter to a probability distribution of the same parameter determined during multiple windows in the time interval (t−T−W,t−T], W>T. The occurrence of a neurological event is predicted or detected to be occurring from the comparison.

In a related embodiment, the parameter for the graphical model includes graph density. For example, the graph density includes dividing number of directed edges by total possible number of edges.

An embodiment of the method provides treating the subject based on the prediction, detection or diagnosis. For example, the subject is a patient having symptoms of the neurological event. Embodiments of the method further provide an early warning to the patient and/or medical personnel that a neurological event is predicted to occur or is occurring.

For example, predicting an occurrence of the neurological event includes predicting and detecting epileptic seizures; diagnosing epilepsy; detecting changes in neuronal activity that indicate a disordered, diseased or injured state, including epilepsy, neural oligemia or ischemia.

For example, the method further includes predicting, detecting, and making a diagnosis and making a prognosis of at least one the disorders that include spreading cortical dysfunction following traumatic brain injury; incipient ischemia in cerebral vasospasm following subarachnoid hemorrhage such as resolution of status epilepticus as determined during the treatment and emergence from pharmacology-induced burst-suppression behavior; and severity of metabolic encephalopathy in critical medical illness, including liver failure.

An embodiment of the method provides treating the subject based on the prediction, detection or diagnosis. For example, the subject is a patient having symptoms of the neurological event. Embodiments of the method further provide an early warning to the patient and/or medical personnel that a neurological event is predicted to occur or is occurring.

A feature of the invention herein provides a method for continuously predicting or detecting an occurrence of a neurological event in a subject, the method including: recording signals generated from single neurons or other cells in the brain of the subject, detecting electrical signals generated from the single neurons or other cells, and measuring spiking activity of at least one recorded single neuron or other cell; measuring a neural electric field potential and estimating a pairwise spike-field spectral coherence between the spike train and the field potential at a given frequency f; for each pair of recorded neuron (or other cell) and field potential, such that the spectral coherence is determined according to $$C_{X_iY_j}(f) = \frac{S_{X_iY_j}(f)}{\sqrt{S_{X_i}(f)S_{Y_j}(f)}},$$  equation (4)

wherein $X_i$ represents the spike train of the ith single neuron or cell, i=1, . . . , N recorded units, $Y_j$ represents the measured electric field potential, j=1, . . . , M recorded sites; $X_i$ and $Y_j$ are recorded from a same time window in the time interval (t−T−W,t], wherein t is the current time, W>T>0, $S_{X_iY_j}$ (f) is the cross-power at frequency f, $S_{X_i}$(f) and $S_{Y_j}$(f) correspond to the autopower of $X_i$ and $Y_j$ at the frequency f; respectively; computing two probability distributions of the estimated spike-field spectral coherences for all of the (i, j) pairs at each frequency, such that the first probability distribution is current and is based on data collected during the time interval (t−T,t] and the second probability distribution is based on at least one time window from the time interval (t−T−W,t]; and predicting or detecting the occurrence of a neurological event based on a comparison of the two probability distributions.

In a related embodiment of the prediction and detection methods the electrical field potential includes multi-unit activity.

In a related embodiment of the method the second probability distribution is based on a single time window collected during the time interval (t−T−W,t−T].

In a related embodiment of the method the comparison includes utilizing a statistical test.

In a related embodiment of the method the occurrence of the neurological event is predicted or detected if the two distributions are determined to be statistically different.

In a related embodiment of the method the statistical test includes a two-sample Kolmogorov-Smirnov test.

Various related embodiments of the method include one or more of the following: the second probability distribution is based on spike-field coherence estimated from a plurality of nonoverlapping windows collected during the time interval (t−T−W,t−T]; the comparison includes utilizing a statistical test; the occurrence of the neurological event is predicted or detected if the two distributions are determined to be statistically different; the statistical test includes a two-sample Kolmogorov-Smirnov test; and, the occurrence of a neurological event is predicted or detected if a currently determined Spike-Field spectral coherence falls outside of a confidence interval of the second probability distribution.

For example, predicting an occurrence of the neurological event includes predicting and detecting epileptic seizures; diagnosing epilepsy; detecting changes in neuronal activity that indicate a disordered, diseased or injured state, including epilepsy, neural oligemia or ischemia. For example, the method further includes predicting, detecting, and making a diagnosis and making a prognosis of at least one the disorders that include spreading cortical dysfunction following traumatic brain injury; incipient ischemia in cerebral vasospasm following subarachnoid hemorrhage such as resolution of status epilepticus as determined during the treatment and emergence from pharmacology-induced burst-suppression behavior; and severity of metabolic encephalopathy in critical medical illness, including liver failure.

An embodiment of the method provides treating the subject based on the prediction, detection or diagnosis. For example, the subject is a patient having symptoms of the neurological event. Embodiments of the method further provide an early warning to the patient and/or medical personnel that a neurological event is predicted to occur or is occurring.

BRIEF DESCRIPTION OF DRAWINGS

FIG. 1 panel A shows the 10×10 microelectrode array. The array's platform is 4.2×4.2 mm, with minimum inter-electrode distance of 400 μm. Maximum inter-electrode distance was ~2 cm (for electrodes in two arrays).

FIG. 1 panel. B shows dual array recordings: two implanted arrays in arm related areas of monkey primary motor (M1) and parietal (5d) cortex. PCD stands for posterior central dimple and "midline" corresponds to the sagittal suture. The arrow point to the anterior (A) direction.

FIG. 1 panel C shows array implanted in the arm (knob) area of primary motor cortex, human subject 3 (hS3). The labeled vein of Trolard is a large superficial vein that runs atop the central sulcus. The arrows point to anterior and lateral (L) directions.

FIG. 1 panel D shows dual array recordings from monkey M1 and ventral premotor (PMv) areas. Monkey subjects are represented by mLA, mCL, mCO and mAB. The twelve datasets used in the analyses included 1,187 neuronal recordings: hS1 (n=22, n=21), hS3 (n=108, n=110), mLA (n=45, n=45), mCL (n=47, session 1; n=44, session 2), mCO (M1: n=148, n=109; PMv: n=77, n=109) and mAB (M1: n=104, n=110; 5d: n=41, n=47). Whether a single unit sorted from the same electrode on different days corresponded to the same neuron or not was not distinguished.

FIG. 2 panel A shows waveforms corresponding to all sorted spikes for neuron 34a used in these analyses.

FIG. 2 panel B shows intrinsic spiking history. The curve represents the estimated temporal filter for the intrinsic history. Values below or above 1 correspond to a decrease or increase, respectively, in spiking probability contributed by a spike at a previous time specified in the horizontal coordinate. Refractory and recovery period effects after a spike, followed by an increase in spiking probability at longer time lags (40-100 ms), can be seen. Without being limited by any particular theory or mechanism of action this late intrinsic history effect might also reflect network dynamics.

FIG. 2 panel C shows ensemble spiking history effects. Each curve represents the temporal filter corresponding to a particular input neuron to cell 34a. Many input neurons contributed biphasic effects: for example, an increase in spiking probability followed by a decrease, or vice-versa. All of the examined target neurons in datasets herein showed qualitatively similar temporal filters.

FIG. 2 panel D shows spike raster for all of the 110 neurons recorded in hS3 over a short, continuous time period.

FIG. 2 panel E shows predicted spiking probabilities for the target neuron 34a computed from the estimated intrinsic and ensemble temporal filters and the spike trains shown in panels B, C and D, respectively.

FIG. 2 panel F shows observed spike train for neuron 34a in the same period.

FIG. 3 panel A shows receiver operating characteristics (ROC) curves for neuron 34a (human participant hS3, n=110 neurons, session 2, including 240,000 samples). FP and TP denote false- and true-positive prediction rates, respectively. The diagonal line corresponds to the expected chance prediction. The black, dark grey and light grey ROC curves correspond to the prediction based on full history models, only the ensemble histories, or only the neuron's own spiking history, respectively. The inset shows the area under the curve (AUC) corresponding to the ROC curve for the ensemble history model.

FIG. 3 panel B shows ROC curves for neuron 16a (monkey mLA, n=45, session 2, 1,230,857 samples). 95% confidence intervals for the AUC chance level resulted in 0.51±0.004 and 0.51±0.017 for target neurons 16a and 34a, respectively. The black, dark grey and light grey ROC curves correspond to the prediction based on full history models, only the ensemble histories, or only the neuron's own spiking history, respectively. These narrow confidence intervals were typical for the recorded neurons.

FIG. 3 panel C shows a distribution of Pearson correlation coefficients computed over all of the neuron pairs for hS3 (1-ms time bins). N corresponds to the number of neuron pairs. Each of these correlation coefficients corresponds to the extremum value of the cross-correlation function computed for time lags in the interval±500 ms. Inset, normalized absolute (extremum) correlation coefficients for all of the neuronal pairs in the ensemble from hS3 computed for spike counts in 50-ms time bins; about 90% of the pairs had a correlation value smaller than 0.06 (vertical line).

FIG. 3 panel D shows a distribution of correlation coefficients computed over all of the neuron pairs for mLA (1-ms time bins).

FIG. 4 panels A-D show distributions of predictive power corresponding to target neurons from subjects mLA (panel A), mCL (panel B), hS1 (panel C) and hS3 (panel D). Each distribution includes target neurons recorded in two different sessions (mLA: n=45, n=45; mCL: n=47, n=44; hS1: n=22, n=21; hS3: n=108, n=110). The left column shows the distribution of predictive power based on the full history model and the right column compares the predictive power of the two (intrinsic and ensemble) history components separately. The predictive power measure is based on the AUC scaled and corrected for chance level prediction. It ranges from 0 (no predictive power) to 1 (perfect prediction). For many neurons, the predictive power of separate components (intrinsic and ensemble) could add to a value larger than 1 or result in a larger predictive power than that obtained by the full history model. This indicates that there was some redundancy in the information conveyed by these two components. The numbers of predicted samples (1-ins time bins) were 864,657 and 1,230,857 for mLA, 1,220,921 and 1,361,811 for mCL, 240,000 in both sessions for hS1 and 240,000 in both sessions for hS3.

FIG. 8 panels A-D show distributions of instantaneous collective states that were approximated using maximum entropy distributions constrained on empirical mean spiking rates and zero time-lag pair-wise correlations. The left column shows the empirical distribution of the observed number of multi-neuron spike coincidences in the ensemble ($\Delta$=1 ms) and the distribution generated from the maximum entropy model using Gibbs sampling (line with triangle marks). The middle column shows the distribution of predictive power values. Predictive power was computed for each target neuron separately, with the instantaneous or simultaneous collective state defined at a temporal resolution of 1 ms. For each given neuron, predictions were determined by a conditional spiking probability derived from the maximum entropy joint distribution model and knowledge of all of the (n−1) neurons' simultaneous states. The right column shows the distribution of predictive power when the instantaneous state was defined at a coarser temporal resolution of 10 ms. In that case, time bins containing more than one spike were set to 1. For each monkey and human participant, data from two sessions were used in these analyses. The rows correspond to mLA (n=45, n=45, panel A), mCL (n=47, n=44, panel B), hS1 (n=22, n=21 panel C) and hS3 (n=108, n=110, panel D).

FIG. 9 panel A on the left shows a distribution of predictive power values for target neurons in area PMv (subject mCO), which were recorded during free reach-grasp movements. Predictive power was computed from full history models that also included spiking histories in M1. Right, comparison of the power of intra (PMv, n=77, n=109) and inter-areal (M1, n=148, n=109) ensemble histories to predict spiking in PMv. The predictive power M1→PMv tended to be higher than the local PMv→PMv in this case, where the number of neurons recorded in M1 was larger than in PMv. In contrast, additional analyses using balanced-size ensembles indicated that intra-areal predictive power was actually slightly higher (FIG. 10).

FIG. 9 panel B on the left shows a distribution of predictive power for target neurons in M1. Predictive power was computed from full history models that also included spiking histories in PMv. Right, comparison of the power of the intra (M1) and inter-areal (PMv) ensemble histories to predict spiking in M1.

FIG. 9 panels C and D show data presented as in panels A and B and computed for parietal 5d (n=41, n=47) and M1 (n=104, n=110), recorded from monkey mAB during a planar pursuit tracking task. The numbers of predicted samples were 212,028 and 99,008 for mCO (sessions 1 and 2, respectively) and 416,162 and 472,484 for mAB (sessions 1 and 2, respectively).

FIG. 10 panels A, B and C, D show the comparisons for the M1-PMv and M1-5d pairs, respectively. The term "Δ predictive power" denotes the difference between intra and inter-areal ensemble predictive power. For example, (PMv→PMv)−(M1→PMv) represents the difference between the predictive power of intra-areal ensembles in PMv and inter-areal ensembles in M1 to predict single neuron spiking activity in PMv. Balanced-size ensembles: M1-PMv, n=77 and n=109, for sessions 1 and 2, respectively; M1-5d, n=41 for both sessions.

FIG. 11 panel A shows the predictive power of full history models versus the mean spiking rate (in spikes per s) of the target neurons is shown.

FIG. 11 panel B shows the coefficient of variation (CV) of the inter-spike time intervals versus spiking rates.

FIG. 11 panel C shows predictive power of full history models versus coefficients of variation of the predicted spiking activity. Lower coefficients indicate more regular spike trains. Coefficients around 1 and below tended to correspond to a broad range of predictive power, and higher coefficients tended to cluster around intermediate predictive power values. In summary, the predictive power of history models did not depend, in a simple manner, on mean spiking rates or on the level of irregularity of the spiking activity.

FIG. 11 panel D shows predictive power versus the information rate (in bits per s) involved in the prediction. Approximately equal predictive power could relate to a broad range of information rates.

FIG. 12 panel A shows location of the microelectrode array in Patient A (square).

FIG. 12 panels B and C show a 16 mm$^2$, 96-microelectrode array.

FIG. 12 panel D shows electrocorticograph (ECoG) traces recorded at the locations shown in panel A. Seizure onset is at time zero. The LFP (low-pass filter at 250 Hz) recorded from a single channel in the microeletrode array and the corresponding spectrogram (in dB) are shown in the lower panel.

FIG. 12 panel E shows the neuronal spike raster plot of the recorded neurons (n=149) for Patient A during seizure 1. Each hash mark represents the occurrence of an action potential. Neurons were ranked (vertical axis) in increasing order according of their mean firing rate during the seizure. This ranking number is not to be confounded with the neuron label, nor does it indicate anything about the relationship of the neurons to each other in space. Some neurons increased their firing rate during the initial period of the seizure, while others decreased. Some of the latter stopped firing during the seizure. In addition, some of the neurons that initially decreased their firing rates showed a transient increase during a later period. Towards the end of the seizure, the majority of neurons were active until spiking was abruptly interrupted at seizure termination. With the exception of a few neurons, the recorded population remained silent for about 20 seconds.

FIG. 12 panel F shows that the mean population rate, the percentage of active neurons and the Fano factor (FF), determined in 1-second time bins, were roughly stationary during the several minutes preceding the seizure onset. An increase in the Fano factor, reflecting the heterogeneity in neuronal spiking, was observed around seizure onset and preceded an increase in the mean population rate. Similar heterogeneity in neuronal modulation patterns were also observed for other seizures across the patients (FIG. 14).

FIG. 13 panels A is a raster of spike counts.

FIG. 13 panels A and B show heterogeneity of spiking activity in Patient B. Seizure 1 is higher during the early stages of seizure initiation, as also reflected in the peak in the Fano factor of the spike counts (in 1-second time bins) across the population. The population spiking gradually increases during this period as well as the percentage of coactive neurons (also computed within 1-second time bins). At the end of this initial period, about 60% of the neurons have become active and this percentage jumps to the activation peak (approximately 97%). Nevertheless, even at this time, heterogeneity can still be observed in spiking activity. For example, the neuron ranked 11 essentially 'shuts down' after this peak activity.

FIG. 13 panels C and D show that seizure 1 in Patient C had a relatively short duration (about 11 s). Heterogeneous spiking behavior is most prominent during the first 5 seconds of the seizure. The Fano factor peaks near seizure onset and shows also several transient increases preceding the seizure. During the second half of the seizure, several synchronized bursts of activity can also be seen in the population spike rate and in the percentage of active neurons. These bursts, interspaced with brief silences, resemble failed seizure terminations. After a postical silence lasting about 5 s, a brief period of higher activity follows.

FIG. 13 panels E and F show that seizure 1 in Patient D appeared as a very mild event at the microelectrode site. It can be hardly detected on the population spike count rate, in the percentage of coactive neurons or in the Fano factor for the spike counts across the population. Nevertheless, visual inspection of the spike rasters reveals two main neuronal groups: one neuronal group with a buildup in activity (starting around 20 seconds into the seizure) and the other with a decrease during the initial 30-40 seconds. Based on ECoG analyses, the seizure lasted for 43 seconds.

FIG. 14 panels A and B show two consecutive seizures in two of the patients occurred within approximately 1 hr. allowing an examination of the reproducibility of neuronal spiking patterns across different seizures. An example from Patient A with 131 neurons is shown. Following conventions used in FIG. 12, the neuron number corresponds to ranking based on mean rates measured during the seizure.

FIG. 14 panel B shows the ranking used for seizure 2 was also used. (i.e., the single units in any given row of seizure 2 and 3 are the same.) Most neurons coarsely preserved the types of firing rate modulation across the two seizures. For example, neuron 69 stops firing around seizure onset in both seizures, only to resume just after seizure termination; the lowest ranked neurons decrease or stop firing; and many of the top ranked neurons presented similar transient increases in firing rate modulation. The correlation coefficient between two spike trains during the initial 30 seconds of each seizure, for each neuron and averaged across the population, was 0.82. As in seizure 1 (FIG. 12), an almost complete silence in the neuronal population occurs abruptly at seizure termination. Similar reproducibility was also observed for two consecutive seizures recorded from Patient B (FIG. 15).

FIG. 14 panel C shows the corresponding LFPs and spectrograms (from the same microelectrode array channel shown in FIG. 12) on the right.

FIG. 14 panel D shows the Fano factor (FF) for the spike counts in the population of recorded neurons showed similar increase during both seizures, reflecting the increased heterogeneity in neuronal spiking across the population.

FIG. 15 panels C and D show reproducibility of neuronal spiking modulation patterns across consecutive seizures, Seizures 1 and 2 in Patient C, respectively. Whether the same neurons were recorded in these two seizures was not determined because they were separated by several hours, however a level of reproducibility of a general modulation pattern over the entire neuronal ensemble can be observed. According to ECoG inspection, both electrographic seizures lasted about 11 seconds. Each population raster contains a different number of neurons. In contrast with FIG. 14, and the two population rasters for Patient B herein, neurons with the same ranking might relate to different single units.

FIG. 17 panel A shows the spike train (at the bottom) corresponds to neuron 90-1 (A2: Patient A, seizure 2). Seizure onset corresponds to time zero. The inset shows the mean and ±2 SD of the recorded spike waveforms for this neuron. The black curve corresponds to the sample path during the period. For comparison purposes, the initial value of the sample path is set to zero. The shaded band corresponds to the range of all of the 3-minute long sample paths observed during a 30-minute interictal period preceding the preictal period. Interictal sample paths in this distribution were obtained from an overlapping 3-minute long moving time window, stepped 1 second at a time. Curves above and below the black curve correspond to the average sample path and 95% confidence intervals. In a more conservative assessment, a sample path was judged to have deviated from the interictal sample paths when it fell outside the range of the collection of interictal sample paths at any given time. In this example, the preictal sample path did not deviate from the observed paths during the interictal period.

FIG. 17 panel B shows the sample path during the seizure (bottommost curve; ictal sample path) does deviate from the observed interictal paths, as expected in this case where the neuron transiently stops spiking for tens of seconds just after the seizure onset. The neuron's spiking rate gradually recovers and eventually settles at the typical mean rate (approximately straight line at the end).

FIG. 17 panel C shows four examples (one for each patient) of preictal and ictal sample path deviations. For patient A2 the top and the bottom curves correspond to preictal and ictal sample paths respectively. For patients B2 and C2 the first and the second curves from the left correspond to ictal and preictal sample paths respectively. For patient D the first and the second curves from the left at the top right corner represent preictal and ictal sample paths respectively. For all patients curves in the shaded region correspond to the average sample path and 95% confidence intervals. Although the preictal and ictal sample path are plotted along the same axis, they refer to a 3-minute period before and after, respectively, the seizure onset. Whereas in most cases a preictal increase (decrease) was followed by an ictal increase (decrease), some neurons had the opposite preictal and ictal behavior, as shown in the top left plot.

FIG. 18 panels A-C show that despite variability in preictal and ictal activity, several neurons yielded consistent preictal and ictal deviations with respect to a preceding interictal period (Patient A), as represented by relatively straight traces in the shaded region.

FIG. 18 panel D is an example of a neuron from Patient B which showed a preictal deviation in the second seizure, and not in the first.

DETAILED DESCRIPTION

Figure 1:
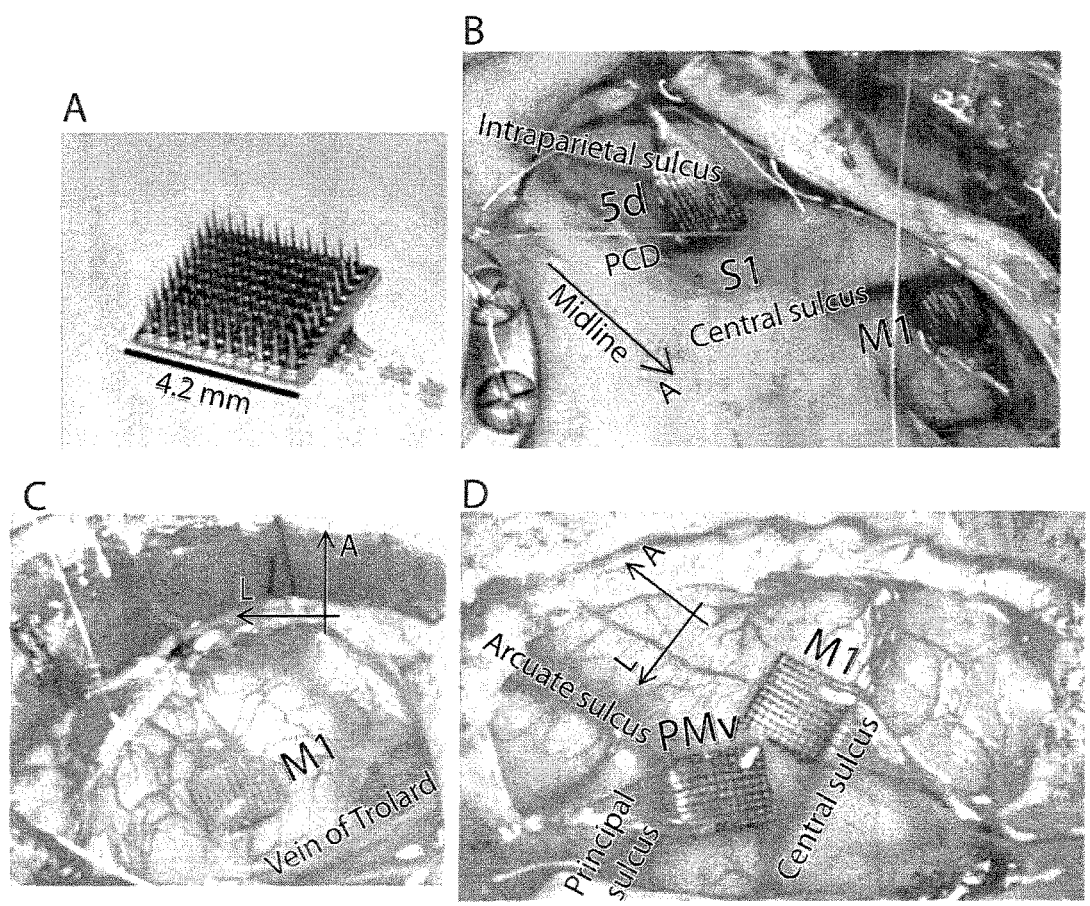
FIG. 1 is a set of photographs showing single and dual microelectrode array recordings from human and non-human primate sensorimotor cortex. Chronically implanted arrays are shown during the surgery. Recordings reported here were performed weeks to months after surgical implantation.

Embodiments of the invention provide exemplary systems for predicting the occurrence of a neurological event, e.g., epilepsy: a system for predicting occurrence of a neurological event in a patient's body based on neural point process sample paths (spike trains generated by a sequence of action potential events) and their corresponding distributions; a system for predicting occurrence of a neurological event in a patient's body based on measured relative predictive power as defined below of ensemble point process histories, i.e., the collection of past spike trains in the recorded neuronal ensemble, for any neuron in the ensemble; a system for predicting occurrence of a neurological event in a patient's body based on properties of the graphical model, i.e., functional connectivity pattern, induced by the fitted history point process models, and system for predicting occurrence of a neurological event in a patient's body based on the spectral coherence between the neural point process and a recorded local field potential.

The systems are based on intracellular or extracellular recordings of neuronal action potentials (APs) and local field potentials (LFPs) from brain areas. These signals are recorded via single or multiple electrodes. APs of single- or multi-units are represented as point processes, i.e., as a sequence of time of events, where event refers to the occurrence of an AP. Furthermore, these sequences are typically represented in discrete time (e.g., $\Delta=1$ ins resolution), originating a binary sequence, e.g., $\{0, 0, 0, 1, 0, 0, 0, \ldots\}$. LFPs are typically recorded broadband (0.3 Hz-7.5 kHz) and are sampled accordingly. More detailed description of basic statistical methods to be described below can be found in Truccolo et al. entitled "Collective dynamics in human and monkey sensorimotor cortex: predicting single neuron spikes", Nature Neuroscience 11:73 (2010), published online Dec. 6, 2009, which is hereby incorporated herein by reference in its entirety. In addition, several examples that illustrate many of the quantities and measures used in the proposed prediction and detection systems are provided below.

Coordinated spiking activity in neuronal ensembles, in local networks and across multiple cortical areas, is thought to provide the neural basis for cognition and adaptive behavior. Abnormality in this coordinated activity is also considered to be the basis of many neurological disorders and diseases. Examining such coordinated activity or collective dynamics at the level of single neuron spikes has remained, however, a considerable challenge. Examples herein show that the spiking history of small and randomly sampled ensembles (approximately 20 to 200 neurons) could predict subsequent single neuron spiking with substantial accuracy in the sensorimotor cortex of humans and nonhuman behaving primates. Furthermore, spiking was better predicted by the ensemble's history than by the ensemble's instantaneous state (Ising models), emphasizing the role of temporal dynamics leading to spiking. Notably, spiking could be predicted not only by local ensemble spiking histories, but also by spiking histories in different cortical areas. These strong collective dynamics provide a basis for understanding cognition and adaptive behavior at the level of coordinated spiking in cortical networks, and also for prediction and detection and medical and/or surgical management of neurological events.

Examples herein analyze cortical microelectrode array recordings in humans and monkeys to determine the predictability of single-neuron spiking on the basis of the recent (<100 ms) spiking history of small, randomly sampled neuronal ensembles from the same (intra) or from a different (inter), but connected, cortical area. The predictive power of ensemble spiking histories and instantaneous collective states was compared. Substantial predictability in these small and randomly sampled ensembles would imply strong collective dynamics, with implications for both cortical processing and the experimental endeavor of studying coordinated spiking in large, distributed cortical networks.

Tens to hundreds of randomly and simultaneously sampled neurons were studied in small (4×4 mm) patches in arm-related areas of primary motor (M1), parietal (5d) and ventral premotor (PMv) cortices while humans (M1) and monkeys (M1-PMv and M1-5d) performed sensorimotor tasks. Beyond their local connectivity, M1-PMv and M1-5d are known to be bidirectionally connected (Jones, E. G. et al., 1978 J. Comp. Neurol. 181, 291-347; Shimazu, H. et al., 2004 J. Neurosci. 24, 1200-1211; their coordination is thought be important for reaching and grasping as shown in Kalaska, J. F. et al., 1997 Curr. Opin. Neurobiol. 7, 849-859; Shadmehr, R. et al., 2008 Exp. Brain Res. 185, 359-381), allowing analysis not only of local, but also of inter-areal, ensemble-based prediction. Point process models were fitted to express the spiking probability at any 1-ms time interval conditioned on the past 100 ms of the neuron's own (intrinsic) spiking history and the past 100 ms of the spiking history of the neuronal ensemble (Truccolo, W. et al., 2005 J. Neurophysiol. 93, 1074-1089; Paninski, L. et al., 2007 Prog. Brain Res. 165, 493-507; Truccolo, W. Stochastic point process models for multivariate neuronal spike train data: collective dynamics and neural decoding, in Analysis of Parallel Spike Trains, eds Grün, S. and Rotter, S., Springer, New York, 2009). On the basis of this conditional spiking probability, whether or not a target neuron would spike in any given 1-ms time bin was predicted. When examining the predictive power of the ensemble's simultaneous spiking state, simultaneity was defined at two levels of temporal resolution, 1 and 10 ms. These instantaneous collective states could result from common inputs or from synchronization patterns arising from the neuronal network's intrinsic dynamics. Pair-wise maximum entropy (Ising) models were used to approximate the distributions of these instantaneous collective states (Schneidman, E. et al., 2006 Nature 440, 1007-1012). Detailed receiver operating characteristic (ROC) curve analyses allowed quantifying and comparing of the predictive power of intrinsic and ensemble histories, intra- and inter-areal ensemble activity, and spiking histories and instantaneous collective states (Fawcett, T., 2006 Pattern Recognit. Lett. 27, 861-874).

The proposed methods are also illustrated with applications to the study of epileptic seizures. The reliance on the macroscopic information of the EEG has dominated attempts at discovering physiological changes preceding the seizure, with a goal in predicting and then preventing seizures (Lopes da Silva F H, et al. 2003 IEEE Trans Biomed Eng 50:540-549; Mormann F, et al. 2007 Brain 130: 314-333). While substantial evidence supports the concept of a distinct preictal state in focal seizures, reliable seizure prediction based on detection of preictal changes in human scalp and intracranial EEG has remained elusive (Mormann F, et al. 2007 Brain 130: 314-333).

Epileptic seizures are traditionally characterized as the ultimate expression of monolithic, hypersynchronous neuronal ensemble activity arising from unbalanced excitation. This canonical view is based primarily on macroscopic electroencephalogram recordings, which measure the averaged activity of millions of neurons simultaneously, and are insensitive to the detailed, information rich output of single neurons. Yet, a deeper understanding of the role of individual neurons during seizures could have profound implications for improving treatment for 50 million people worldwide suffering from epilepsy.

Most seizures end abruptly and spontaneously, followed by a post-seizure diminution in EEG activity (Lado F A, et al. 2008 Epilepsia 49(10): 1651-1664). The underlying mechanisms governing this behavior also are not understood. Various potential mechanisms including, among others, glutamate depletion, profound inhibition, modulatory effects from subcortical structures and depolarization block have been hypothesized to underlie seizure termination (Lado F A, et al. 2008 Epilepsia 49(10): 1651-1664; Bragin A, et al. 1997 J Neurosci 17(7): 2567-2579). While these mechanisms clearly operate at the level of individual cells, single unit activity during this period has not been examined in humans. Such information is needed to develop better strategies for termination and preventing status epilepticus (a condition in which seizure activity continues indefinitely unabatedly for more than 30 minutes or when two seizures occur consecutively without return to consciousness; see Treiman D M, 2001 Status epilepticus, in Wyllie E (Ed.), The treatment of epilepsy: principles and practice. Lippincott, Williams and Wilkins, Philadelphia).

Examples herein also describe the first examination of neuronal activity patterns in large ensembles of single neurons during seizures in human epilepsy (Truccolo et al., "Single-neuron dynamics in human focal epilepsy", Nature Neuroscience 14(5) 635-641 (2011)). Using 16 mm$^2$, 96-channel microelectrode arrays implanted into four patients with medically intractable focal epilepsy, spiking patterns were analyzed of 57-149 simultaneously recorded individual neocortical neurons during seizure initiation, maintenance, and termination. Contrary to what is anticipated from a mechanism of homogenous run-away excitation, individual neurons here showed a wide variety of behaviors during seizure initiation and maintenance. Neurons became active at different times during seizure propagation and exhibited distinct patterns with transient increases or decreases in spiking rates. Even at the spatial scale of small cortical patches, network dynamics during seizure initiation and spread were not observed to be hypersynchronous. Instead, the data showed complex interactions among different neuronal groups. The spatiotemporal heterogeneity tended to disappear towards the end of the seizure, at which point nearly all neurons abruptly and simultaneously ceased spiking. In contrast to earlier stages, seizure termination is a nearly homogenous phenomenon. Surprisingly, prior to the seizure onset, substantial numbers of neurons both within and outside the region of seizure onset demonstrated significant changes in activity, sometimes minutes before overt electro-clinical events. Overall, these results require a revision of current thinking about seizure mechanisms and open possibilities for seizure prediction and control based on spiking activity in ensembles of neocortical neurons.

The invention now having been fully described it is exemplified below, which examples are not to be construed as further limiting. References cited herein are hereby incorporated by reference in their entireties.

EXAMPLES

Example 1. Humans with Tetraplegia, Electrophysiology and Behavioral Tasks

An investigational device exemption (IDE) for these studies was obtained from the US Food and Drug Administration and all studies were performed with approval from Institutional Review Boards Spaulding Rehabilitation Hospital Institutional Review Board, New England Institutional Review Board, Rhode Island Hospital Institutional Review Board, Partners Human Research Committee. The recording device, preamplifiers, data acquisition systems and computer are part of the BrainGate Neural Interface System (Cyberkinetics Neurotechnology Systems, Inc), which is an investigational device, limited by federal law to investigational use. The sensor is a 10×10 array of silicon microelectrodes that protrude 1 mm (hS1) or 1.5 mm (hS3) from a 4.2×4.2 mm platform (FIG. 1). For signal acquisition, 96 electrodes are available, with minimum inter-electrode distance of 400 µm. Participant 1 (hS1) was a 24-year-old male with tetraplegia (C4 ASIA A). Participant 3 (hS3) in the pilot clinical trial is a 56-year-old female who sustained a pontine stroke 9 years before trial enrollment, resulting in loss of speech and locked-in syndrome, which later resolved to incomplete tetraplegia. After obtaining informed consent and carrying out the medical and surgical screening procedures, the array was implanted in the dominant M1 hand/arm area, identified anatomically as the 'knob' region[31,33] of the precentral gyrus in pre-operative magnetic resonance imaging (Hochberg, L. R. et al., 2006 Nature 442, 164-171; Yousry, T. A. et al., Brain 120, 141-157).

Each participant used M1 spiking activity to control a cursor displayed on a computer screen (Hochberg, L. R. et al., 2006 Nature 442, 164-171; Truccolo, W. et al., 2008 J. Neurosci. 28, 1163-1178). The participant was instructed to imagine moving a circular cursor displayed on the screen to one of four peripheral targets, positioned at 0, 90, 180 and 270°. In each session, 20 trials were collected for each of the four pseudo-randomly presented radial targets. The 3 s period after target appearance was included in the analysis. Two datasets per participant were used, corresponding to two research sessions conducted on two different days. Data sets were collected on 2004.09.16 and 2004.09.20 (hS1) and 2006.01.23 and 2006.01.24 (hS3). Spike-sorting utilities in Offline Sorter (Plexors) were used to identify and sort neuronal units in all of the human and nonhuman primate recordings. Whether a single unit sorted from the same electrode on different days corresponded to the same neuron or not was not distinguished.

Example 2. Nonhuman Primate Subjects, Electrophysiology and Behavioral Tasks Two datasets were recorded in two experimental sessions from each of four rhesus monkeys (*Macaca mulatta*). All recordings were obtained via single or dual cortically implanted 10×10 microelectrode arrays (electrode length, 1.0 mm), similar to the array described above. M1 neurons from monkeys mLA and mCL were recorded while they performed point-to-point planar movements. The monkeys used a manipulandum to move a position feedback cursor that was presented on the monitor. Targets were randomly placed (that is, uniform in two-dimensional space), one at a time, on the workspace. After the successful acquisition of a random number (3-9) of targets, the monkeys received a juice reward. Only segments of data recorded during the reaching phases of the tasks, from two experimental sessions, were included in the analyses (datasets: mLA, 2004.03.25 and 2004.03.26; mCL, 2004.03.25 and 2004.03.29). M1 and PMv neurons were simultaneously recorded from monkey mCO while this monkey performed reaching and grasping movements toward objects moving in the workspace (Vargas-Irwin, C. E. et al., Soc. Neurosci. Abstr. 673.18, 2008). A motion-capture system was used to record arm-hand configurations and related behavioral epochs. Only data segments corresponding to 1-s segments during the reach-grasp phase before the final object grasp, from two sessions, were included in the analyses (datasets: 2008.03.19 and 2007.12.12). M1 and 5d neurons were simultaneously recorded via dual arrays from monkey mAB. The monkey performed visually guided pursuit tracking of a circular cursor projected on a horizontal screen while wearing an external device for kinematic measurements (Kinarm, BKIN Technologies). This cursor followed randomly generated trajectories of varying speeds over the planar, horizontal workspace (Philip B. A. et al., Soc. Neurosci. Abstr. 672.22, 2008). Only data segments recorded during tracking, from two sessions, were included in the analyses (datasets 2008.05.08 and 2008.05.09). All procedures were in accordance with Brown University Institutional Animal Care and Use Committee approved protocols and the Guide for the Care and Use of Laboratory Animals.

Example 3. Point Process History Models

The distribution of the point process sample paths of a given $i^{th}$ neuron is completely specified (Truccolo, W. et al., 2005 J. Neurophysiol. 93, 1074-1089; Truccolo, W. Stochastic point process models for multivariate neuronal spike train data: collective dynamics and neural decoding. in Analysis of Parallel Spike Trains, eds Grün, S. and Rotter, S., Springer, New York, 2010; Daley, D. J. et al., An Introduction to Theory of Point Processes, Springer, New York, 2003) by the conditional intensity function $$\lambda_i(t \mid H(t), z(t)) = \lim_{\Delta \to 0} \frac{Pr(N_i(t+\Delta) - N_i(t) = 1 \mid H(t), z(t))}{\Delta}, \quad \text{equation (5)}$$

where $Pr(\cdot|\cdot)$ is a conditional probability, $N_i(t)$ denotes the sample path in the time interval (0, t] (that is, a right-continuous function that jumps 1 each time a spike occurs), H(t) denotes the conditioning intrinsic and ensemble spiking histories up to, but not including, time t, and z(t) denotes other relevant extrinsic covariates, such as stimuli and behavioral variables. Focus was placed on intensity function models conditioned on spiking histories (see FIG. 6 for analyses involving conditional intensity function models that also included extrinsic covariates such as hand position and velocity). The sample path distribution for the discrete time point process belongs to the exponential family with canonical parameter $\log(\lambda(t|H_t)\Delta)$, which was modeled as in equation (2)

$$\log(\lambda_i(t \mid H_t)\Delta) = \mu_i + \sum_{k=1}^{10} K_{1,i,k} \cdot x_i + \sum_{j \neq i} \sum_{k=1}^{4} K_{2,i,j,k} \cdot x_j$$

where t indexes discrete time, $\Delta=1$ ms, $\mu_i$, relates to a background level of spiking activity, and $x_i$ denotes the spiking history (spike train) in the time interval (t−100 ms, t) for the $i^{th}$ neuron, with $x_{i,t} \in \{0,1\}$ for i=1, n recorded neurons. $K_{1,i,k}$ and $K_{2,i,j,k}$ consisted of temporal basis functions of the raised cosine type with coefficients to be estimated (Pillow, J. W. et al., 2008 Nature 454, 995-999). Ten and four basis functions were used for the intrinsic and ensemble history filters, respectively. Thus, $K_{1,i}$ and $K_{2,i,j}$ in equation (2) consisted of nonparametric temporal filters for the intrinsic and ensemble spiking histories, respectively. Consistent with known neurophysiology and measured autocorrelation functions of the recorded spike trains, an absolute refractory period of 2 ms was enforced in the intrinsic history component. A history model for a particular neuron did not include the spiking history of other neurons recorded by the same electrode. That was done to avoid potential negative correlation artifacts, especially at zero and short time lags, commonly introduced by current spike thresholding and sorting algorithms. This rule was also adopted in the computation of the distribution of pair-wise correlation coefficients. Model parameters were estimated via gradient-ascent maximization of the penalized log-likelihood functions (Truccolo, W. Stochastic point process models for multivariate neuronal spike train data: collective dynamics and neural decoding. in Analysis of Parallel Spike Trains, eds Grün, S. and Rotter, S., Springer, New York, 2009). A regularization term in the form of a ridge regression penalty was added for the model parameters related to the ensemble history effects. After estimating a conditional intensity function model, the probability of a given neuron spiking at any given 1-ms time bin, conditioned on past spiking histories, was obtained (Truccolo, W. et al., 2005 J. Neurophysiol. 93, 1074-1089) as in equation (1)

$$Pr(x_{i,t}=1|H_t) = \lambda_i(t|H_t)\Delta + o(\Delta) \approx \lambda_i(t|H_t)\Delta$$

The term o(Δ) relates to the probability of observing more than one spike in a 1-ms time interval.

Example 4. Instantaneous Collective States: Point Process Models

The total interdependence in multivariate stochastic processes can be decomposed into two main components: a time 'causal' component (that is, the statistical dependence of current states on past events) and an instantaneous component (for example, instantaneous dependencies among neurons) (Geweke, J., 1982 J. Am. Stat. Assoc. 77, 304-314). Instantaneity at two time resolutions was considered: 1- and 10-ms time bins. When using the 10-ms resolution, the rare cases of time bins with more than one spike were represented as 1-spike events. Statistical interdependencies was estimated in these instantaneous collective states by first fitting zero time-lag pair-wise maximum entropy distribution models (Schneidman, E. et al., 2006 Nature 440, 1007-1012; Jaynes, E. T., 1982 Proc. IEEE 70. 939-952). Estimation of probability distributions for high-dimensional systems without further constraints is typically an intractable problem. On the other hand, second-order statistics in the faun of pair-wise correlations are still feasible to compute and maximum entropy distributions constrained on pair-wise correlations can then be estimated. This maximum entropy distribution model constrained on mean rates and pair-wise zero time-lag correlations (Schneidman, E. et al., 2006 Nature 440, 1007-101; Cover, T. M. et al., 1991 Elements of Information Theory, Wiley and Sons, New York) is given by $$Pr(x_{1,t}, x_{2,t}, \ldots, x_{n,t}) = \frac{1}{Z_{(\alpha,\beta)}} \exp\left\{\sum_i \alpha_i x_{i,t} + \frac{1}{2} \sum_{i \neq j} \beta_{i,j} x_{i,t} x_{j,t}\right\}$$

equation (6)

where $x_{i,t} \in \{-1, 1\}$, corresponding to no spike and spike, respectively, $Z_{(\alpha,\beta)}$ is a normalization constant, $\{\alpha_i\}$ reflects constraints imposed by the empirical mean spiking rates, and $\{\beta_{ij}\}$ reflects constraints imposed by the zero time-lag pair-wise correlations, with $\beta_{ij} = \beta_{ji}$. The conditional spiking probability of a given neuron under this pair-wise maximum entropy distribution model is given by $$Pr(x_{i,t} = 1 \mid x_{\setminus i, t}) = \frac{1}{2} \frac{\exp\left\{\alpha_i + \sum_{j \neq i} \beta_{i,j} x_{j,t}\right\}}{\exp\left\{\alpha_i + \sum_{j \neq i} \beta_{i,j} x_{j,t}\right\} + \exp\left\{-\alpha_i - \sum_{j \neq i} \beta_{i,j} x_{j,t}\right\}},$$

equation (7)

where $x_{\setminus i,t}$ denotes the observed neuronal ensemble state not including the $i^{th}$ neuron. Parameters of these pair-wise maximum entropy models were estimated via maximum pseudo-likelihood (Besag, J., 1975 *Statistician* 24, 179-195). The consistency of this estimator has been previously demonstrated, as has its relationship to contrastive divergence methods (Geman, S. et al., 1986 Proc. Int. Congr. Math. 1496-1517; Gidas, B. Consistency of maximum likelihood and pseudo-likelihood estimators for Gibbsian distributions in Stochastic Differential Systems, Stochastic Control Theory and Applications, eds Fleming, W. and Lions, P.-L. Springer, New York, 1988; Hyvärinen, A., 2006 Neural Comput. 18, 2283-2292). Gibbs sampling was used to sample from the estimated maximum entropy models and compute the distributions of multiple-neuron spike coincidences in 1- and 10-ms time bins (Geman, S. et al., 1984 IEEE Trans. Pattern Anal. Mach. Intell. 6, 721-741). For practical reasons, and in contrast with the ensemble history point process models, the data used to fit the maximum entropy distribution models also included neurons isolated in the same recording channel. This could have, if anything, helped to improve the performance of these maximum entropy models in comparison with the ensemble history models.

Example 5. ROC Analysis

ROC curves are a standard tool for the analysis of prediction performance (Fawcett, T., 2006 Pattern Recognit. Lett. 27, 861-874). After estimating a conditional intensity function model on training data, the probability of a given neuron spiking at any given 1-ms time bin, conditioned on either past spiking histories or instantaneous states, was computed on test data according to equations (3) and (5), respectively. A tenfold-crossvalidation scheme was used. From this probability, true- and false-positive prediction rates were computed, resulting in the ROC curves. The AUC was used to derive a predictive power measure. Informally, the relationship between AUC and predictive power can be expressed as follows. Consider the case where all of the 1-ms time bin samples are separated into two populations, one consisting of samples with a spike and the other consisting of samples with no spikes. Next, consider randomly drawing two samples, one from each population. The AUC gives the probability that our conditional intensity function model will assign a higher probability (that is, a higher instantaneous spiking rate) to the sample from the spike population than to the sample from the no-spike population (Bamber, D., 1975 J. Math. Psychol, 12, 387-415). The AUC therefore provides an assessment of the discriminatory or predictive power for predictive variables under a given model. It also relates to the Wilcoxon-Mann-Whitney U statistics in the case of independent samples. Given the temporal dependencies in our data, the AUC was computed directly from the ROC curve and random permutation tests were used to establish the statistical significance of estimated values. Typical confidence intervals were extremely narrow overall. The ROC curve of a chance level predictor asymptotes the diagonal line, resulting in a AUC of 0.5. In our datasets, the AUC corresponding to chance prediction could be slightly larger than 0.5. A relative predictive power (RPP) is defined herein with respect to this chance level as in equation (3)

RPP=2×(AUC−AUC*), where AUC* is the AUC corresponding to a chance level predictor for a particular neuron and model, estimated by random permutation methods. The scaling by a factor of 2 is introduced so that the relative predictive power ranges fron 0 (no predictive power) to 1 (perfect prediction).

Example 6. Information Rates

An information rate was computed that estimates how much reduction in the uncertainty about whether or not a neuron will spike in any given time bin, conditioned on knowing only the mean spiking rate, is achieved by also knowing spiking histories and their estimated effects under a given history model. Given large enough number of samples and under an ergodicity assumption, this information rate can be approximated (Cover, T. M. et al., Elements of Information Theory, Wiley and Sons, New York, 1991) as $$\frac{1}{T}\sum_{t=1}^{T} x_{i,t}\log(\lambda_i(t|H_t)\Delta) - \lambda_i(t|H_t)\Delta - (\overline{\lambda}_i\Delta\log(\overline{\lambda}_i\Delta) - \overline{\lambda}_i\Delta),$$ equation (8)

where $x_{i,t} \in \{0,1\}$, $\overline{\lambda}_i$ is the mean spiking rate and $\lambda_{i,t} = \lambda_i(t|H_e)$. The summation term corresponds to the average log-likelihood under the history model, with averages computed over T samples (1-ms time bins) and the second term corresponds to the average log-likelihood under a homogeneous Poisson process with the specified mean rate. Computed to base 2 and normalized by $\Delta$, the above quantity corresponds to an information rate in bits per second.

Example 7. Results from People with Tetraplegia, and Monkeys

Twelve neuronal datasets recorded from two human clinical trial participants with tetraplegia (hS1 and hS3) and four monkeys (mLA, mCL, mCO and mAB) were analyzed. These included M1 recordings taken while human participants performed two sessions of a 'neural cursor' center-out task (that is, a task where the participant used, via a neural interface, his or her own recorded M1 spiking activity to move a computer cursor to targets radially positioned on the computer screen), M1 recordings from two monkeys (mLA and mCL), each performing two sessions of a task requiring planar point-to-point reaches toward targets randomly placed in the workspace, simultaneous M1 and PMv recordings from a monkey (mCO) performing two sessions of a task that required reach and grasp toward moving objects in a three-dimensional workspace, and simultaneous M1 and 5d recordings from a monkey (mAB) performing two sessions of a pursuit tracking task that required planar hand movements. The 12 datasets used in the analyses included 1,187 neuronal recordings Minimum inter-electrode distance in the 10×10 microelectrode array was 400 μm. Maximum inter-electrode distance, including electrodes in two arrays, was approximately 2 cm (FIG. 1).

Figure 2:
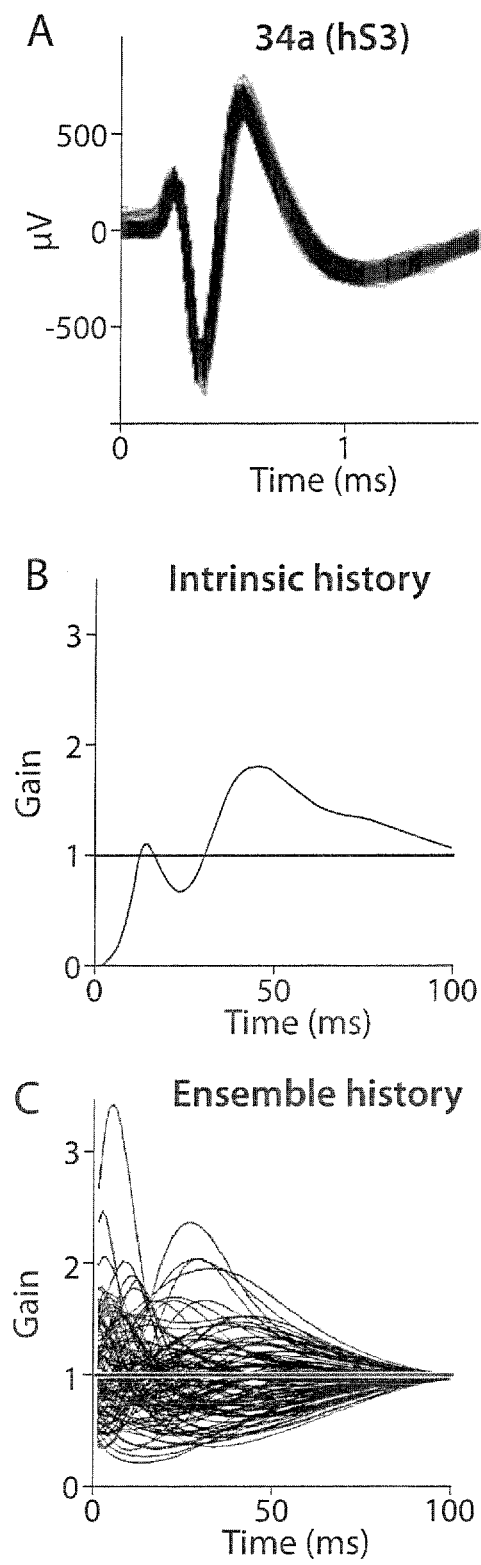
FIG. 2 is a set of graphs showing history point process models, intrinsic and ensemble history effects, and conditional spiking probabilities. Neuron 34a (hS3, session 2) was chosen as the example target neuron.
Figure 2:
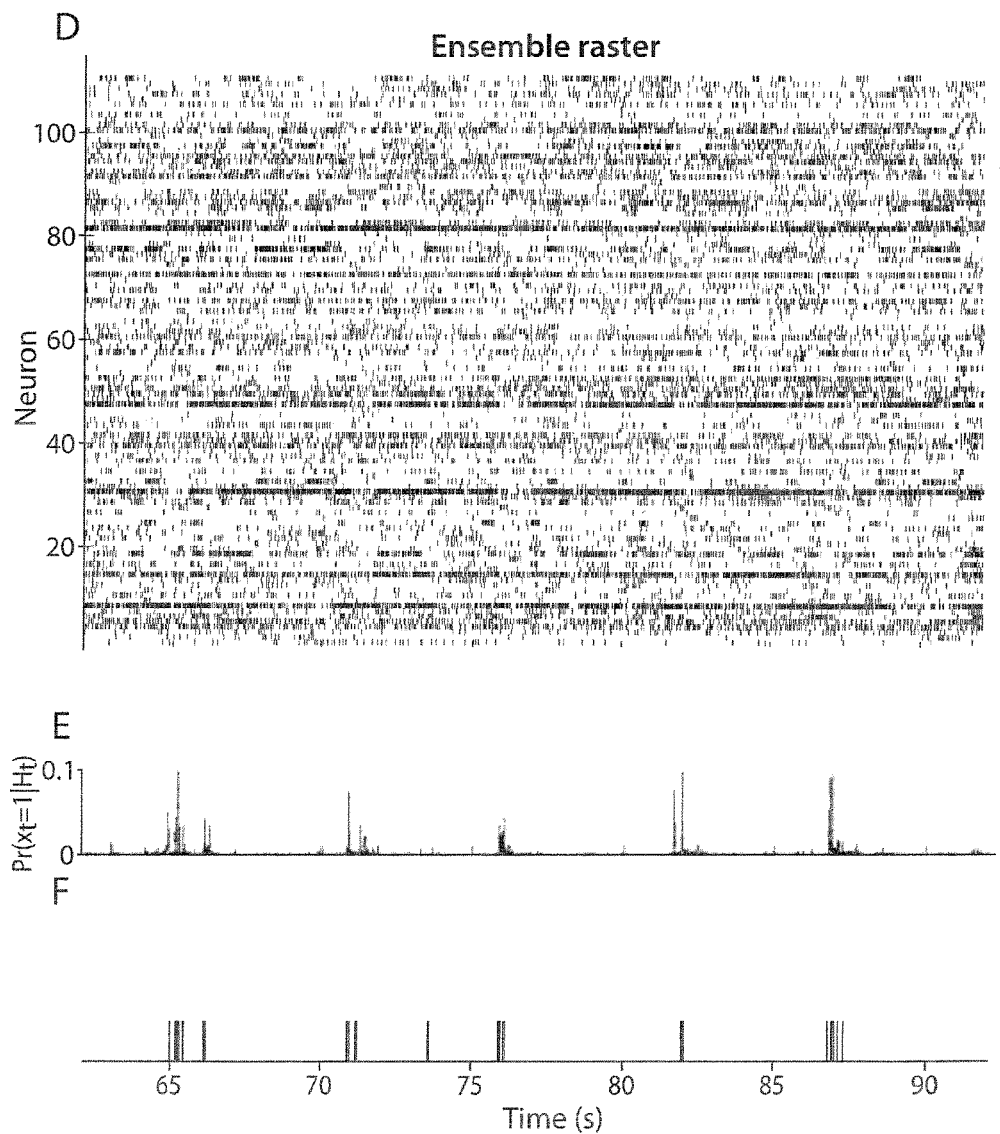

To assess the predictive power of spiking histories, we first computed the probability that any given $i^{th}$ neuron $x_{i,t}$ was going to spike at time t, conditioned on spiking histories $H_t$ from the past 100 ms up to (but not including) time t. Without further constraints, direct estimation of conditional probability distributions for high-dimensional systems is typically an intractable problem, leading to combinatorial explosion and requiring amounts of data that grow exponentially with the number of neurons in the ensemble. Instead, advantage was taken of the fact that this conditional probability can be computed (Truccolo, W. et al., 2005 J. Neurophysiol. 93, 1074-1089) according to $$Pr(x_{i,t}=1|H_t) \approx \lambda_i(t|H_t)\Delta$$

where $\lambda_i(t|H_t)$ is the instantaneous spiking rate (conditional intensity function) of the neuron and $\Delta=1$ ms in our discrete time representation, and used a simplified model to capture the relationship between the instantaneous rate and spiking histories $$\log(\lambda_i(t|H_t)\Delta) = \mu_i + K_{1,i} * x_i + \sum_{j \neq i} K_{2,i,j} * x_j$$

where the term $\mu_i$ relates to a background level of spiking activity, $x_i$ is the spiking history in the specified time interval for the $i^{th}$ neuron, i=1, 2, ..., n recorded neurons, and $k_{1,i}$ and $K_{2,i,j}$ denote temporal filters related to intrinsic and ensemble history effects, respectively. These temporal filters were approximated via basis functions (see Pillow, J. W. et al., 2008 Nature 454, 995-999; Truccolo, W. et al., 2005 J. Neurophysiol. 93, 1074-1089; Truccolo, W. Stochastic point process models for multivariate neuronal spike train data: collective dynamics and neural decoding. In Analysis of Parallel Spike Trains, eds Grün, S., Rotter, S., Springer, New York, 2009, and Examples herein). Once an instantaneous spiking rate model was fitted, the estimated probability of a spike at any given time bin, conditioned on intrinsic and ensemble spiking histories, was easily computed using equation (3) (the spike prediction approach is shown using cell 34a (hS3) as the example target neuron; FIG. 2).

Example 8. Predictive Power of Ensemble Spiking Histories in M1

Figure 3:
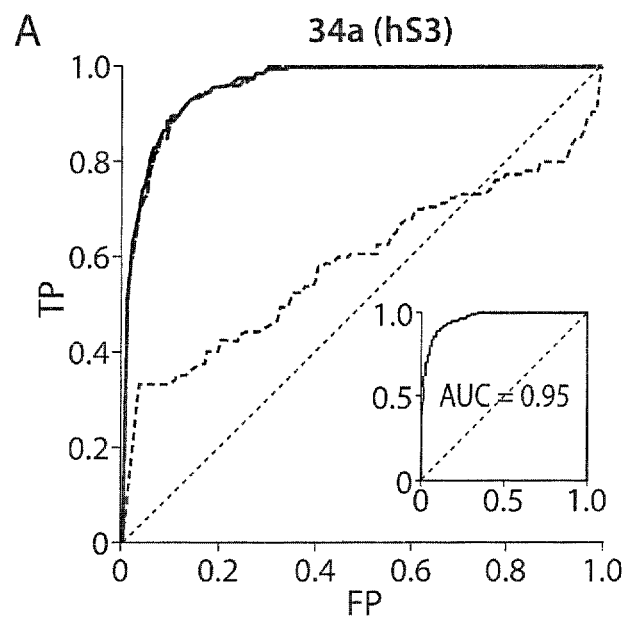
FIG. 3 is a set of graphs showing prediction of single-neuron spiking and weak pair-wise correlations.
Figure 3:
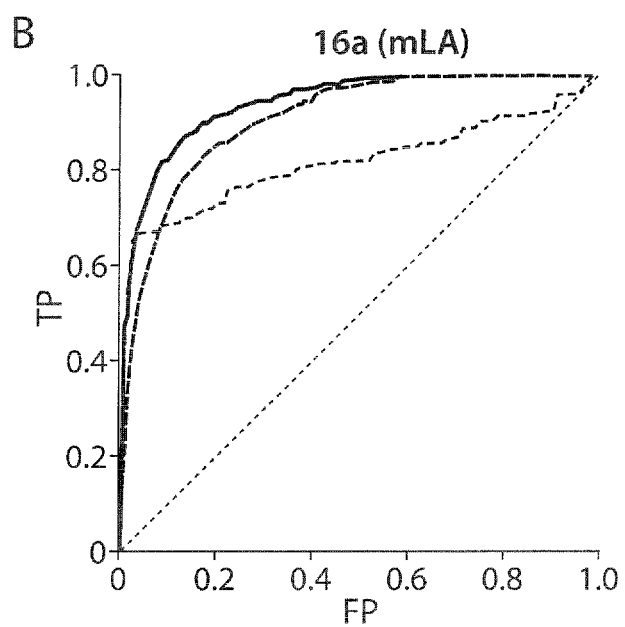
Figure 3:
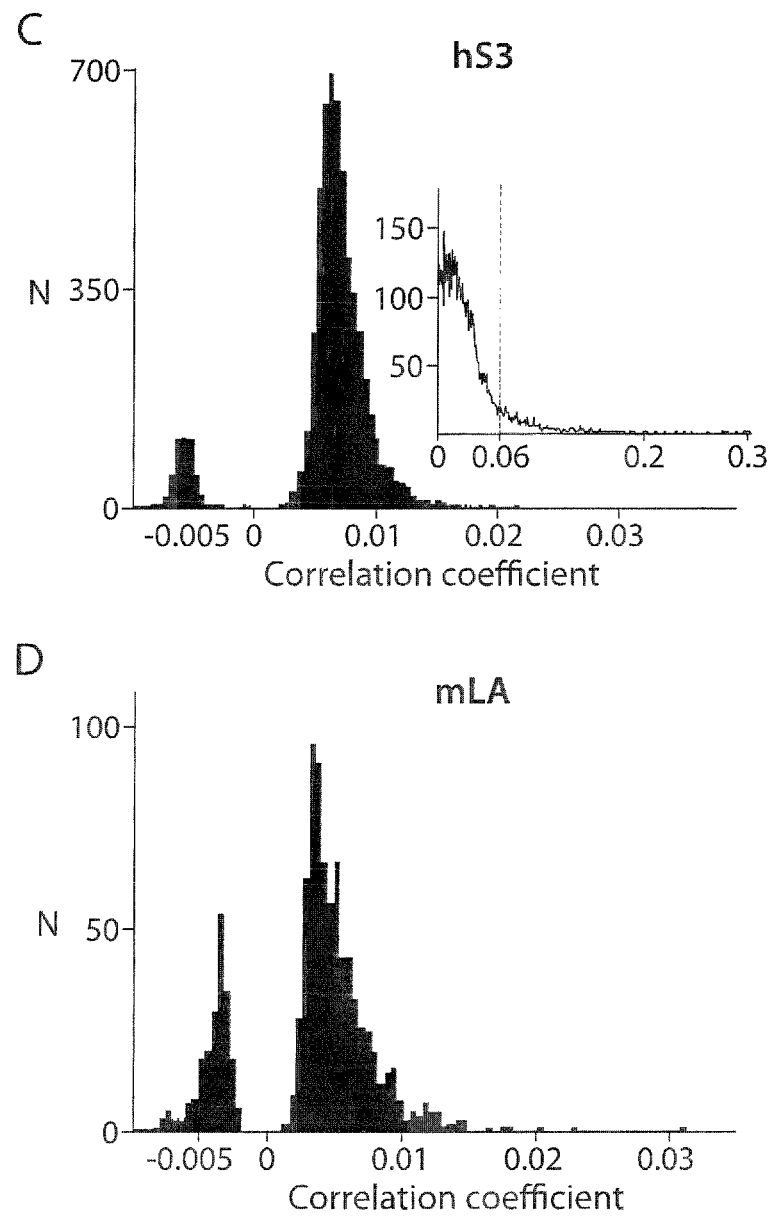

On the basis of the estimated conditional spiking probabilities, a standard tool, the ROC curve analysis, was used to assess the predictive power of spiking history models (see Fawcett, T., 2006 Pattern Recognit. Lett. 27, 861-874 and Examples herein). Spike prediction in 1-ms time bins based on spiking histories was substantial. Intra-areal ensemble history—based predictions in M1 resulted in high true-positive rates while maintaining low numbers of false positives. For example, it was possible to correctly predict 80% of spikes in neuron 34a (participant hS3) with a false-positive rate of less than 5% (FIG. 3 panel A). Similarly, an 80% true-positive rate was obtained for neuron 16a (monkey mLA) with a less than 10% false-positive rate (FIG. 3 panel B). This predictability was substantial despite the weak pair-wise correlations that were observed among all neuronal pairs in the recorded datasets for hS3 and mLA (FIG. 3 panels C and D). This observation was confirmed in datasets for subjects, areas and tasks.

Figure 4:
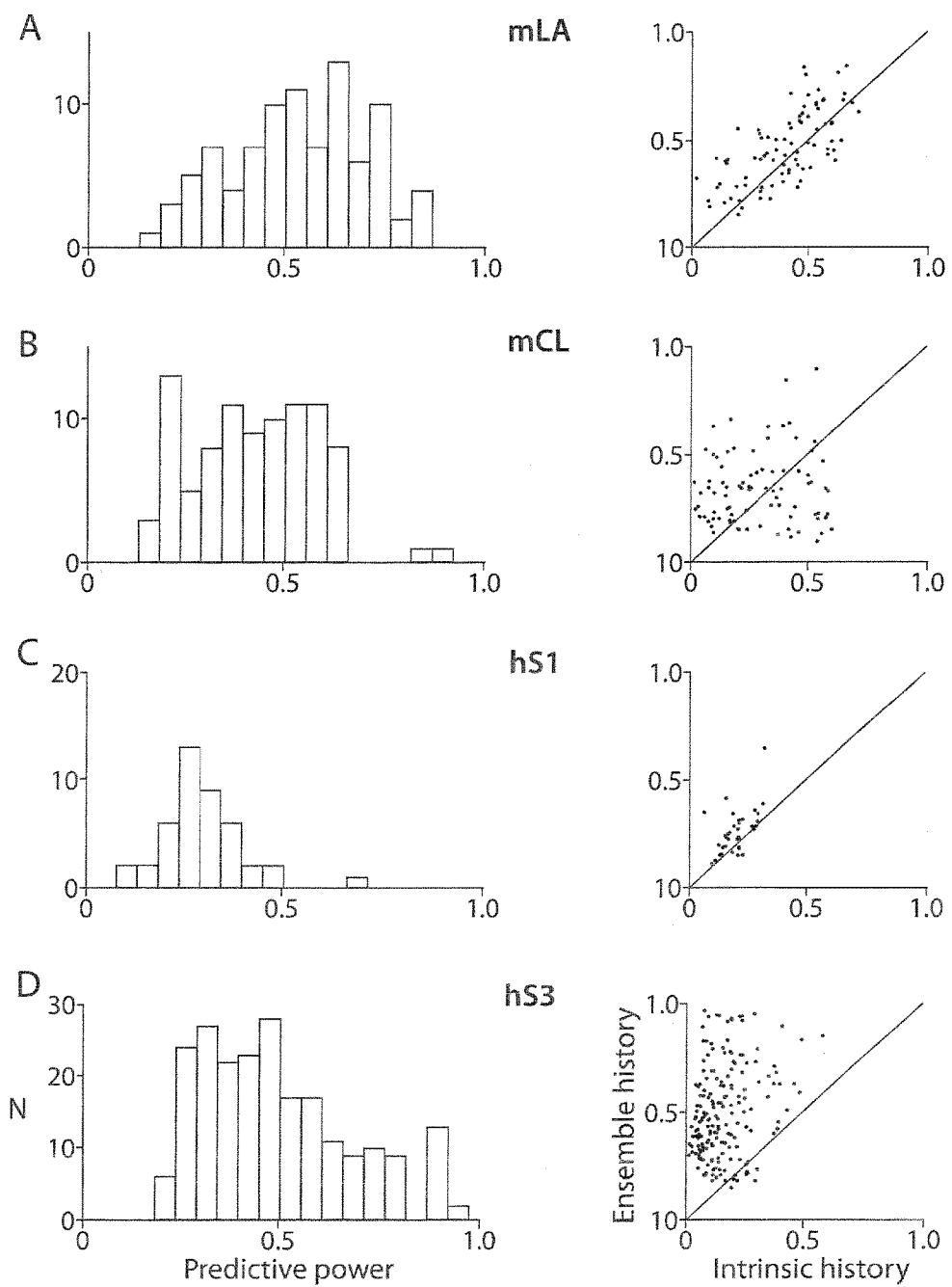
FIG. 4 is a set of bar graphs and distribution plots showing predictive power of intra-areal (M1) ensemble histories.
Figure 5:
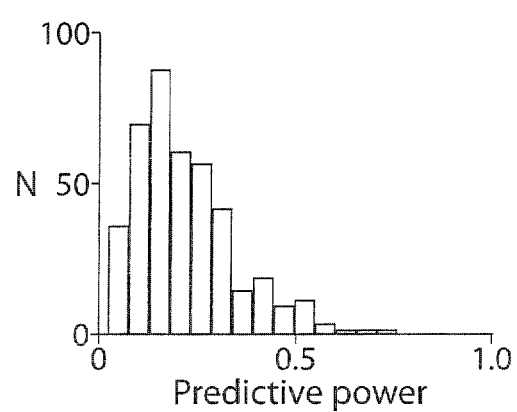
FIG. 5 is a bar graph showing distribution of M1 (Intra-areal) ensemble predictive power: random ensemble subsets of size n=22 (hS3, session 2).

A more comprehensive assessment of predictive performance was obtained by computing the area under the ROC curve. The area under the curve (AUC) is a global summary statistic; that is, it depends on both the true- and false-positive rates and on all of the possible thresholds on the spiking probability. The AUC gives the probability that, when two samples are randomly drawn from the data (one containing a spike, the other not), the conditional intensity model will assign a higher probability (i.e. a higher instantaneous spiking rate) to the sample with a spike (Bamber, D., 1975 J. Math. Psychol. 12, 387-415). It therefore provides an assessment of the discriminatory power for predictive variables under a given model. It approaches 0.5 for a chance level predictor, that is, a predictor having false- and true-positive rates along the diagonal, and it equals 1 for a perfect predictor. For example, the AUC for neuron 34a was 0.95 (FIG. 3 panel A). The AUC was further corrected by subtracting chance-level predictions estimated from the actual data and scaled it to obtain a quantity that ranged from 0 (no predictive power) to 1 (perfect prediction). This corrected and normalized AUC measure was referred to as the predictive power (see Examples). More than 50% of examined neurons in monkey mLA showed a predictive power higher than 0.5 (median=0.55, range=0.1-0.89) (FIG. 4). Prediction in subjects mCL and hS3 showed similar performances, with medians of 0.45 and 0.49 and ranges of 0.18-0.91 and 0.23-0.97, respectively. Predictive power was lower for participant hS1 (median=0.30, range=014-0.69). Conjectured was made that this was probably a result of the smaller number of neurons (n=21, n=22) that were recorded and used for prediction in this participant. To test this conjecture, the predictive power was computed on the basis of several smaller ensemble subsets (n=22 neurons) randomly chosen out of the 110 neurons from hS3's dataset (session 2). Data from hS3 provided a good reference, as neurons were recorded from M1 under the same task condition as for hS1. The distribution of predictive power values, based on this collection of smaller ensemble subsets, was similar to the one obtained for hS1, supporting hypothesis (FIG. 5).

These predictive power levels were obtained using the full history models, that is, the instantaneous spiking rate of each neuron conditioned on both intrinsic and ensemble histories. The predictive power of each of these two components separately was further assessed (FIG. 4). For the majority of neurons in all of the subjects, the predictive power obtained exclusively from the ensemble histories was larger than the predictive power from intrinsic histories. In addition, it is possible that some of the intrinsic history effects, beyond refractory and recovery period effects, could also reflect network dynamics. Thus, these results indicate that the collective ensemble activity, rather than refractory and recovery dynamics, was the main source of the observed predictive power of spiking histories.

Figure 6:
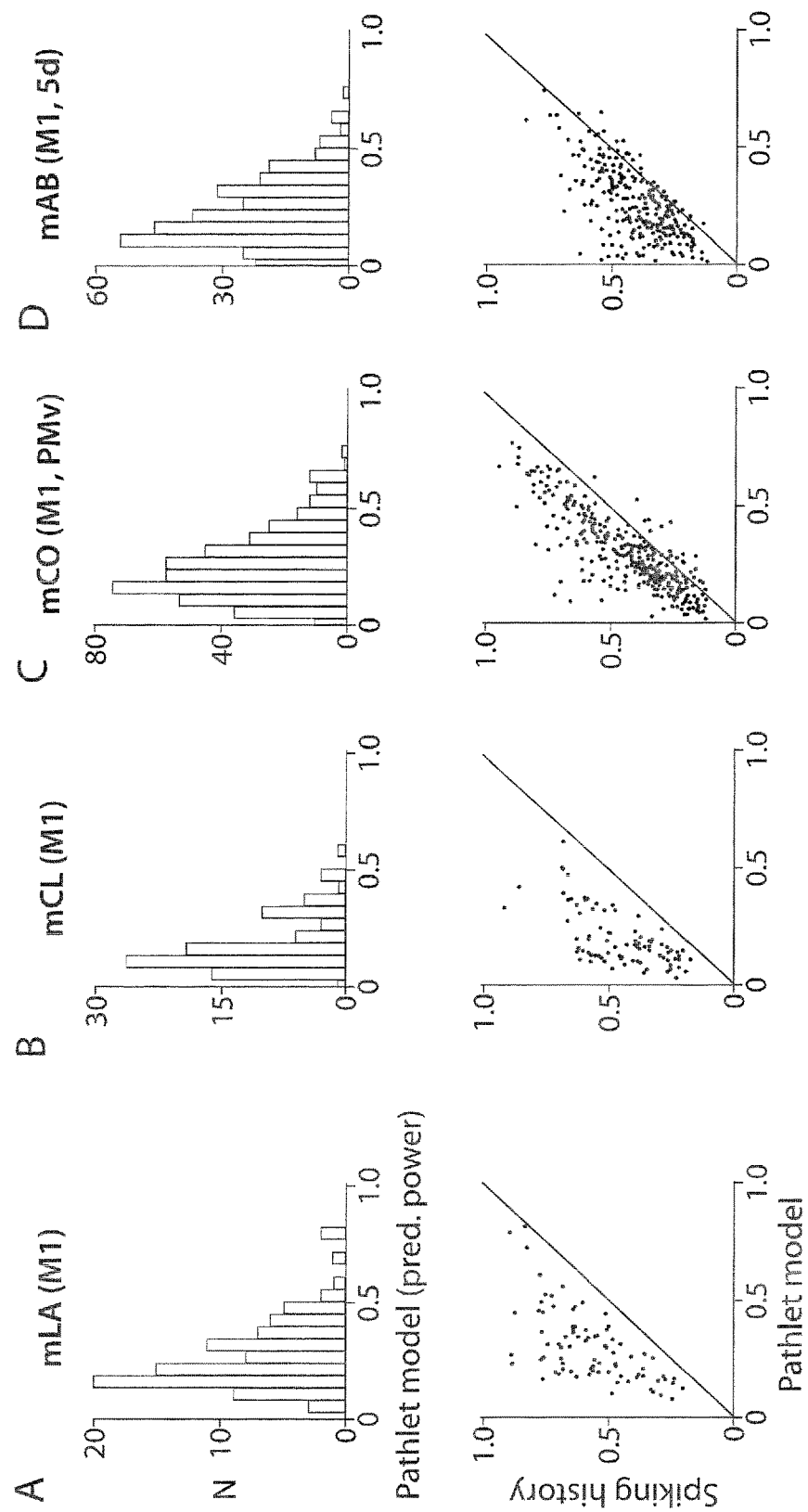
FIG. 6 is a set of histograms and distribution plots showing predictive power of spiking history models versus pathlet models. Top row shows the distributions of predictive power computed from the pathlet models for each of the four monkeys. The second row shows the predictive power of spiking history models versus the predictive power of pathlet models.
Figure 7:
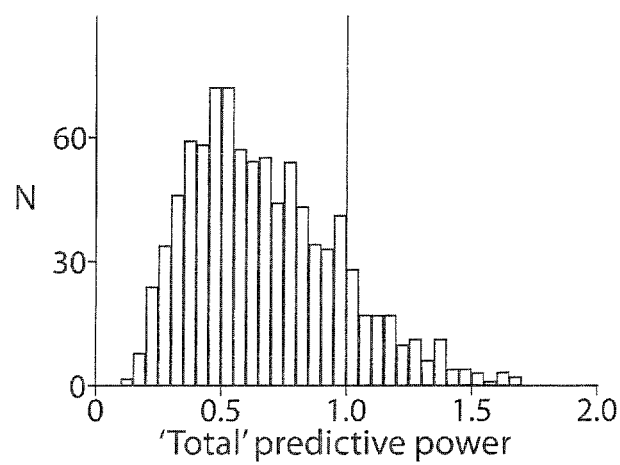
FIG. 7 shows histograms of the 'total' predictive power of ensemble spiking history and pathlet models. Here, 'total' predictive power refers to the sum of the predictive power of the spiking history model and the power of the pathlet model, computed for each neuron (n=924 neurons; datasets mLA, mCL, mCO and mAB). This 'total' predictive power should add up to at most 1 (perfect prediction) if there was no redundancy between the information conveyed by ensemble history models and the information conveyed by pathlet models.

The predictive power of these M1 spiking history models in monkeys mLA and mCL was also higher than the predictive power of relevant kinematic covariates, such as hand position and velocity (FIG. 6 and examples). Pathlet models was used to estimate spiking probabilities conditioned on kinematics; that is, the instantaneous spiking rate was expressed as function of hand position and velocity trajectory in the time (approximately 200 ms, 300 ms) with respect to spiking time (Hatsopoulos, N. G. et al., 2007 J. Neurosci. 27, 5105-5114). Furthermore, the predictive power values of spiking history and pathlet models were not strictly additive (FIG. 7). This result indicates that there was some level of redundancy between the information conveyed by these two models about single-neuron spiking: some of the spiking activity that was predicted by the spiking history models could also be predicted by the examined kinematics.

Example 9. Predictive Power and Ensemble Size in M1

Conjecture was made that the smaller size of the M1 neuronal ensemble for participant hS1(n=21, n=22) explained the lower predictive power obtained for this participant in comparison to hS3, mLA and mCL (FIG. 4). To further investigate this possibility, subsets of 22 neurons out of the 110 neuron ensemble from participant hS3 (session 2) were randomly sampled. Data from hS3 provided a good reference since these neurons were recorded from M1 under the same task condition. Twenty of these random subsets, each of size n=22, were sampled. Although these subsets were different, some of the neurons could be present in multiple subsets. In each random subset, conditional intensity functions for each neuron were modeled as a function of the intrinsic spiking history and the spiking histories of the other neurons in the random subset. Predictive power of these history models for each target neuron was computed as in Examples herein. FIG. 5 shows the distribution of predictive power for all of the neurons in these 20 random subsets. This distribution was similar to the one obtained for hS1, supporting our conjecture.

Example 10. Comparing the Predictive Power of Spiking History and Pathlet Models (Hand Position and Velocity Trajectories) in M1, PMv and 5d Neurons M1 neurons are known to be strongly modulated with hand position and velocity during reaching movements, as performed in the task executed by the monkeys in this study (Ashe et al., 1994 Cereb Cortex 4, 590-600; Moran et al., 2001 J. Neurophysiol. 82, 2676-2692). In particular, Hatsopoulos et al., 2007 J. Neirosci. 27, 5105-5114, and Paninski et al. 2004 J. Neurophysiol 91, 515-532, have shown that M1 neurons can be highly tuned to preferred trajectories in velocity space, that is, neurons are not only tuned to the instantaneous velocity at a particular single time lag, but are related to velocity trajectories spanning a short time period. This means that trajectories (histories) in velocity space can also predict single neuron spikes and could potentially account for the same predictive power observed for the ensemble history. The predictive power of recent spiking history was compared to the predictive power of hand position and velocity trajectories. 'Pathlet' models (Hatsopoulos et al., J Neurosci 27, 5105-5114, 2007) were used to express the instantaneous spiking rate at time t as a function of the instantaneous hand position and velocities over the time interval [−200, 300] ms around neuron time t. Specifically, this 'pathlet' conditional intensity model was obtained from $$\log[\lambda_i(t \mid p_{1,t+\tau}, p_{2,t+\tau}, v_{1,t+\tau_1:t+\tau_2}, v_{2,t+\tau_1:t+\tau_2})\Delta] =$$
$$\mu_i + a_i p_{1,t+\tau} + b_i p_{2,t+\tau} + \sum_{k \in \{-4,-1,\ldots,6\}} c_{i,k} v_{1,t+k\delta} + d_{i,k} v_{2,t+k\delta}$$

where $p_{1,t+\tau}$, and $p_{2,t+\tau}$ are the positions in the horizontal and vertical coordinates at a preferred time lag t+τ(depending on the neuron), $v_{1,t+\tau_1:t+\tau_2}$ and $v_{2,t+\tau_1:t+\tau_2}$ correspond to the velocities over the time interval=$\tau_1$=−200, $\tau_2$=300] ms, sampled at δ=50 ms time steps; (pathlet models for mCO included position and velocity in 3 dimensions); a,b,c and d are tuning parameters estimated via maximum likelihood methods (Truccolo et al., 2005 J. Neurophysiol. 93, 1074-1089). The choice of the above time interval was based on the study in Hatsopoulos et al., 2007 J. Neurosci. 27, 5105-5114, and on exploration of different intervals in our own data; use of larger time intervals did not significantly improve prediction performance. FIG. 6 (top row) shows the distributions of predictive power values based on these pathlet models for neurons recorded from the four monkeys. The predictive power of full history models was typically higher than the predictive power of pathlet models.

The issue of redundancy between the information conveyed by spiking histories and information conveyed pathlet models was also examined (FIG. 7). The following points summarize analysis of this redundancy.

If there was no redundancy in the information conveyed by these two models, the predictive powers of a history model and of a pathlet model for a given neuron should add to at most 1, the maximum possible value corresponding to perfect prediction. By contrast, the predictive powers of these two individual models were not strictly additive, i.e. they could add up to values greater than 1, indicating that some of the same spiking activity predicted by the spiking history models could also be predicted by the examined kinematics (FIG. 7).

This redundancy was also present for neurons whose summed predictive powers of spiking history and pathlet models added up to a value smaller than 1. The predictive power of a combined model (i.e. a model that included both spiking histories and kinematics) was significantly smaller than the sum of the predictive power of the two individual models for the majority of neurons (>80% of neurons in the 3 studied cortical areas).

Despite the redundancy between the information conveyed by these two models as implied in the points supra, there was also extra information about single neuron spiking in the spiking history that could not be accounted for by the examined kinematics. This follows from the fact that predictive power was typically higher for spiking history models as seen in FIG. 6.

Example 11. Predictive Power of M1 Instantaneous Collective States

Beyond examining the predictive power of ensemble spiking histories, the predictive power of instantaneous collective states in the recorded ensemble was also assessed, that is, simultaneous states at either 1- or 10-ms temporal resolution. Instantaneously correlated states could result from common inputs and/or from synchronization patterns arising from the neuronal network's own dynamics Strong instantaneous collective states could still be consistent with the weak pair-wise instantaneous interactions that was observed in datasets shown in FIG. 3 (Schneidman, E. et al., 2006 Nature 440, 1007-1012). The joint probability distribution of these instantaneous collective states was estimated by fitting maximum entropy point process models constrained by empirical mean spiking rates and zero time-lag pair-wise correlations (Jaynes, E. T., 1982 Proc. IEEE 70, 939-952; Cover, T. M. et al., Elements of Information Theory, Wiley and Sons, New York, 199). That is, these maximum entropy distribution models were consistent with the observed mean spiking rates and zero time-lag pair-wise correlations, but made no additional assumptions (see Examples). This pair-wise maximum entropy probability model, also known as the Ising model in statistical mechanics (Landau, L. D. et al., Statistical Physics 3rd edn, Butterworth & Heinemann, Oxford, 1980; Amit, D. J. Modeling Brain Function Cambridge University Press, Cambridge, 1989), has been shown to capture most of the instantaneous interdependency structure in ex vivo/in vitro neuronal ensemble preparations (Schneidman, E. et al., 2006 Nature 440, 1007-1012; Shlens, J. et al., 2006 J. Neurosci. 26, 8254-8266; Yu, S. et al., 2008 Cereb. Cortex 18, 2891-2901).

Figure 8:
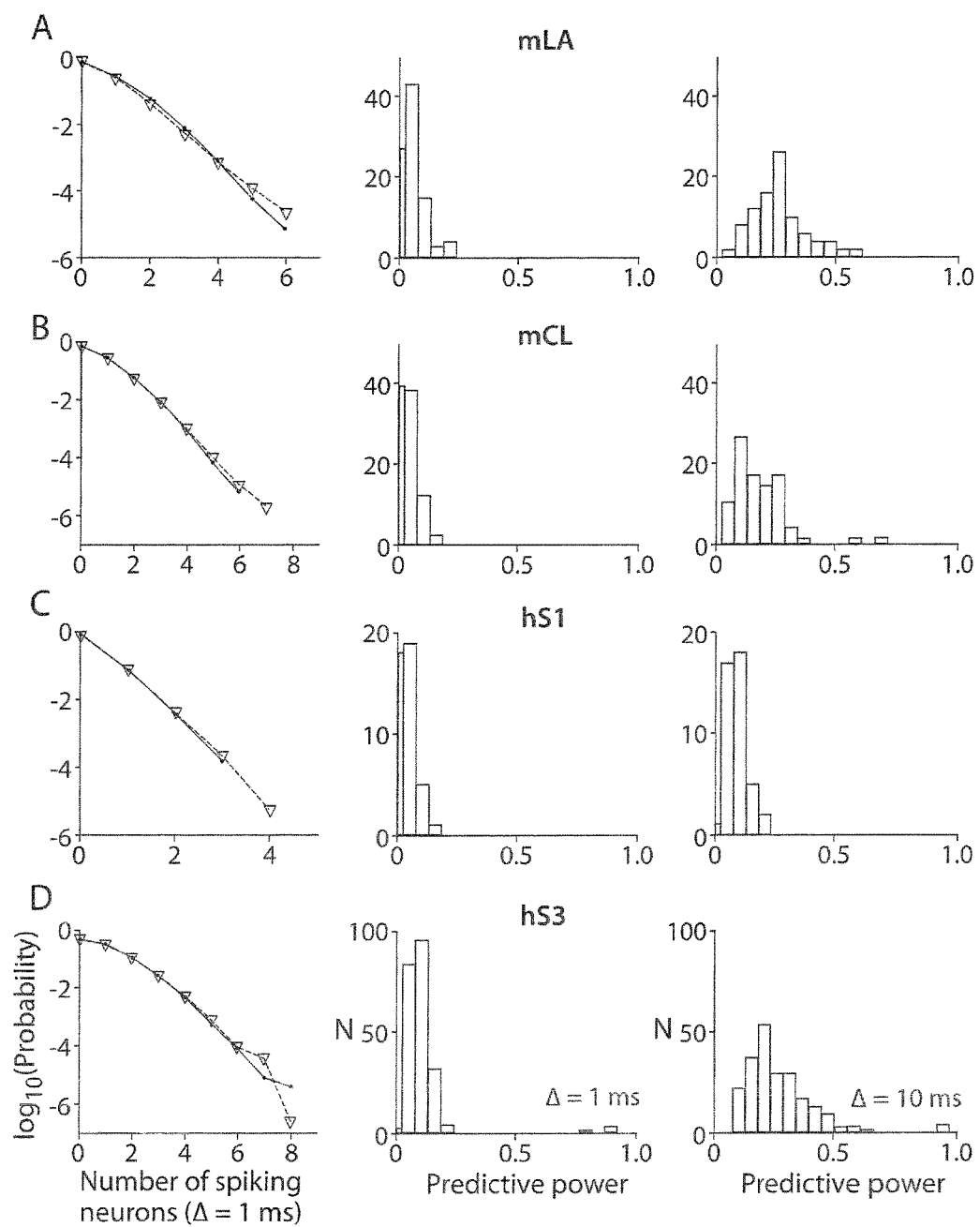
FIG. 8 is a set of line graphs and bar graphs showing predictive power of instantaneous collective states (Ising models).

Besides satisfying the pair-wise correlation structure in the examined datasets, the estimated models also accounted well for the distribution of multiple-neuron spike coincidences, as seen in the comparison of the empirical distribution and the distribution generated from the model via. Gibbs sampling (FIG. 8; Geman, S. et al., 1984 IEEE Trans. Pattern Anal. Mach. Intell. 6, 721-741). Nevertheless, the predictive power of this pair-wise correlation structure was considerably poorer than the predictive power of intrinsic and ensemble spiking histories, as captured by the models (FIG. 8). Across the four subjects, the predictive power values of pair-wise maximum entropy models corresponded to 0.10±0.17, while the spiking history models yielded values of 0.50±0.40 (mean±s.d.). The predictive power of spiking history models were still higher when instantaneous states at a coarser 10-ms temporal resolution was considered (FIG. 8), which resulted in predictive power values of 0.26±0.27 (mean±s.d.).

Example 12. Intra and Inter-Areal Spike Prediction: M1↔PMv and M1↔5d

Figure 9:
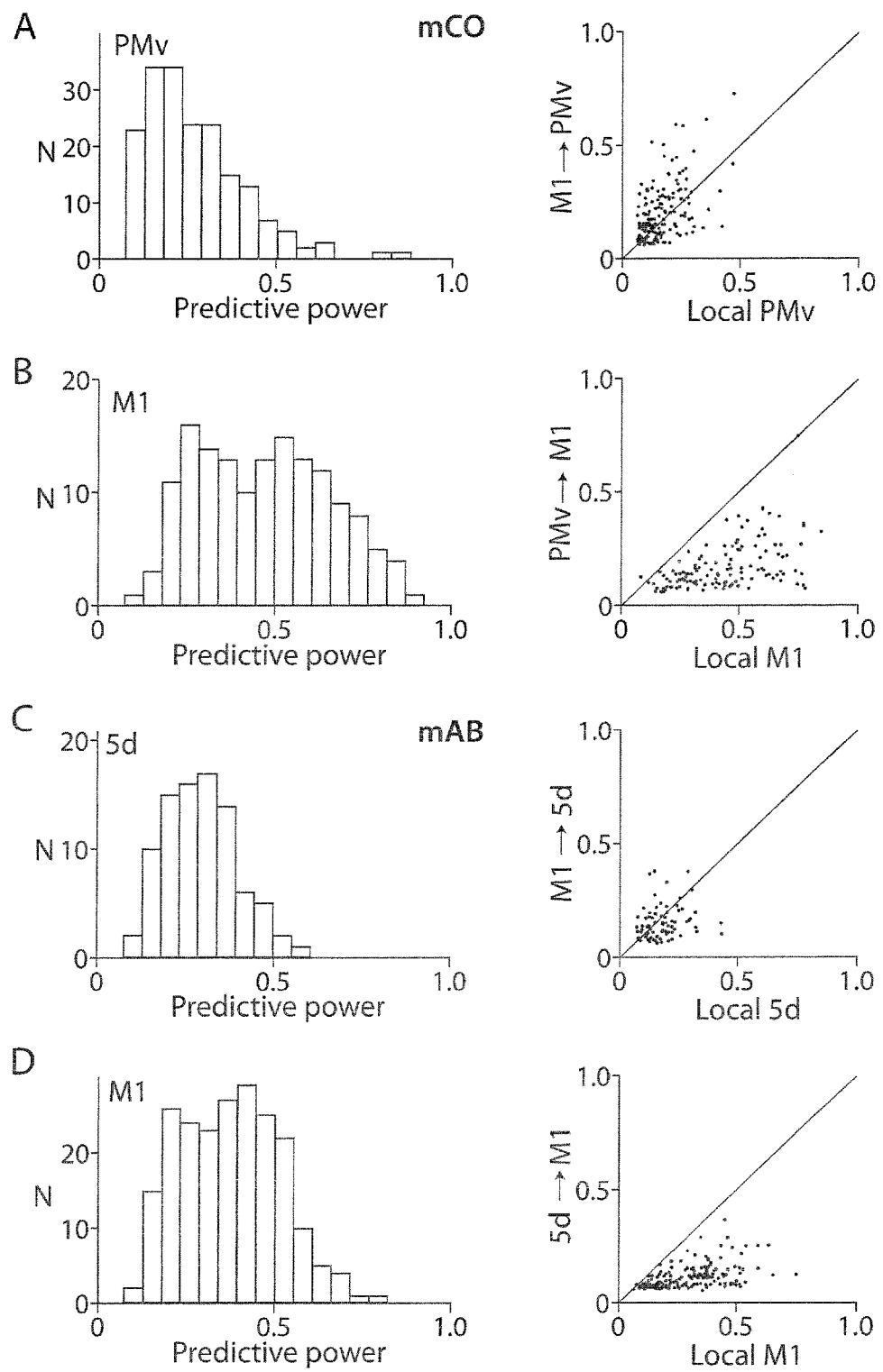
FIG. 9 is a set of line graphs and distribution plots showing predictive power of intra- and inter-areal neuronal ensemble histories. Predictive power of inter-areal ensemble history was also substantial.

The same predictive power analysis was performed for areas PMv and 5d and compared predictions based on ensemble histories recorded from the same or a different cortical area in the connected pairs M1↔PMv and M1↔5d (FIG. 9). Predictive power, based on both local and inter-areal spiking histories, corresponding to target neurons in PMv (mCO; FIG. 9 panel A) and 5d (mAB; FIG. 9 panel C) had medians of 0.27 and 0.32 and ranges of 0.110.86 and 0.130.62, respectively. Predictive power corresponding to target neurons in M1, based on both local and inter-areal spiking histories, had medians of 0.50 and 0.40 and ranges of 0.15-0.93 and 0.11-0.83 for monkeys mCO and mAB, respectively (FIG. 9 panels B and D). The inter-areal predictive power could also be substantial in both directions, M1↔PMv and M1↔5d (FIG. 9). Medians were 0.15, 0.13, 0.13 and 0.09 and ranges were 0.05-0.73, 0.06-0.75, 0.06-0.37 and 0.05-0.37 for M1→PMv, PMv→M1, M1→5d and 5d→M1, respectively.

Figure 10:
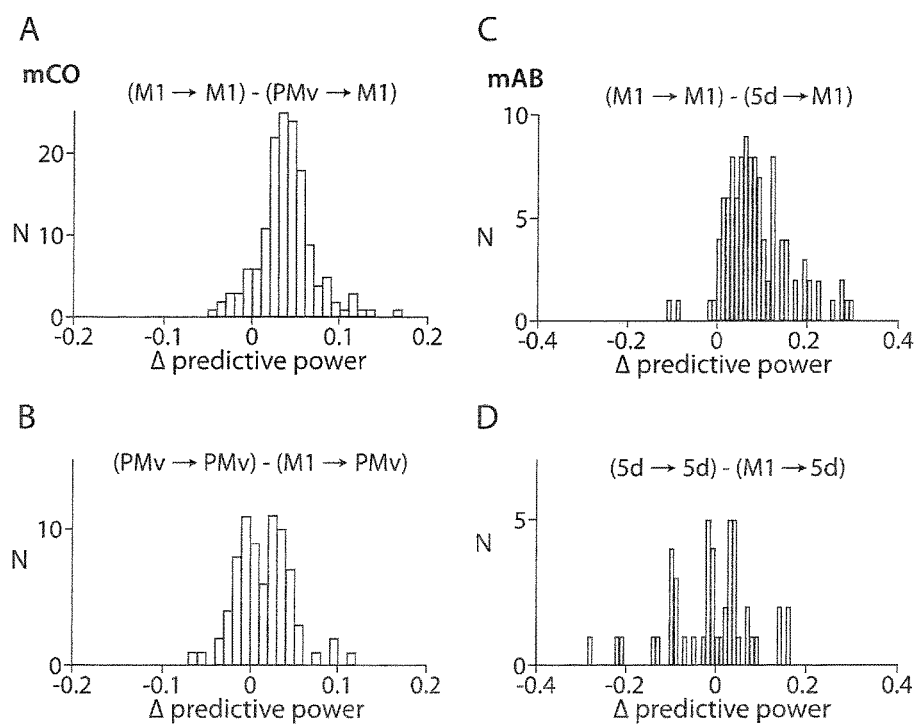
FIG. 10 is a set of histograms showing intra versus inter-areal predictive power for balanced-size ensembles.

Furthermore, the predictive power from one area to target neurons in the other, especially from M1→PMv, could be larger than the predictive power of local ensembles (FIG. 9 panels A and C). Without being limited to any particular theory or mechanism, the higher predictive power of M1↔PMv in some of these cases could simply reflect the larger number of recorded neurons in M1, rather than the relative strength of feedforward and feedback connections between these two areas. A supplementary analysis using ensembles of equal size showed that this was the case (FIG. 10 and examples). This analysis also indicated that intra-areal predictive power was slightly higher than inter-areal predictive power when ensembles of equal size were considered.

As shown before for subjects mLA and mCL, the predictive power of spiking history models for areas M1, 5d and PMv also tended to be higher than the predictive power of pathlet models (FIG. 6). The medians and ranges of predictive power values for pathlet models corresponded to 0.25 and 0.21, and 0.01-0.77 and 0.01-0.75 for mCO and mAB, respectively.

Example 13. Ensemble Size and Inter-Areal Predictive Power

Further, the possibility that the larger number of neurons in M1 ensembles could explain the higher predictive power of inter-areal predictive power, in comparison to the intra-areal predictive power, especially for the M1↔PMv effect in some of the examined target neurons was also investigated. To address this issue, new history models based on balanced-size ensembles were fitted, that is, the number of neurons in M1 and PMv ensembles (and in the M1 and 5d ensembles) were set to be equal. First, the number of neurons n in the ensembles was set for both areas to equal the number of neurons in the smallest ensemble of the cortical pair: in this case, the number of neurons in 5d for the M1↔5d pair, and PMv for the M1↔PMv pair. Second, for each neuron whose spiking was to be predicted, the input neurons were ranked according to their strength based on the magnitudes of the corresponding original model coefficients: i.e., the coefficients estimated based on the full history models shown in FIG. 9. Only the n top-ranked neurons were then included in the new balanced-size models. FIG. 10 shows the differences between intra and inter-areal predictive power for target neurons in M1, PMv and 5d. Differences between intra and inter-areal predictive power in these balance ensembles were small on average. Nevertheless, especially for M1, the distribution of these differences was skewed toward positive values, i.e. higher values for intra-areal predictive power.

Example 14. Predictability, Spiking Irregularity and Information Rates

Figure 11:
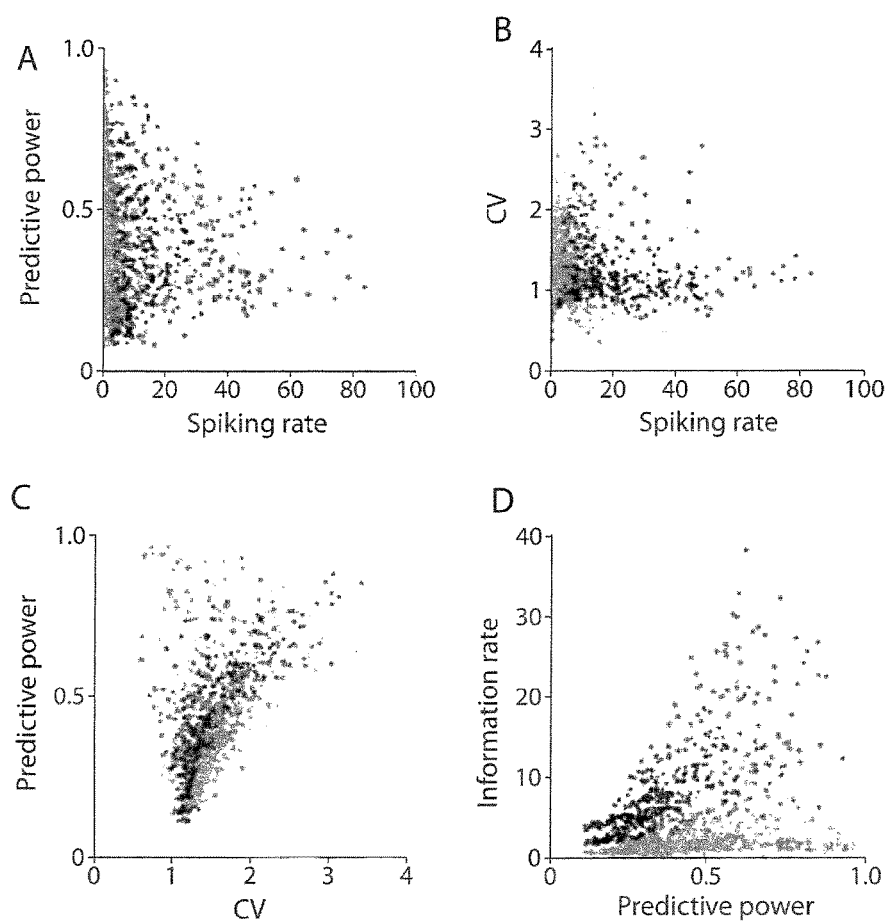
FIG. 11 is a set of distribution plots showing predictive power, mean spiking rates, spike train irregularity and information rates. Each dot corresponds to one of the 1,187 target neurons recorded from two human participants and four monkeys, three different cortical areas and four different tasks. Black and different shades of grey relate to one of the different tasks. Light grey: point-to-point reaching, monkeys mLA and mCL, area M1; darker shade of grey: neural cursor control, participants hS1 and hS3, area M1; black: free reach and grasp task, monkey mCO, areas M1 and PMv; dark grey: pursuit tracking task, monkey mAB, areas M1 and 5d.

The predictive power of spiking history models varied broadly across the 1,187 neurons in the 12 datasets. Whether this variation could be easily explained by simple features of the predicted spiking activity was examined. The predictive power of history models did not appear to depend, at least in a simple manner, on the mean spiking rate or on the level of irregularity of the predicted spiking activity (FIG. 11 panels A and C). Assessments of spike train irregularity were based on the coefficient of variation of the interspike time intervals (Dayan, P. et al., Theoretical Neuroscience, MIT Press, Cambridge, Mass., 2001). How much information was involved in the prediction of single neuron spiking was also assessed.

In principle, the same level of prediction accuracy could be achieved for two different target neurons while involving different amounts of information. This possibility was examined by asking how much information about a neuron spiking or not at any given time was gained by modeling the intrinsic and ensemble history effects compared with knowing only the mean spiking rate of the process. This information gain can be estimated as the normalized difference between the log-likelihood under the estimated history model and the log-likelihood under a homogenous Poisson process with given mean spiking rate (see Examples). Our analysis confirmed that similar predictive power values (in the prediction of different target neurons) could involve a wide range of information rates (FIG. 11 panel D).

Data herein show that single-neuron spiking in the cortex of humans and monkeys performing sensorimotor tasks can be substantially predicted by the spiking history of small, randomly sampled neuronal ensembles. The fact that this predictability was based on small neuronal ensembles, randomly sampled out of millions of neurons in the cortex, shows that strongly coordinated activity underlies the generation of single-neuron spikes. This finding is notable if one considers the properties of cortical neuronal networks. Cortical neurons are embedded in large, sparsely connected recurrent networks in which the high number of synaptic inputs and high-conductance states typically induce weak coupling between randomly sampled neuron pairs. Revealing and understanding these large scale and dynamic inter-actions has been challenging. On the basis of only the weak pair-wise correlations observed amongst cortical neurons in our datasets, one would have underestimated the strength of the statistical interdependencies induced by the collective dynamics. Furthermore, estimates of predictive power for these small neuronal ensembles should be taken as lower-bound values. There are at least a few factors that could have diminished predictive performance. For example, trials or time segments were included in which the hand was moving or the human participants were controlling a computer cursor. It is possible that the network's functional connectivity was nonstationary within and across trials. Also, more complex, and thus potentially more predictive, point process history models for computational tractability were avoided.

The fact that spiking was better predicted by the ensemble's history than by the ensemble's simultaneous collective state, estimated via pair-wise maximum entropy models, emphasizes the temporal dynamics leading to spiking. This finding, however, should not be taken as a limitation of pair-wise maximum entropy models. It is possible that multiple time-lag pair-wise correlation maximum entropy models might capture most of the history effects detected in our data and therefore provide a simpler, minimal model (Tang, A. et al., 2008 J. Neurosci. 28, 505-518; Mane, O. et al., 2009 Phys. Rev. Lett. 102, 138101). Goal here was to determine the existence and strength of such dynamics in the cortex of humans and behaving monkeys and not to provide such a minimal model for the temporal and instantaneous collective dynamics that should also be addressed.

It was shown that the spiking activity of small, simultaneously and randomly sampled neuronal ensembles in motor cortex can be used to predict (decode) subsequent complex behavioral variables such as arm kinematics (Paninski, L. et al., 2004 J. Neurophysiol. 91, 515-532; Wessberg, J. et al., 2000 Nature 408, 361-365; Serruya, M. D. et al., 2002 Nature 416, 141-142; Hochberg, L. R. et al., 2006 Nature 442, 164-171; Truccolo, W. et al., 2008 J. Neurosci. 28, 1163-1178). Here, the activity of these same neuronal ensembles can also be used to predict subsequent single-neuron spiking with substantial accuracy, implying the presence of strong collective dynamics in sensorimotor cortex. One may then ask how these collective dynamics relate to behavior. Although a comprehensive analysis of this problem is beyond the scope of this study, our results indicate that these collective dynamics do not simply reflect background coherent states that are completely unrelated to behavior and, conversely, do not simply reflect 'trivial common inputs', such as those usually considered in studies involving stimulus-driven activities of early sensory neurons. Regarding the background coherent states, our data indicate that the predictive power of models based only on ensemble history and of models based only on kinematics are not strictly additive (FIG. 7). In other words, there is some level of redundancy between the information (about single-neuron spiking) conveyed by ensemble spiking histories and information conveyed by kinematics variables. Therefore, the detected collective dynamics cannot simply reflect background coherent states that are entirely unrelated to behavior. Nonetheless, it is still possible, if not likely, that part of the detected collective dynamics may reflect ongoing internal processes that are not related to behavioral variables. Regarding common inputs, we note that kinematics and other features of voluntary movements are controlled in large part (either directly, or indirectly via spinal and muscle activations) by the coordinated activity of sensorimotor cortical neurons. It is, therefore, not surprising that these behavioral variables can also achieve substantial explanatory power for spiking activity. Even so, the fact that kinematics (pathlet) models were less predictive than ensemble history models suggests that the latter carried extra information about single-neuron spiking (FIG. 6). Given these considerations, the detected collective dynamics are unlikely to be explained as the simple reflection of trivial common inputs. In sum, we believe that these strong collective dynamics reflect the intra and inter-areal coordinated activity of neuronal ensembles distributed in the many different cortical and subcortical areas that participate in voluntary control of movement.

Detected collective dynamics and ensemble influences on spiking activity were hypothesized to reflect information transfer and computation in cortical networks. Collective dynamics and functional connectivity, as captured by connectivity matrices derived from ensemble history models, as well as predictive power levels, should vary as information transfer and computation change during behaviors that engage cortical areas. On the basis of current computational theories of motor control, one could predict, for example, that M1↔5d spiking predictability will manifest primarily during the initial phase of reaching movements, and M1↔PMv spiking predictability will peak during the hand-shaping phase of object grasping (Kalaska, J. F. et al., 1997 Curr. Opin. Neurobiol. 7, 849-859; Shadmehr, R. et al., 2008 Exp. Brain Res. 185, 359-381). A related and more general inquiry will be to examine the relationship of collective dynamics at this 'microscopic' spatial scale to neural activities reflected in meso- and macroscopic scale signals, such as local field potentials and electrocorticograms.

Results have implications for neural decoding theory and intracortical neural interfaces for motor prostheses. Collective dynamics add redundancy and, therefore, error-correcting properties to neural codes (Schneidman, E. et al., 2006 Nature 440, 1007-1012). In addition, these dynamics might also account for variability of neural responses, which is otherwise usually attributed to noise (Arieli, A. et al., 1996 Science 273, 1868-1871). Therefore, it seems that ensemble history effects should be taken into consideration when decoding kinematics (or other variables) from the spiking activity of neuronal ensembles. One would predict that decoding algorithms that take into account ensemble spiking histories will outperform algorithms that treat spiking activity of different neurons as, conditioned on decoded variables, independent processes.

Findings herein show that the presence of strong collective dynamics is fundamental to the experimental endeavor of determining coordinated spiking in cortical networks. Networks responsible for specialized cortical function are likely to be contained in the spiking patterns of millions of neurons distributed across multiple cortical areas. Current and developing recording technologies measure the spiking activity of hundreds to thousands of neurons, a very small fraction of these networks. Without strong collective dynamics (that is, if neurons in small randomly sampled ensembles behaved seemingly independently), there would be little hope of determining how the coordinated propagation of action potentials in large-scale recurrent networks leads to computation and information processing. These collective dynamics offer a basis for understanding cognition and adaptive behavior at the level of coordinated spiking in cortical networks.

Example 15. Patients with Focal Epilepsy: Clinical Electrodes and Recordings

Four patients (A, B, C, and D, ages 21-52 years, mean age 29.7 years, 3 women) with medically intractable focal epilepsy underwent clinically-indicated intracranial cortical recordings using grid electrodes for epilepsy monitoring (Delgado-Escueta A V, et al. The selection process for surgery of intractable complex partial seizures: Surface EEG and depth electrography. In: Ward A A Jr, Penry J K, Purpura D P, editors. 1983 Epilepsy. New York: Raven press, p. 295-326; Engel J, et al. Surgical treatment of partial epilepsies. In: Rosenburg R N, Grossman R G, Schoclet 5, editors. 1983 The Clinical Neurosciences. New York: Churchill Livingston, pp. 1349-1380). Clinical electrode implantation, positioning, duration of recordings, and medication schedules were based on clinical need as judged by an independent team of clinicians.

Patients were implanted with intracranial subdural grids, strips and/or depth electrodes (Adtech Medical Instrument Corporation, Racine, Wis.) for 5-10 days in a specialized hospital setting until data sufficiently identified the seizure focus for appropriate resection. Continuous intracranial EEG was recorded with standard recording systems (XLTEK, Ontario, Canada) and captured numerous seizures. Seizure onset times were determined by an experienced encephalographer based on inspection of ECoG recordings, referral to the clinical report of the ECoG, and clinical manifestations recorded on video. Among datasets with clearly separable single units, we selected 8 different seizures between the four patients. The number of seizures varied across the patients. Due to operational issues, not all of these seizures were recorded or provided high signal-to-noise ratio data. Among the datasets with clearly separable single units, we selected 8 seizures. The steps of the analysis of intracranial EEG data were performed using Neuroscan Edit software (Compumedics, El Paso, Tex.) and custom designed MATLAB (MathWorks, Natick, Mass.) software.

Example 16. Patients with Focal Epilepsy: Microelectrode Array Location, Recordings, and Analysis Patients were enrolled in the study after informed consent was obtained. Approval for these studies was granted by local Institutional Review Boards. The NeuroPort array (Blackrock Microsystems, Salt Lake City, Utah), which has been used in a number of previous studies (Hochberg L R, et al. 2006 Nature 442: 164-171; Schevon C A, et al. 2008 J. Clin. Neurophysiol. 25: 321-330; Truccolo W, et al. 2008 J. Neurosci. 28: 1163-1178; Truccolo W, et al. 2010 Nature Neurosci 13: 105-111, incorporated herein by reference in its entirety; Keller C J, et al. 2010 Brain 133(Pt 6): 1668-1681; Kim S-P, et al. 2008 J. Neural. Eng. 5: 455-476), is a 4 mm by 4 mm microelectrode array composed of 100 platinum-tipped silicon probes. Arrays with 1.0 mm long shanks were placed in the following areas: middle frontal gyms (Patient C) and middle temporal gyrus (Patient A, B, D).The distance to the nearest ECoG electrode where seizure onsets were detected was approximately 2 cm in Patients A, B and approximately 4 cm in Patient D. The NeuroPort was implanted within a broad focus in Patient C. These distances were determined based on 3D reconstructions of the cortical surface and location of ECoG electrodes was defined by a merging of the MM and post-operative CT scans. Recordings were made from 96 active electrodes and data were sampled at 30 kHz per electrode (0.3 7 kHz bandwidth). Patients were monitored in a specialized hospital setting until sufficient data were collected to identify the seizure focus, at which time the electrodes were removed and, if appropriate, the seizure focus was resected. Continuous intracranial EEG was recorded with standard recording systems (XLTEK, Ontario, Canada) with sampling rates of 500 Hz.

For detection and extraction of extracellularly recorded action potentials, the data was further online high-pass filtered (250 Hz-7.5 kHz, $4^{th}$-order Butterworth filter) and the analogue signal was automatically amplitude thresholded to detect putative neuronal spikes (Cerebus system, Blackrock Microsystems, Salt Lake City, Utah). The extracted waveforms were sorted using standard sorting methods (Lewicki Miss. 1994 Neural Comput 6: 1005-1030) and Offline Sorter (Plexon, Inc., Dallas, Tex.). Spike waveforms were tracked in time to ensure that changes in spiking rates were not artifacts due to waveform changes resulting from, for example, attenuation in spike amplitudes during neuronal bursting. Single neuron bursting rates were computed according to Staba et al. (Staba R J, et al. 2002 J Neurosci 22: 5694-5704). Classification of neurons into putative interneurons or principal cells (Bartho P, et al. 2004 J Neurophysiol 92: 600-608) (see FIGS. 22-23) was based on neuronal spike waveforms extracted after offline high-pass filtering (forward-backward Kaiser filter, 250 Hz high-pass cutoff) of the original data. The ECoG data and microelectrode data were synchronized using intermittent time stamp triggers sent to both recording systems.

Example 18. Observed Heterogenous Neuronal Spiking Pattern During Seizure Evolution A deeper understanding of neuronal spiking during the different phases of seizure generation would have profound implications for seizure prediction and may provide the basis for novel and more effective therapies for people with epilepsy (Jacobs M P, et al. 2009 Epilepsy & Behavior 14: 438-445). Specialized 96-channel microelectrode arrays (Hochberg L R, et al. 2006 Nature 442: 164-171; Schevon C A, et al. 2008 J Clin Neurophysiol 25: 321-330; Truccolo W, et al. 2008 J Neurosci 28: 1163-1178; Truccolo W, et al. 2010 Nature Neurosci 13: 105-111) (NeuroPort system, Blackrock Microsystems, Inc., Salt Lake City, Utah) were used to record single unit spiking activity and local field potentials from a four mm by four mm region of neocortex in four patients with epilepsy refractory to medical treatments. These patients were implanted with subdural grid electrodes to evaluate their cortical EEG activity (ECoG) and help localize the onset zone of their seizures for subsequent surgical resection. The microelectrode arrays were placed in addition to the grids (FIG. 12 panels A-D), with informed consent of the patient and with approval of the local Institutional Review Board. A total of 712 single unit recordings were identified in four patients (A, B, C and D). Single units were sorted using standard techniques (Examples 9-12). Although recording was continuous over several days, the consistent sorting of single units, over time periods longer than a few hours, proved challenging. Over such long periods, waveforms of extracellularly recorded action potentials could change and units appear or disappear from recordings, due perhaps to array micromotion, changes in brain states and other factors (Santhanam G, et al. 2007 IEEE Trans Biomed Eng 54 (11): 2037-2050). For this reason, for each analyzed session identified for study, those single units were identified for study that were consistently recorded during a time period of about 2 hours centered at the onset of each of the 8 seizures (see examples herein). Microelectrode arrays in Patient A (3 seizures, n=149,131 and 131 recorded single units), B (2 seizures, n=57 in each) and D (n=35 in 1 seizure) were placed in the middle temporal gyrus approximately 2 cm from the anterior tip. The microelectrode array in Patient C (2 seizures, n=82 and 70) was placed in the middle frontal gyrus. Microelectrode arrays were positioned both within (Patient C) and outside (approximately 2-4 cm distance; Patients A, B and D) the seizure onset zone as subsequently defined by the ECoG-electrode locations at which the seizure first appeared (see Examples).

Figure 12:
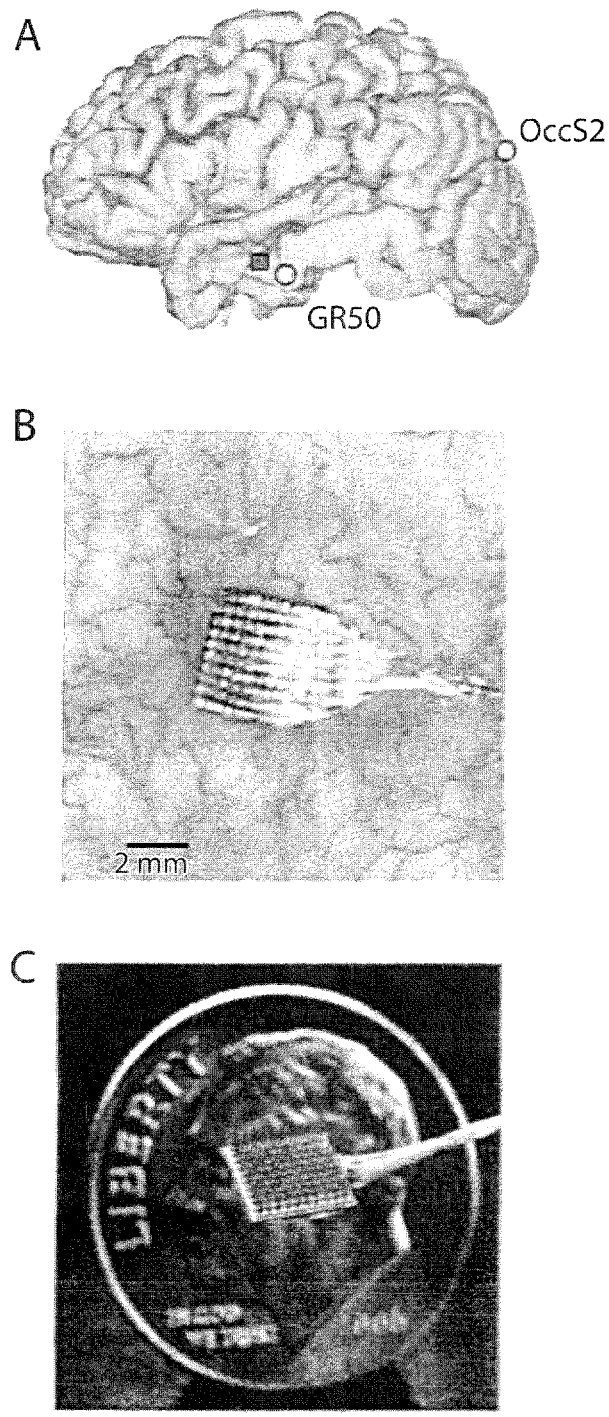
FIG. 12 is a set of photographs, electrocorticographs and heterogeneous neuronal spiking patterns observed during seizure evolution.
Figure 12:
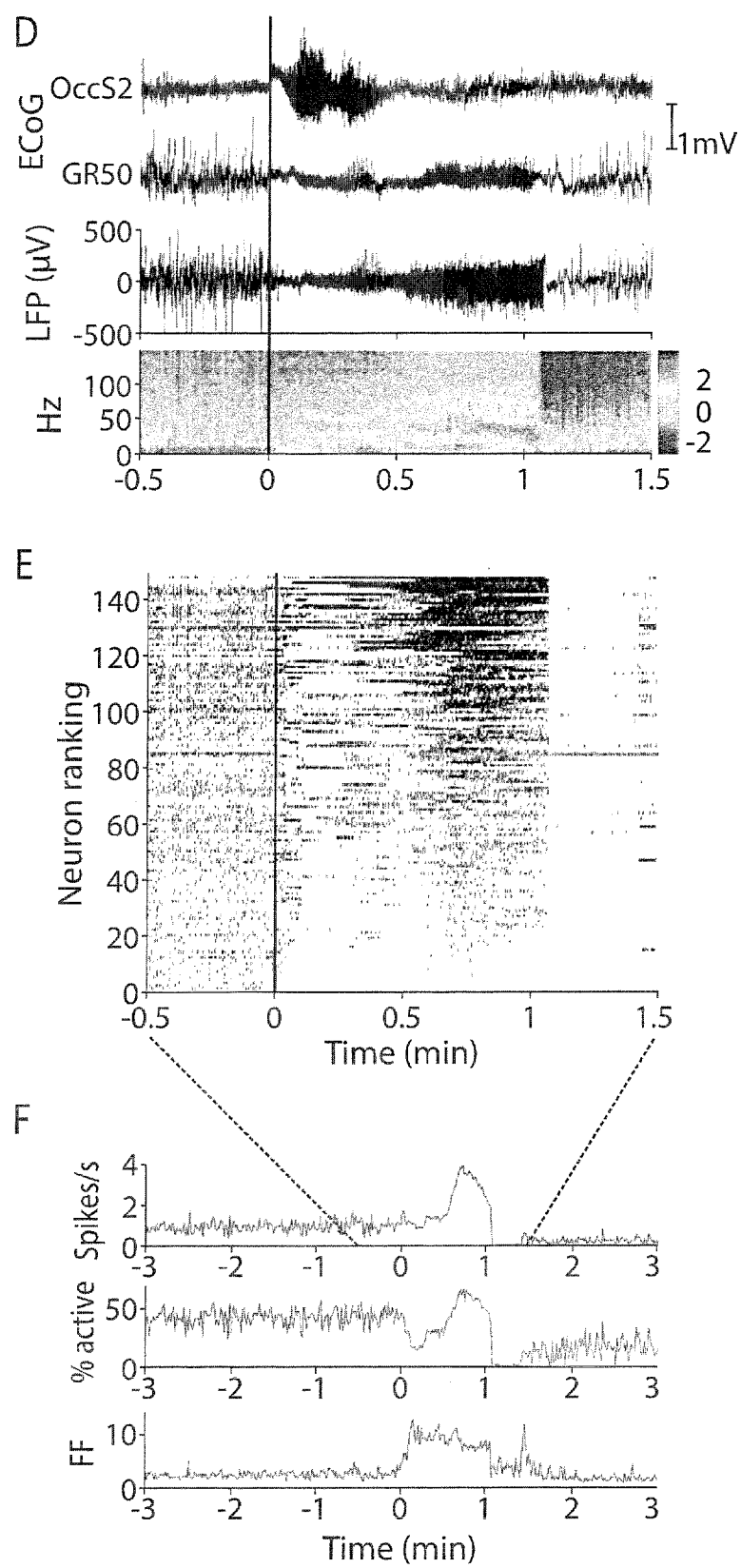

Visual inspection of neuronal spike rasters revealed a variety of spiking patterns during the course of a single seizure (FIG. 12 panel E). For example, while some neurons increased their spiking rates near the seizure onset, others decreased. These transient spiking rate modulations occurred at different times for different groups of neurons.

Figure 13:
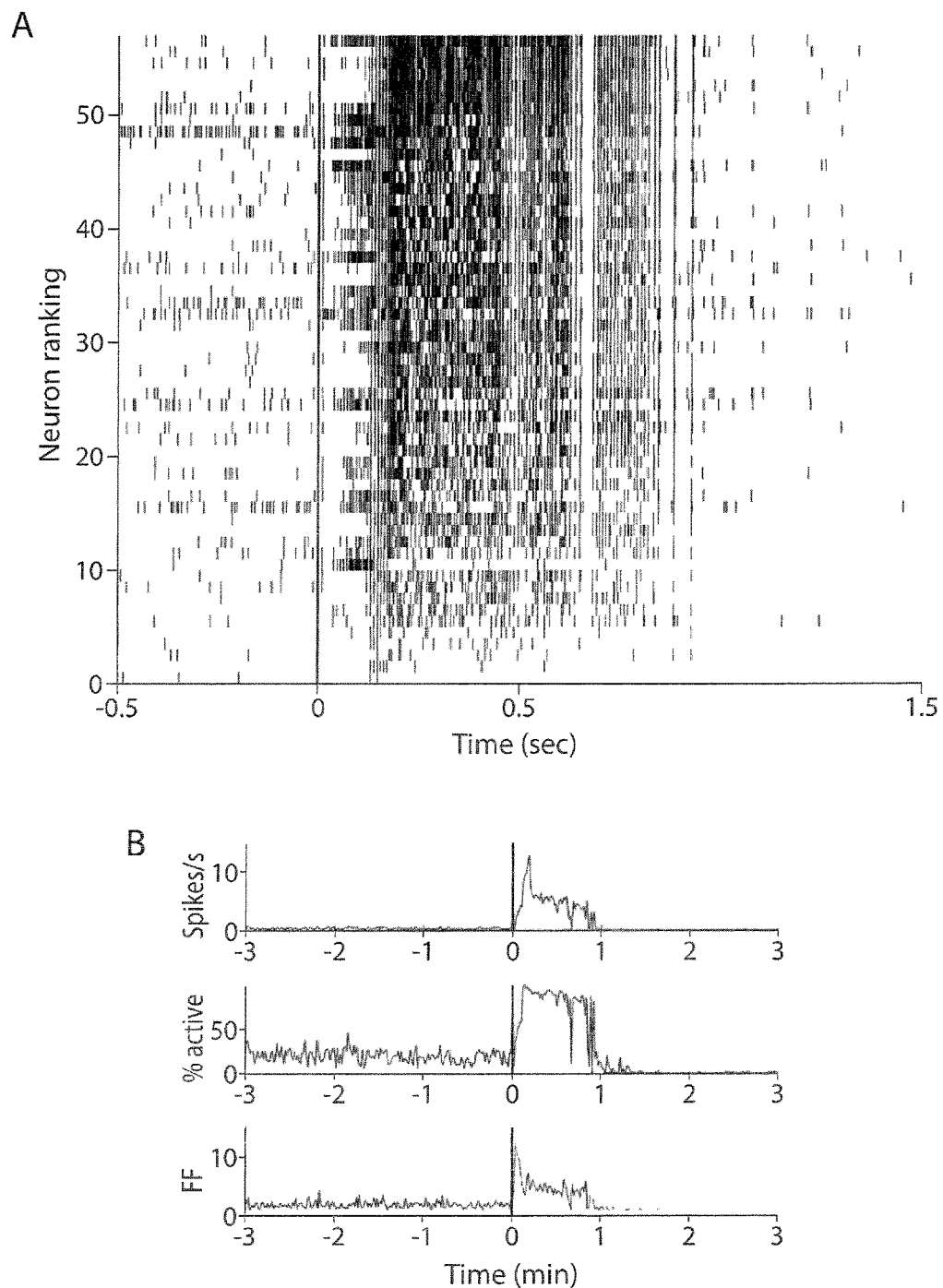
FIG. 13 is a set of graphs showing additional examples of heterogeneous spiking patterns during seizure evolution.
Figure 13:
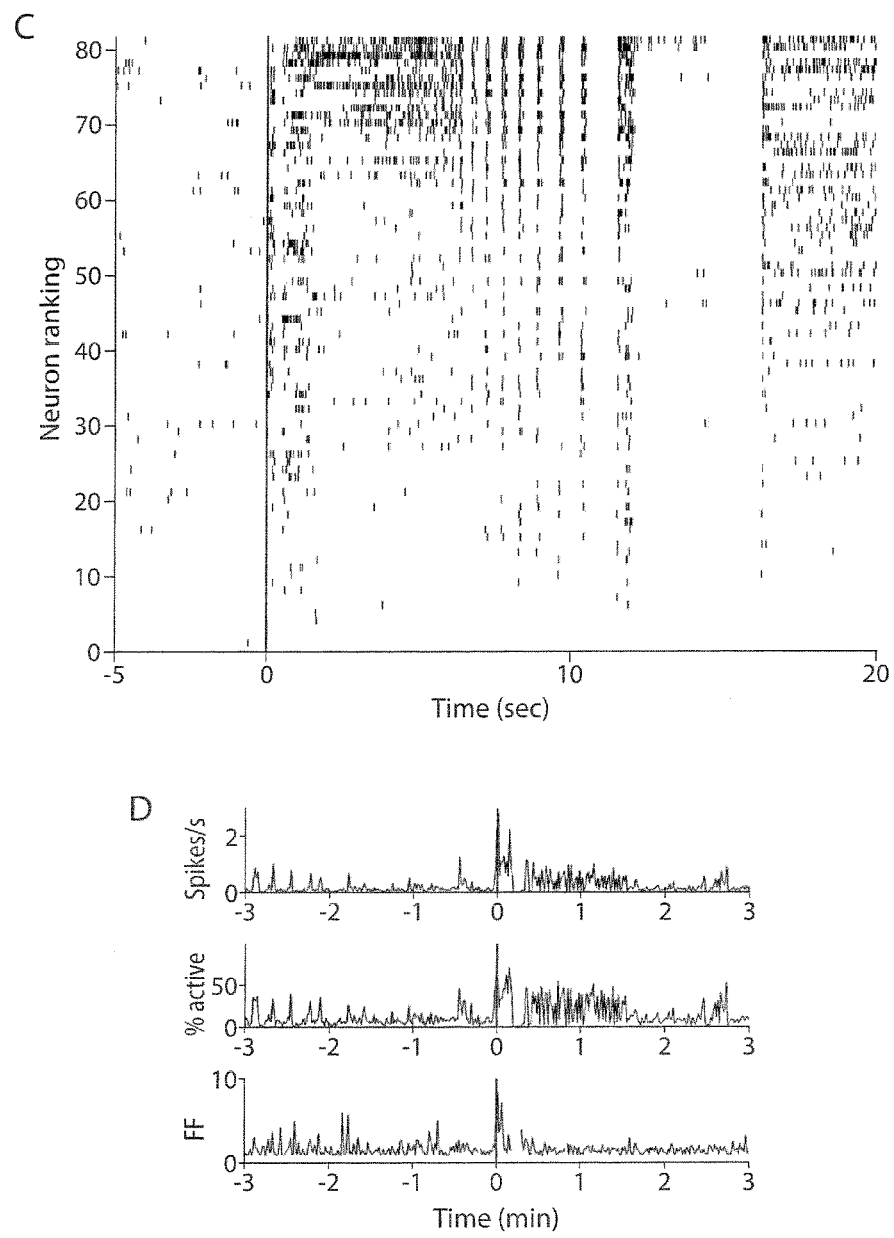
Figure 13:
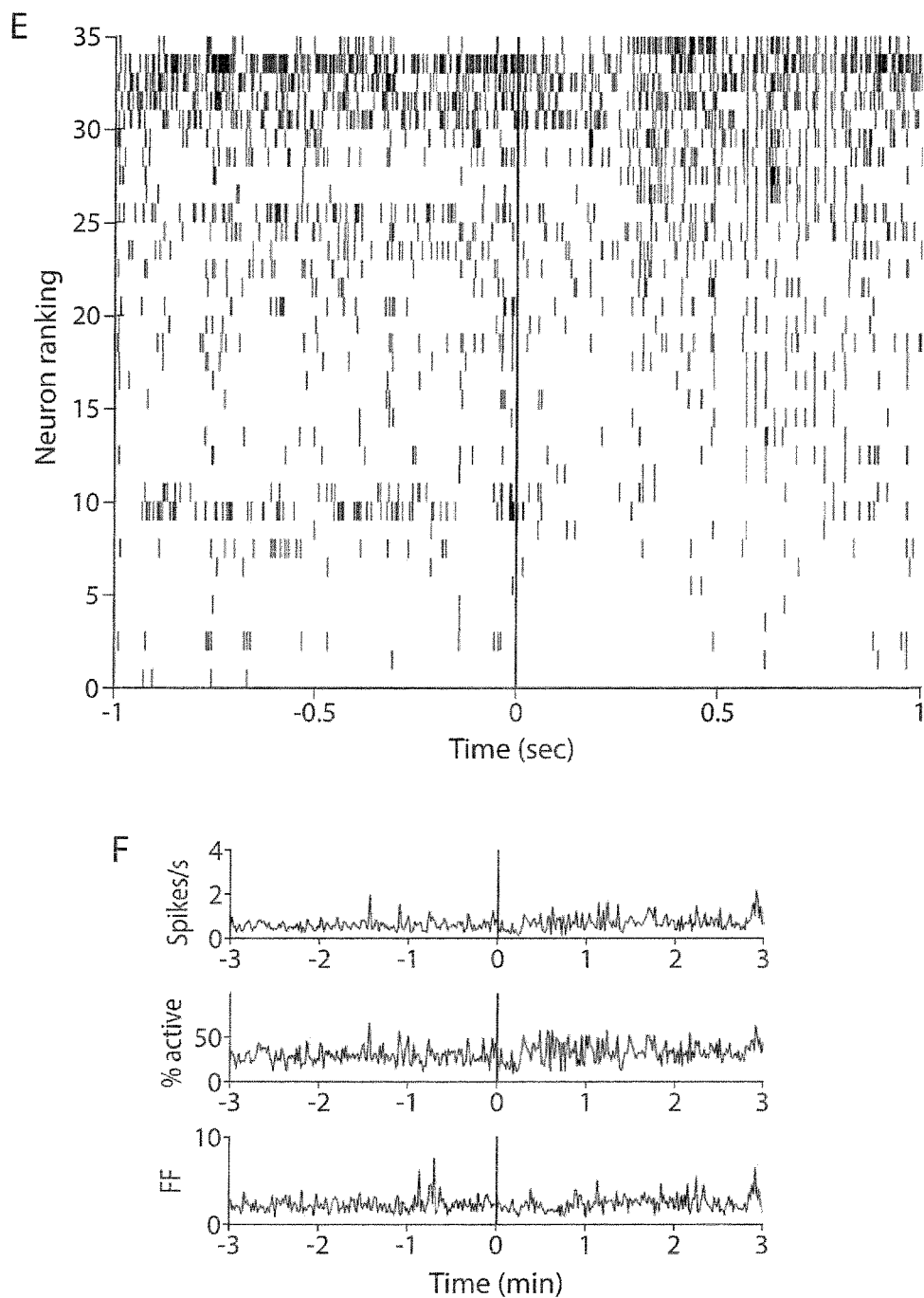

Heterogeneity of spiking patterns was also evident from the increase in variability of the number of neuronal spike counts across the population in a given time bin (e.g. 1 second). The Fano factor (variance divided by the mean) of the number of spike counts across the population, which gives an index of the variability or heterogeneity of spiking in the ensemble, increased substantially after the seizure onset—in some seizures by fivefold (FIG. 12 panel F). This diversity of neuronal modulation patterns was observed to a greater or lesser extent in the seizures and patients studied (FIG. 13).

Such heterogeneity in spiking rate modulation patterns directly challenges the canonical characterization of epileptic seizures as a simple widespread hypersynchronized state, i.e., a state in which the active neurons simultaneously spike in a single-cluster, phase-locked fashion. Heterogeneity was present whether the seizure initiated near (Patient C) or far (the other three patients) from the location of the microelectrode array. The admixture of different spiking patterns observed indicates that heterogeneity is not purely a product of activity propagation. Surprisingly, based on the Fano factor, this heterogeneity was higher during seizure initiation and decreased towards seizure termination (FIG. 12 panel F and FIG. 13). In contrast to the beginning of the seizure, seizure termination in Patients A, B and C involved nearly simultaneous and complete cessation of activity for the majority of recorded neurons (FIGS. 12-13). That such decreases in spiking activity (and also rate modulations during the seizure) were not due to sorting artifacts such as spike dropout was ascertained because of clearly observed alterations in spike waveform. These changes in spike waveforms could be induced by, for example, bursting activity and related changes in biophysical properties of isolated single units. Spiking activity remained silent for several seconds (ranging from 5 to 30 seconds) after seizure termination until more normal spiking rates gradually returned.

Example 19. Reproducibility from Seizure to Seizure of Spiking Patterns

Figure 14:
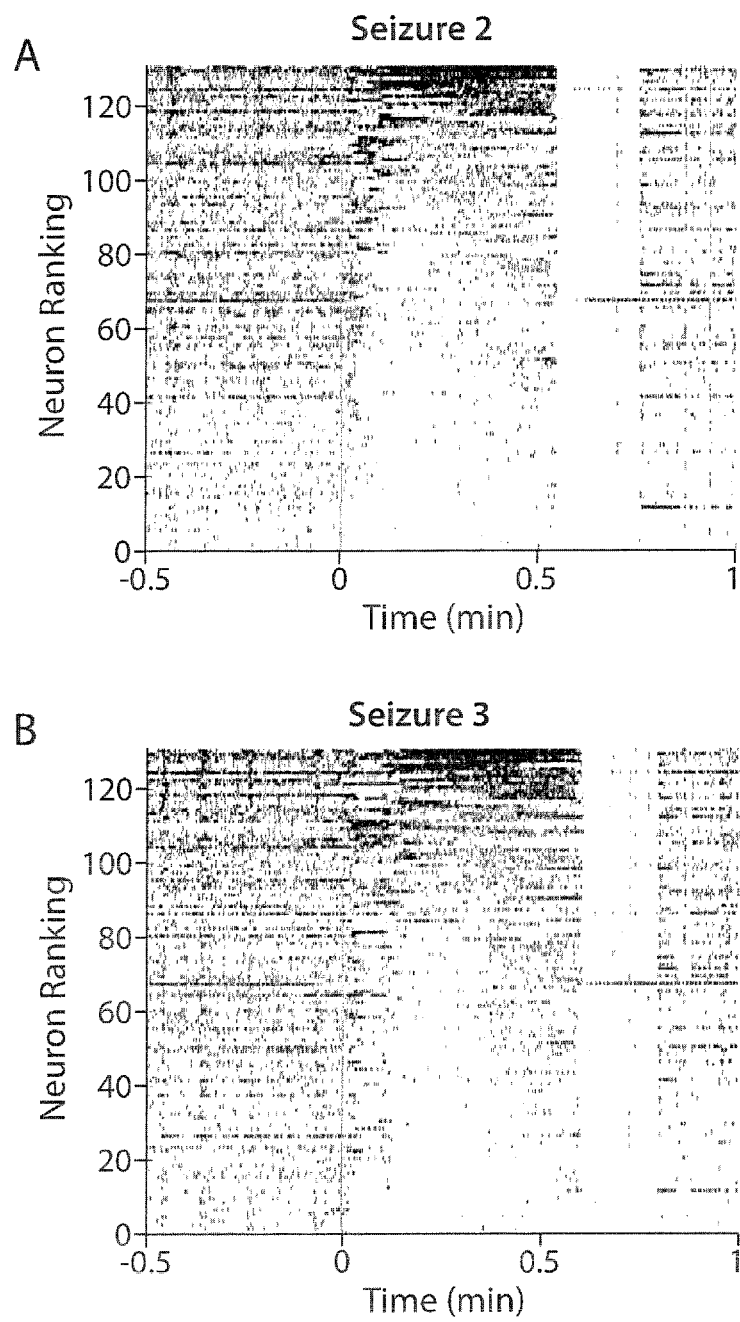
FIG. 14 shows reproducibility of neuronal spiking modulation patterns across consecutive seizures.
Figure 14:
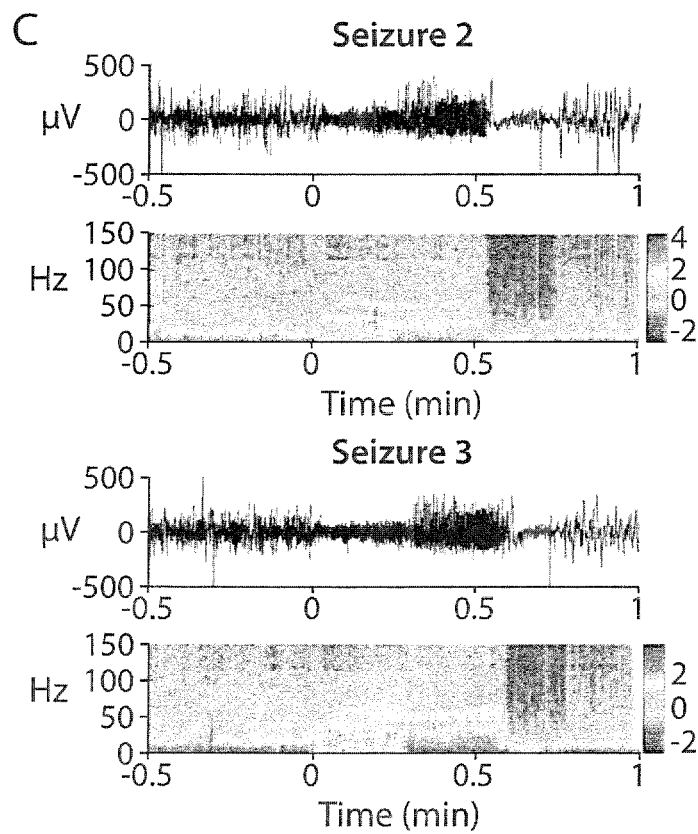
Figure 14:
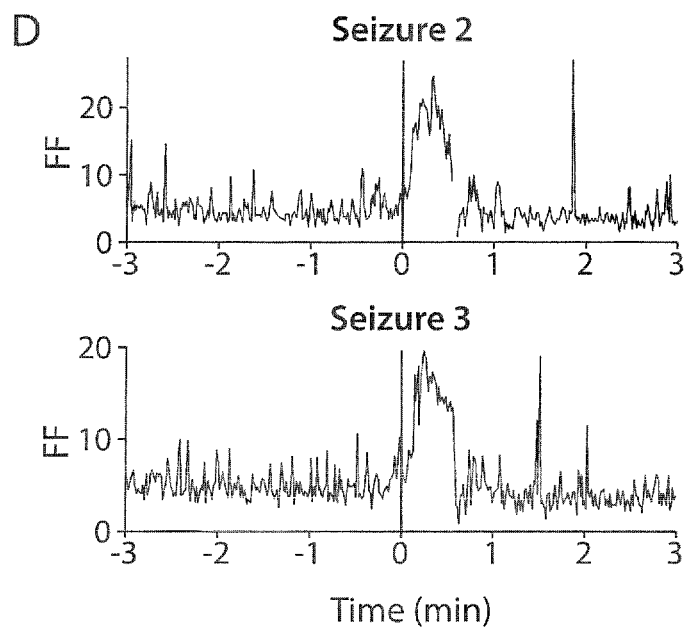
Figure 15:
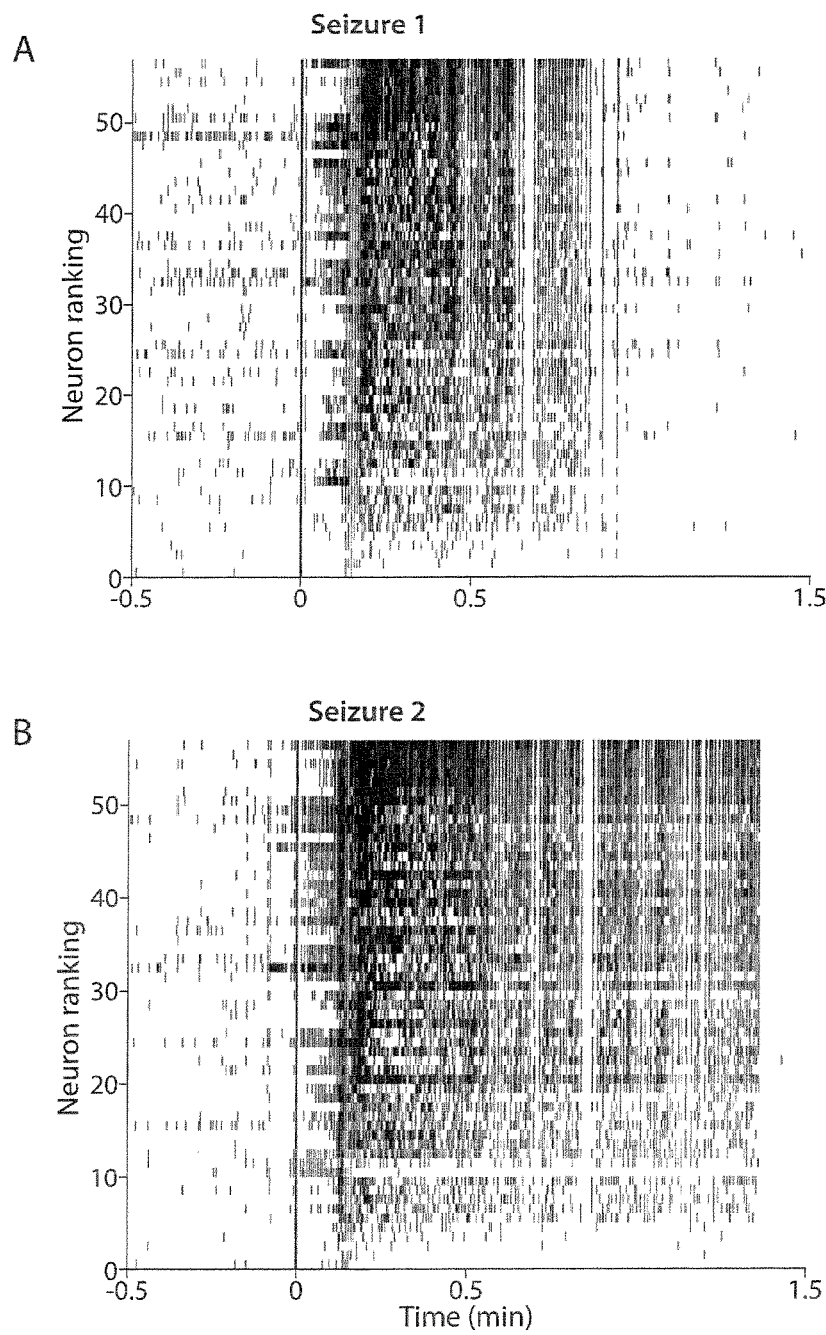
FIG. 15 panels A and B show additional examples of reproducibility of neuronal spiking modulation patterns across consecutive seizures. The seizures in Patient B occurred within about 1 hour allowing us to examine the reproducibility of neuronal spiking patterns across different seizures. Conventions are the same as in FIG. 12. Despite variations in duration, seizures 1 and 2 from Patient B show a common pattern, especially during seizure initiation. The correlation coefficient between two spike trains during the initial 30 seconds of each seizure, for each neuron and averaged across the population, was 0.72.
Figure 15:
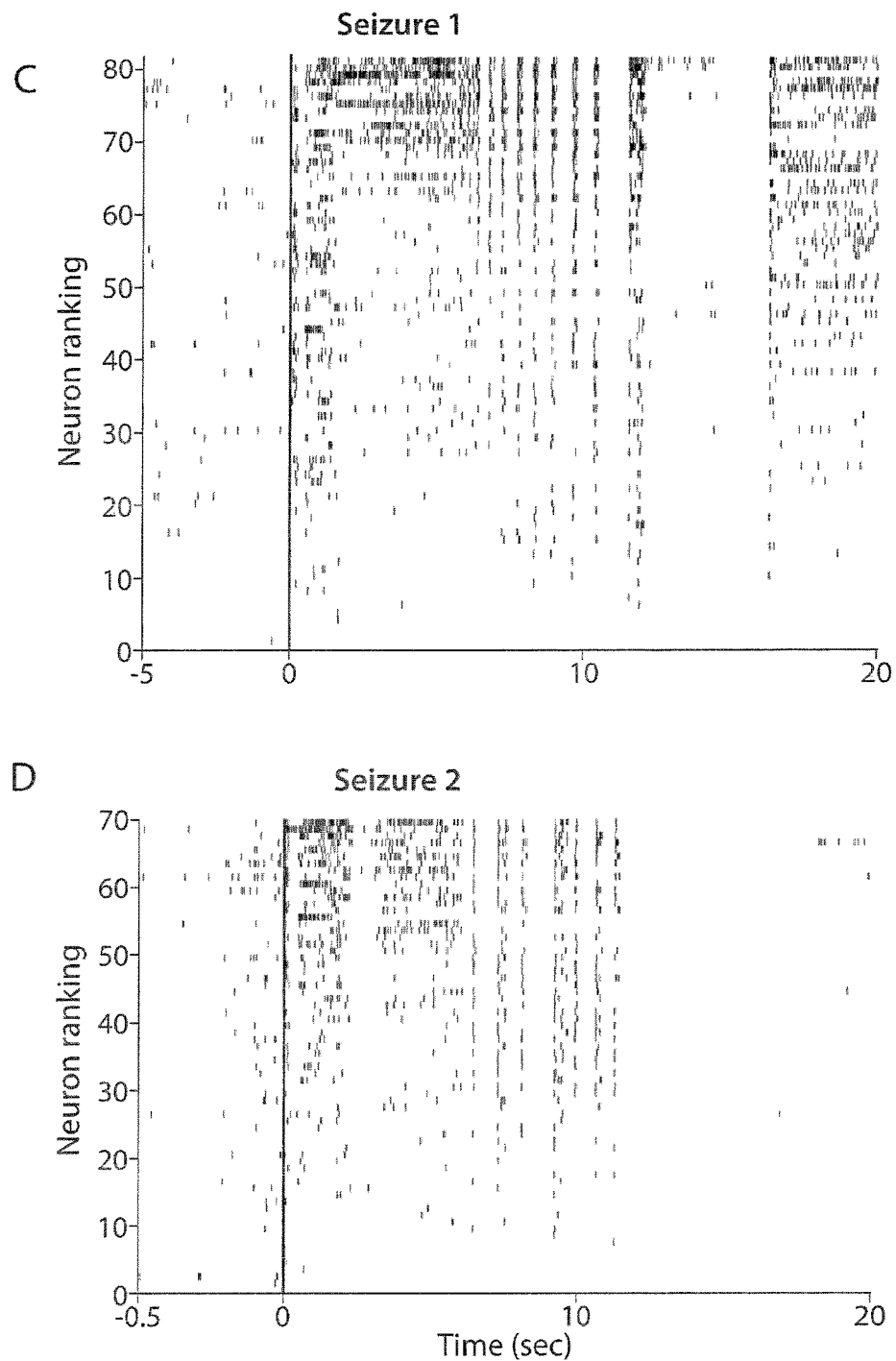
Figure 16:
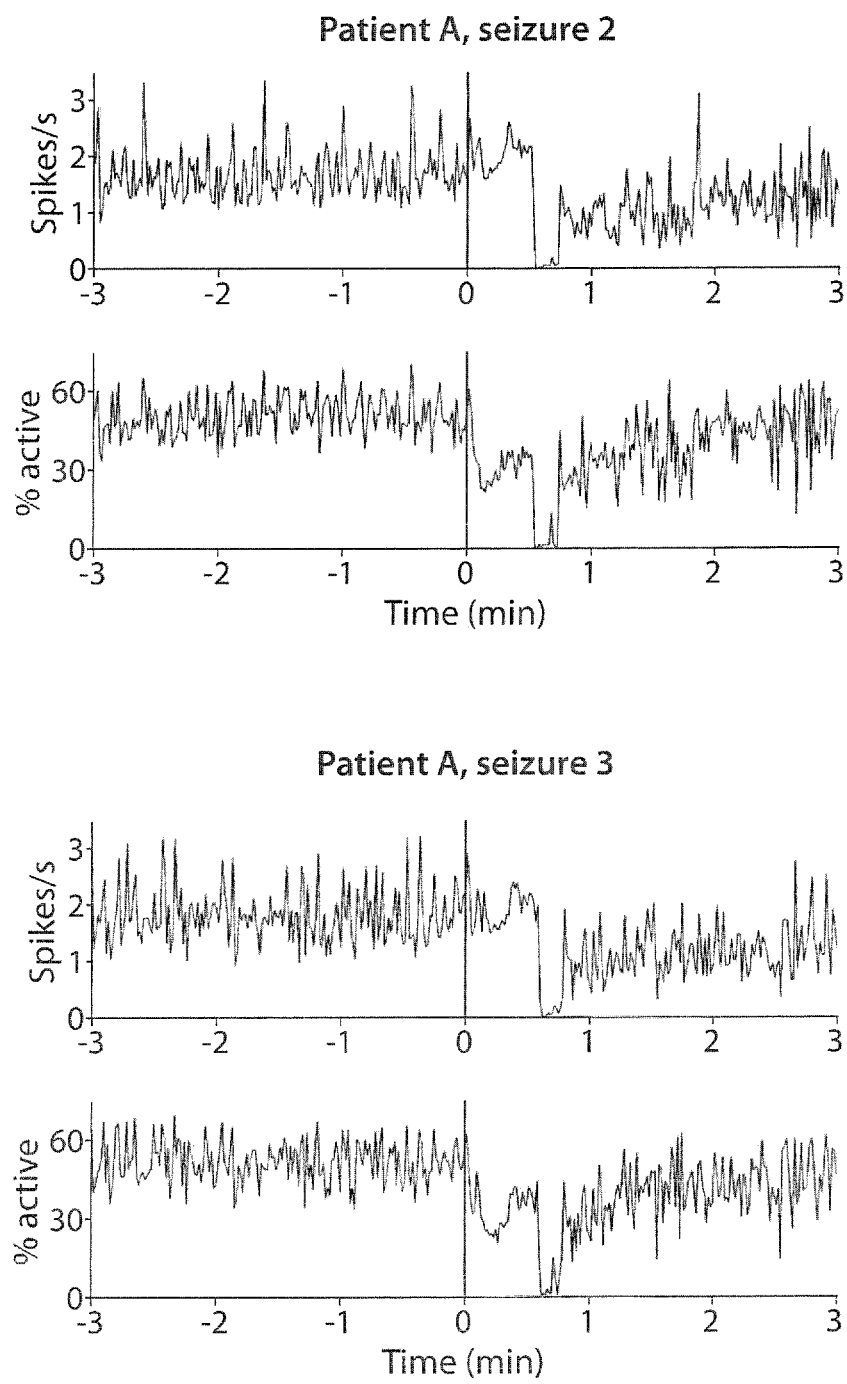
FIG. 16 is a set of tracings of a fraction of active neurons in seizure 2 and 3 (Patient A). In contrast to seizure 1 (FIG. 12), in which the fraction of active neurons transiently increased towards the end of the seizure, this fraction remained below the preictal level throughout seizures 2 and 3. Percentage of active neurons was computed on a 1-second time scale, i.e. a neuron was considered active once if spiked at least once in a given 1-second time bin. The top plot in each panel shows the spike rate, computed from spike counts in 1-second time bins, averaged across the ensemble of neurons.

Substantial reproducibility was observed in the overall neuronal spiking pattern from seizure to seizure within each patient. In particular, in Patients A and B, two consecutive seizures occurred within a period of about an hour. In these cases, it was ensured that the same units were recorded and consistently identified during both seizures (see Examples). This permitted examination the reproducibility of neuronal spiking patterns across seizures. For instance, despite the fact that the third seizure in Patient A lasted slightly longer than the second, the same motifs in the neuronal spiking patterns recurred (FIG. 14). The Pearson correlation coefficient (a measure of similarity) between two spike trains during the initial 30 seconds of each seizure, for each neuron and averaged across the population, was 0.82. Similar observation was also made for the two consecutive seizures in Patient B, with an average correlation coefficient of 0.72 (FIG. 15), indicating a high degree of repeated pattern in both seizures. Correlation coefficients for preictal periods corresponded to—0.3. Despite general similarities across seizures, there were also notable differences in the fraction of active neurons in the population. For example, while the fraction increased after a transient decrease at seizure onset in seizure 1 (Patient A; FIG. 12 panel F), throughout seizures 2 and 3 it remained lower than during the preictal period (FIG. 16).

Figure 17:
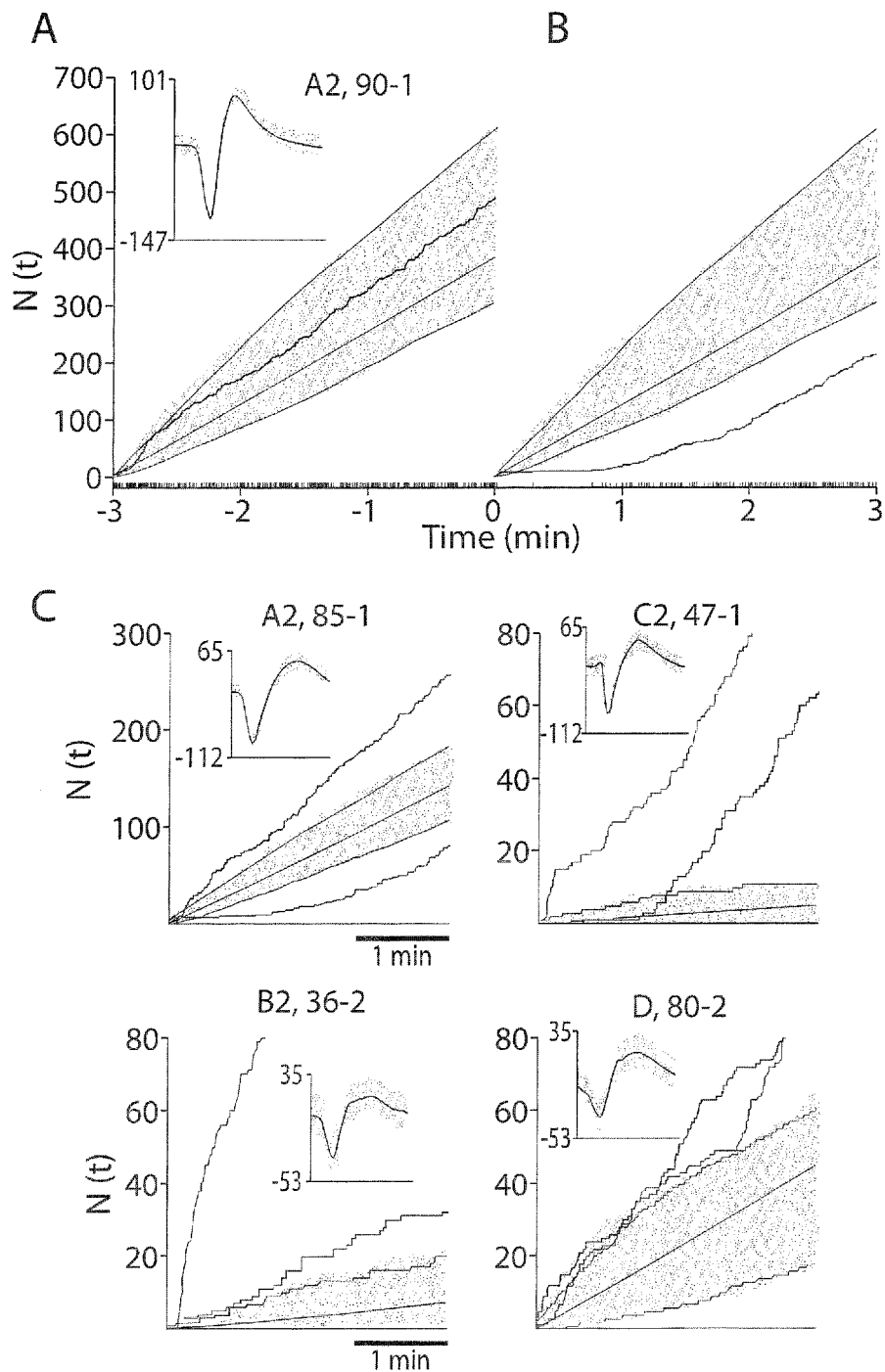
FIG. 17 shows preictal and ictal modulations in spiking rates.

Example 20. Spike Count Distribution During Interictal, Preictal and Ictal Period To better characterize preictal and ictal changes in spiking rates, a spike train of a single neuron was represented as a sample path. A sample path consists of the cumulative number of neuronal spikes as a function of time (FIG. 17 panel A). In contrast to a simple quantity such as mean rates, the sample path representation provided ability to preserve information about transient changes in instantaneous spiking rates; a neuron in two different experimental conditions might have the same mean spiking rate while showing very different sample paths. Whether an observed sample path for a given neuron during the preictal or ictal periods deviated from the collection of sample paths of same time length observed during the interictal period was analyzed. In this way, transient increases or decreases in spiking rate that were atypical with respect to the preceding interictal activity were detected.

Figure 18:
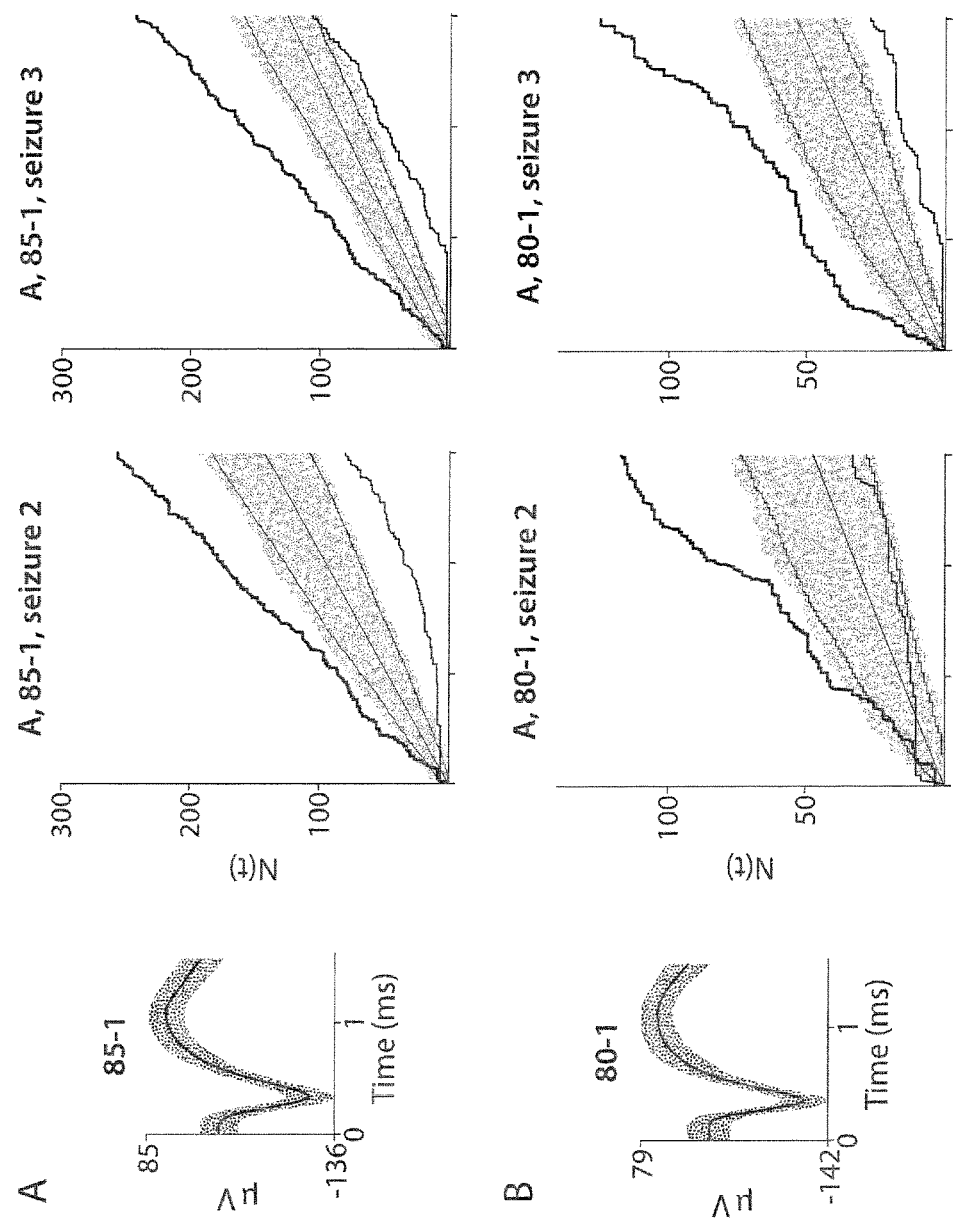
FIG. 18 shows sample path deviations across different seizures. The two consecutive seizures within about 1 hr. in Patients A and B was used to examine the reproducibility of sample path deviations across different seizures. Black curve: preictal sample path deviation; dark grey curve: ictal sample path deviation; light grey curves within the shaded region: average preictal and ictal sample path deviations.
Figure 18:
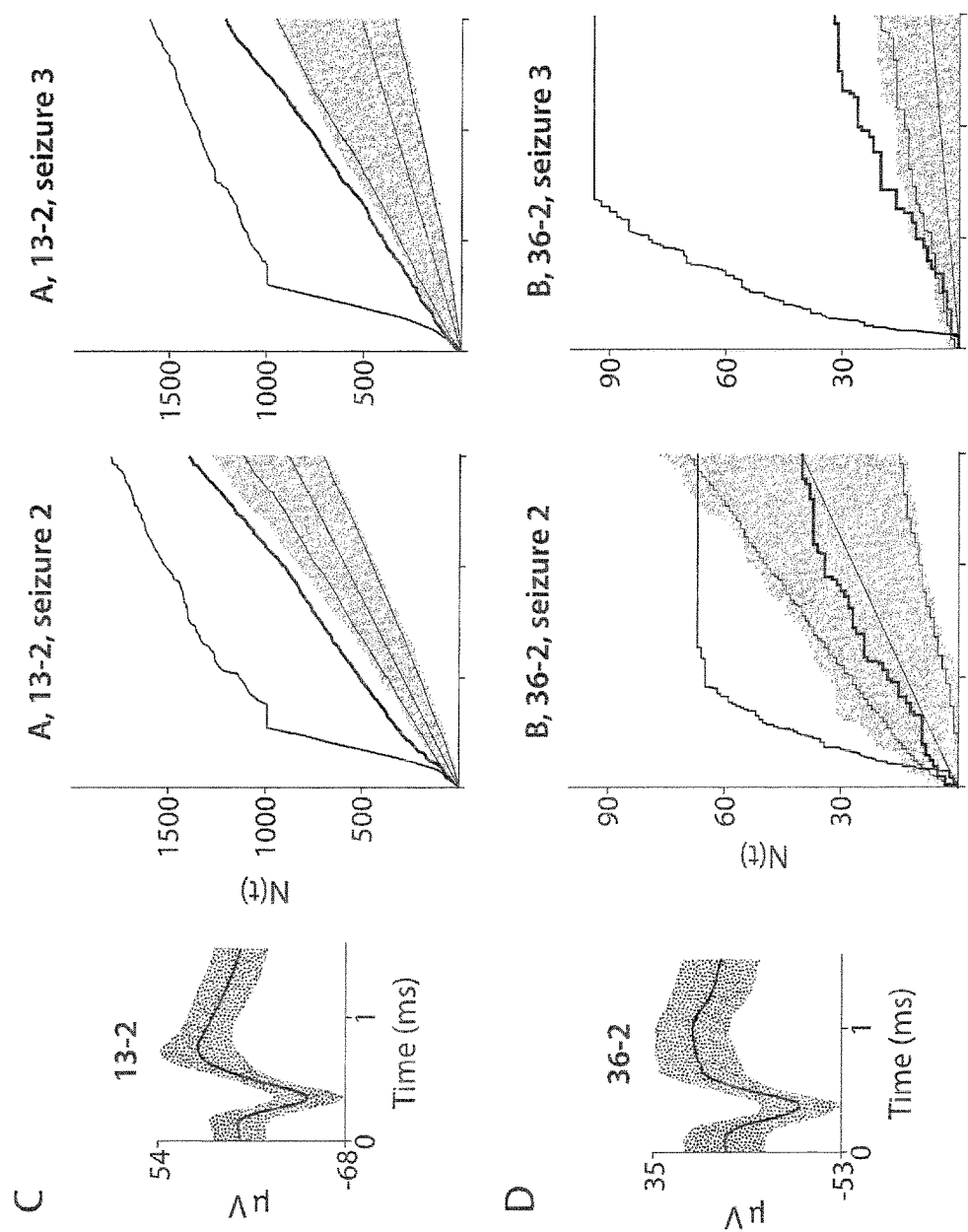

It was observed that substantial numbers of neurons significantly changed their activities as the seizure approached. The percentage of neuronal recordings that showed a preictal deviation varied from 20% (7/35, participant D) to 29.9% (123/411, participant A). Observed deviations consisted either of increases or decreases in spiking rate. Across all participants and seizures (712 recordings), 11.8% of recorded neurons increased their spiking rate during the preictal period, and 7.5% decreased. In many cases the onset time for the deviation was earlier than 1 min before the seizure onset time. This finding suggests that changes in neuronal spiking activity, even for single neurons recorded well outside the identified epileptic focus, may be detected minutes before the seizure onset defined by ECoG inspection. Several neurons in participants A showed consistent sample path deviations across seizures 2 and 3, the two consecutive seizures where the same single units were recorded (FIG. 18). The percentage of neuronal recordings that showed a sample path deviation during the ictal period varied from 22.8% (8/35, participant D) to 97.4% (111/114, participant B). In line with the heterogeneity observed in raster plots, several types of deviations were observed during the seizure—all from single units recorded simultaneously from a small cortical patch (encompassing different cortical columns). Across all participants and seizures, 45.4% and 9.9% of the neuronal recordings increased and decreased, respectively, their spiking rates during the seizure. Furthermore, a few neurons showed a transient increase (0.1%) followed by a transient decrease in spiking rates, or vice-versa (1.3%). Overall, we found fifteen different patterns of neuronal modulation when taking into consideration both preictal and ictal patterns.

Figure 19:
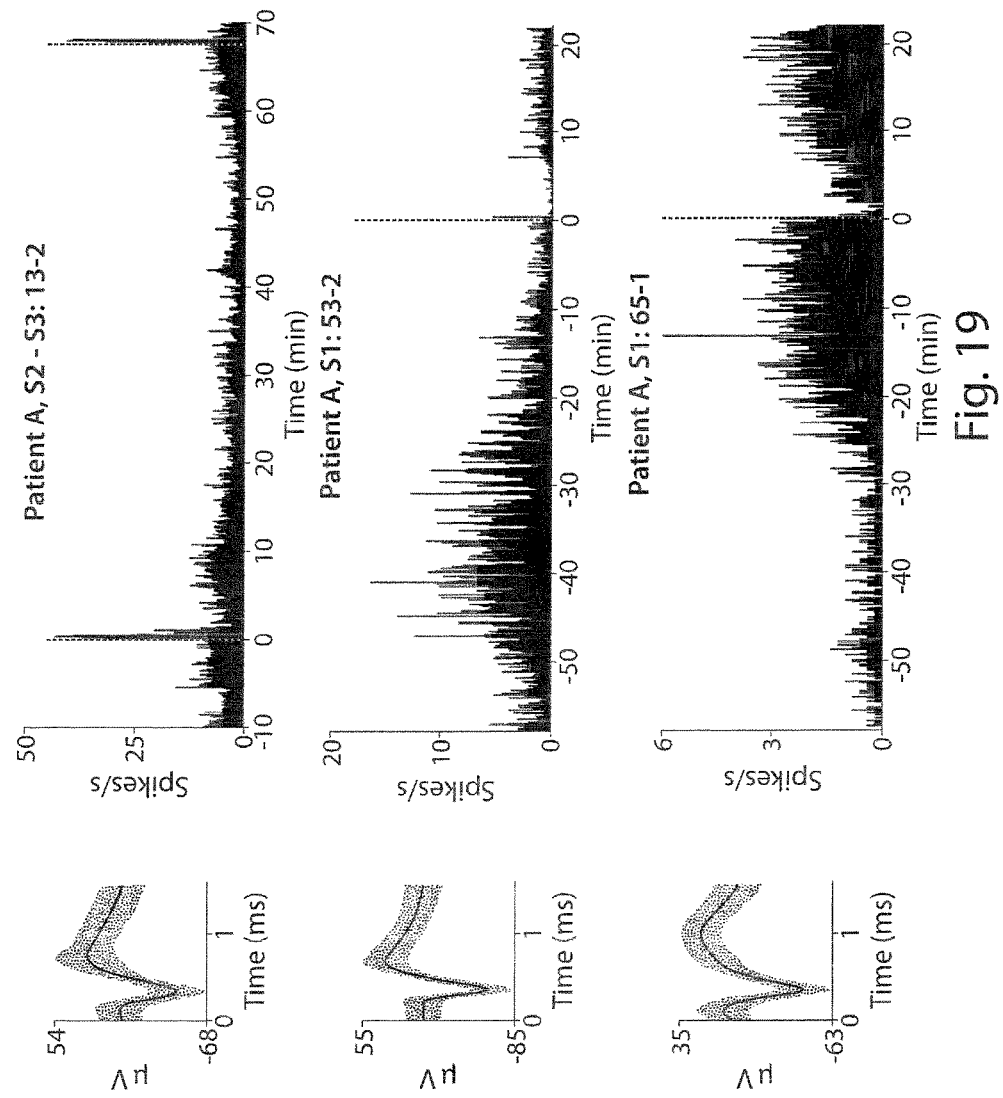
FIG. 19 is a set of spike rates that are examples of slow, strong modulations in neuronal firing rates. Spike rates were computed on 5-second time bins and show long term and in one case (top plot) reproducible, changes in firing rates in neurons long in advance of the seizure onset. Seizure onsets are marked by vertical lines at time zero minute.

In addition to these sample path deviations, a few neurons in Patient A also showed much slower and larger modulations in spiking rates that preceded the seizure onset by tens of minutes (FIG. 19 panels A-C), and were not correlated with clearly observed behavioral or state changes.

Figure 20:
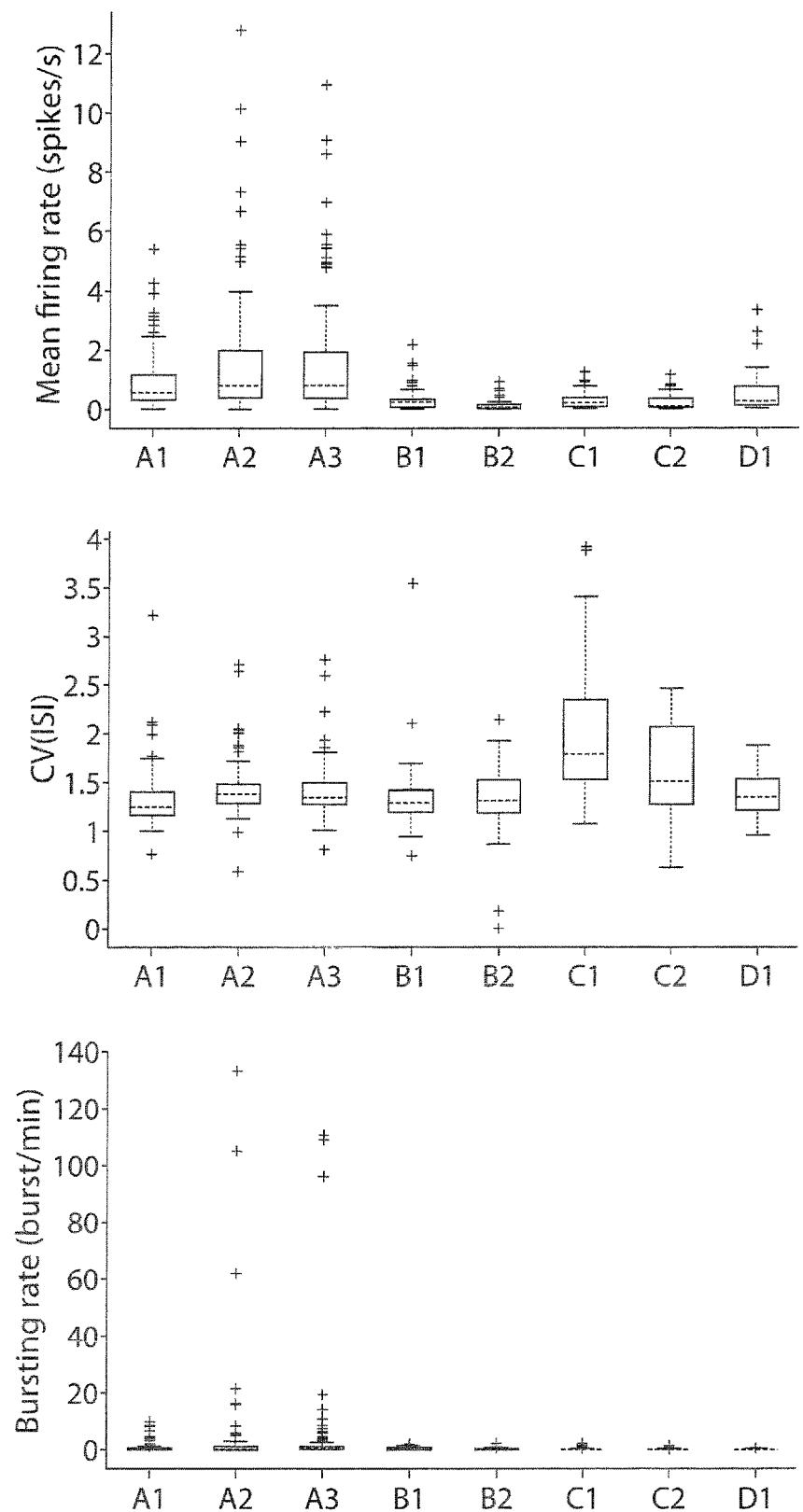
FIG. 20 shows interictal features of neuronal firing: mean spiking rates, ISI coefficients of variation (CV) and bursting rates. A 30-minute period preceding a defined preictal period of 3 minutes was chosen for characterizing basic firing properties of the individual neurons. A, B and C refer to patients and the numbers 1, 2 and 3 refer to particular seizures.
Figure 21:
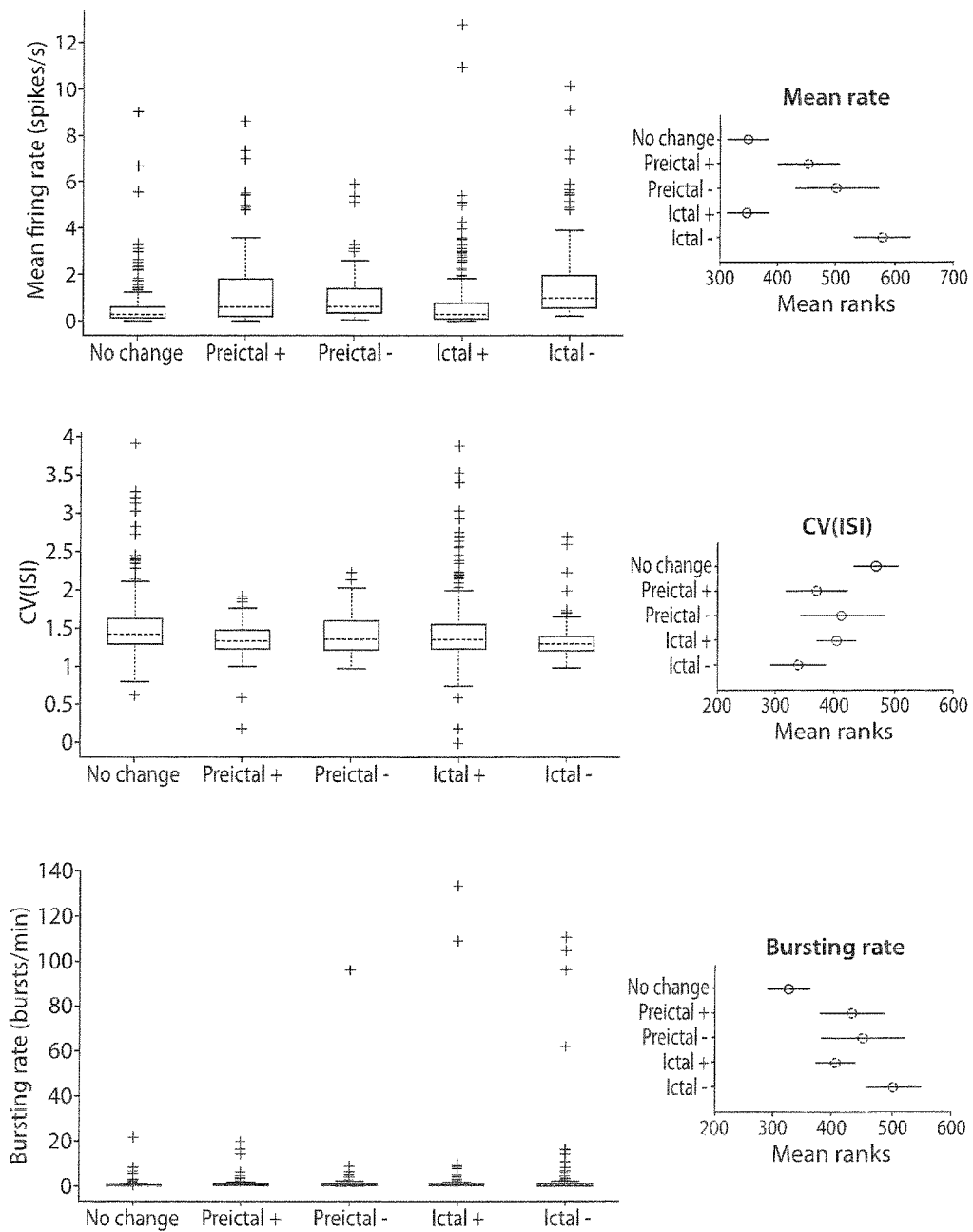
FIG. 21 shows interictal features compared to preictal and ictal modulation. Five main modulation types (including "no change") including data from all patients and seizures were examined. Insets show a summary from the Kruskal-Wallis test. Comparing "No change" with the other groups; in this case, bars in the insets represent significant differences ($P<0.01$, with correction for multiple comparisons based on "honestly significant differences" (Tukey-Kramer correction)). A noticeable significant difference was that neurons that showed a preictal or ictal modulation had higher bursting rates than neurons that did not show any type of change.
Figure 22:
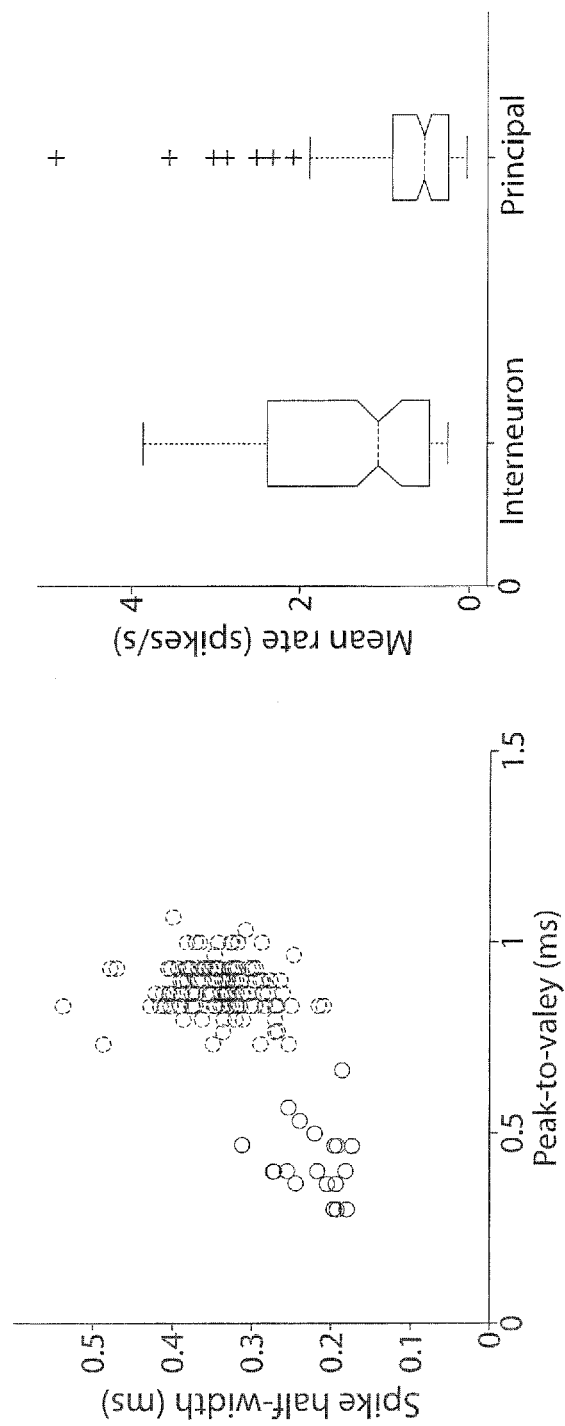
FIG. 22 shows neuronal subtypes: putative pyramidal cells and interneurons in Patient A, interictal period preceding seizure 1; similar clustering was observed using the Kruskal-Wallis test for difference between interneuron and pyramidal cell groups (1 and 2, respectively), $P<0.001$. Similar results were obtained for interictal periods preceding seizures 2 and 3.
Figure 23:
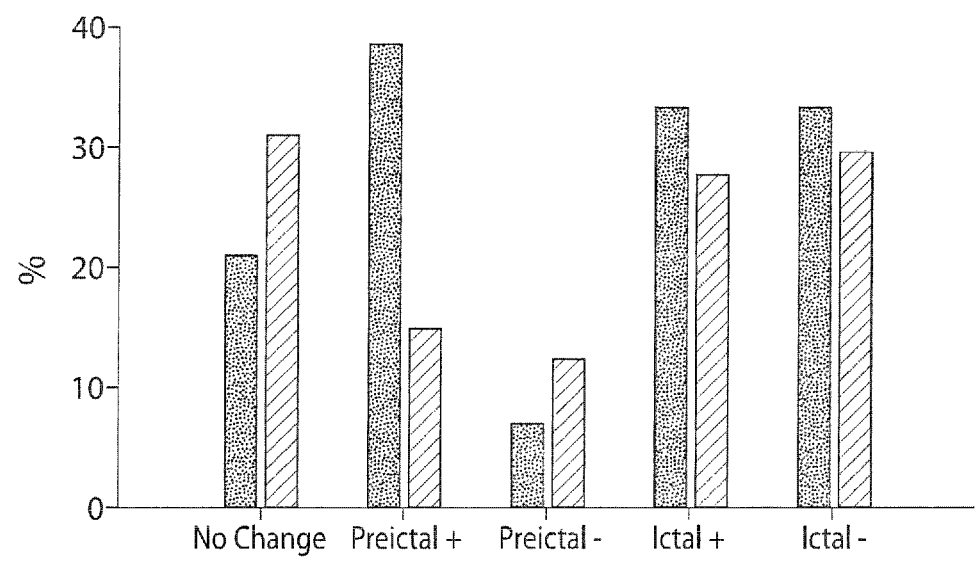
FIG. 23 is a bar graph showing modulation of interneurons (left in each pair) and principal cells (right). It was observed that 21% and 32% of interneurons and principal cells, respectively, showed no modulation. The remaining neurons in both groups were distributed non-uniformly across the 4 main modulations types (preictal and ictal increase or decrease in firing rate). In particular, fewer interneurons and principal neurons showed a preictal decrease (Chi-square test, $P<10^{-4}$ and $P<10^{-3}$, respectively, with Bonferroni correction for multiple comparisons). In addition, the fraction of recorded interneurons that showed a preictal increase was significantly larger than the corresponding fraction of principal neurons ($P<10^{-6}$). (Total number of neuronal recordings: 411; 57 interneuron recordings and 354 principal cell recordings).

Neurons that showed preictal and ictal modulation in spiking rates were observed to have statistically higher bursting rates during the interictal period (Kruskal-Wallis test, P<0.01, Tukey-Kramer correction for multiple comparisons; see examples herein and FIGS. 20-21). Furthermore, in Patient A, recorded single units could be classified into putative interneurons and principal neurons according to spike half width and peak-to-valley width (FIG. 22). Based on this classification, 79% (45/57) and 68% (240/354) of interneurons and principal cells recordings, respectively, showed some type of preictal or ictal modulation. In addition, the fraction of recorded interneurons that showed a preictal increase was 60% larger than the corresponding fraction of principal neurons ($x^2$ test, P<$10^{-6}$, with Bonferroni correction for multiple comparisons; see FIG. 23).

Example 21. Relevance of Analyses to Clinical Care

Data herein, based on a more extensive description of single unit activity in human neocortical seizures than has heretofore been available, reveal a number of important and significant findings about the nature of epileptic activity. The observed heterogeneity in neuronal behavior argues against homogeneous runaway excitation or widespread paroxysmal depolarization as the primary mechanism underlying seizure initiation. Rather, the data indicate that seizures result from a complex interplay among groups of neurons that present different types of spiking behaviors which evolve at multiple temporal and spatial scales. Similar heterogeneity was observed herein in interictal discharges (Keller C J, et al. 2010 Brain 133(Pt 6): 1668-1681). Given the 1-mm microelectrode length, it is likely that cells in layers 3 and 4 were recorded. Several studies (Pinto D J, et al. 2005 J Neurosci 25(36): 8131-8140; Connors B W. 1984 Nature 310: 685-687; Ulbert I, et al. 2004 Epilepsia 45 (Suppl 4): 48-56) show that epileptiform activity involves and is perhaps initiated by cells in layer 5. Although the potential role of these cells needs to be further explored, they do not appear to be driving homogenous activity. The heterogeneity in the neuronal collective dynamics (Truccolo W, et al. 2010 Nature Neurosci 13: 105-111) resembles fragmentation into multicluster synchronization, which has been studied in various dynamical systems (Amritkar R E, et al. 2009 International J Bifurc Chaos 19(12): 4263-4271). The fact that such diverse spiking activity underlies seemingly monomorphic EEG waveforms raises the possibility that even normal cortical rhythms might also reflect heterogeneous neural ensemble spiking.

Another surprising feature of these data was the abrupt and widespread termination of neuronal action potentials at seizure end. In Patient A, for example, both putative interneurons and principal neurons became silent. Prior work has suggested that seizures might end due to changes in the ionic concentration of the extracellular space. A depolarization block of neuronal spikes has been thought due to a chain of events that ends with astrocytic release of large amounts of potassium (Bragin A, et al. 1997 J Neurosci 17(7): 2567-2579). It is unclear, however, whether this type of depolarization block could account for the fast and homogeneous silencing of neuronal spiking on the spatial scales (4 mm by 4 mm patches and likely larger areas) observed here. Without being limited by any particular theory or mechanism of action, data herein argue against massive inhibition from a local source, since the silencing of neuronal spiking affected putative interneurons and other cells simultaneously. Alternatively, distant modulatory inputs involving subcortical structures, e.g. thalamic nuclei or substantia nigra pars reticulata (Lada F A, et al. 2008 Epilepsia 49(10): 1651-1664), could lead to seizure termination. It is possible that this critical transition could arise from an emergent property of the network itself leading to spatially synchronous extinction (Amritkar R E, et al. 2006 Physical Review Letters 96: 258102).

From a therapeutic perspective, analysis herein demonstrates for the first time in humans that preictal neuronal spiking reflects a distinct and widely occurring physiological state in focal epilepsies. This is true even outside the region of seizure initiation, indicating that it is possible to obtain predictive information from individual neuronal activity, without necessarily localizing what has been traditionally considered the seizure focus, and improving clinical care of patients with epilepsy by utilizing dynamics of ensembles of single neurons to predict seizures. The same analyses and procedures presented in Examples 1-21 can be applied to the prediction, prognosis, detection, diagnosis, neuromonitoring, management, and closed-loop prediction/detection and control of neurological events.

The mathematical and statistical procedures (methods, embodiments, analyses, procedures) are envisioned as further applicable to additional neurologic events, and even to other physiological conditions. For example, methods herein are suitable for diagnosis of a neurologic and/or psychiatric disease. The term, "disease" as used herein refers to a pathological condition that is different in time and duration from a neurological event, and the methods herein are appropriate to disease diagnosis. For example, methods herein are suitable to make a clinical prognosis regarding the speed, timing, and extent of recovery from a neurologic or psychiatric disease or event; to make a clinical prognosis regarding the likelihood of survival from disease or injury to the nervous system; to predict or detect the development and/or resolution of cerebral vasospasm and/or cerebral ischemia following neurological disease or injury which is an additional example of a neurological event; to provide real-time information indicating the benefit, lack of benefit, or harm of specific medical and/or surgical interventions for neurologic or psychiatric disease; and to provide indications of efficacy of pharmacotherapeutic interventions in animal research models of human neurological or psychiatric disease.

What is claimed is:

1. A method for treating epilepsy in a subject, the method comprising the steps of:
    applying to the subject a recording device with microelectrodes connected to a computer;
    recording from the recording device continuous electrical signals generated from single brain neurons or other brain cells of the subject,
    detecting the electrical signals generated from the single cells;
    measuring the spiking activity of at least one recorded single neuron or other cell:
    characterizing the measured spiking activity of each recorded single neuron or other single cell as a collection of individual neural point process sample paths;
    estimating, using the computer, a sample path probability distribution of a collection of sample paths of length T computed in time interval (t−T−W,t−T], for one or more neurons or cells, such that
        t is the current time, and
        W equals a time period extending into the past of specified duration
        such that W>T>0 the sample paths being overlapping or non-overlapping in time;
    determining, for one or more neurons or cells, whether the sample path measured in time interval (t−T,t] for the neuron or other cell falls outside a confidence interval of a current sample path distribution;
    assigning weight to a neuron based on importance or reliability of that neuron for the prediction or detection of the epileptic event;
    predicting or detecting the epileptic event
        by whether the measured sample path falls outside of the given confidence interval; or
        by whether a weighted sum of the neurons having sample paths computed on the interval (t−T,t] falls outside a confidence interval of a corresponding sample path probability distribution computed on the interval (t−T−W,t−T], and is above a threshold; and
    treating the subject according to the predicted or detected epileptic event.

2. The method according to claim 1 further comprising predicting or detecting the epileptic event by calculating a relative predictive power (RPP) within the time interval (t−T,t] in which:
    t is the current time; and
    T is sample path length, falling outside of a confidence interval threshold of a relative predictive power calculated within the time interval (t−T−W,t−T].

3. The method according to claim 2 wherein the relative predictive power ($RPP_i$) is calculated from an area under a curve for an ith neuron ($AUC_i$) or other cell according to the formula:

$$RPP_i=2(AUC_i-AUC_i^*),$$

wherein $AUC^*_i$ is an area under a receiver operating characteristic curve that corresponds to a chance level predictor for the ith neuron or other cell and model, estimated via random permutation methods.

4. The method according to claim 3, further comprising the steps of:
    fitting conditional intensity function models to each recorded neuron or other cell based on data collected during a first time interval, (t−T,t],
    fitting multiple conditional intensity function models to each recorded neuron or other cell based on data collected during overlapping or non-overlapping time windows from a second time interval (t−T−W, t−T];
    determining a relative predictive power for all of the recorded neurons or other cells during the first time interval under a cross-validation scheme;
    determining a probability distribution of relative predictive powers from each of the recorded neurons or other cells based on a plurality of RPPs computed from the multiple models fitted to data from the second time interval under a cross-validation scheme; and
    predicting or detecting the epileptic event by comparing the RPPs of at least a fraction of neurons or other cells, based on data from the interval (t−T, t], falling outside a confidence interval of the corresponding RPP probability distribution from the interval (t−T−W,t−T].

5. The method according to claim 4, wherein the time interval (t−T,t] is at least one window selected from a single window, overlapping windows, and non-overlapping windows.

6. The method according to claim 3, further comprising the steps of:
    fitting the conditional intensity function model to each recorded neuron or other cell based on data collected during a first time interval, (t−T,t],
    fitting multiple conditional intensity function models to each recorded neuron or other cell based on data collected during overlapping or non-overlapping time windows from a second time interval (t−T−W,t−T];

determining the relative predictive power for all of the recorded neurons or other cells during the first time interval;

determining a probability distribution of-relative predictive powers from each of the recorded neurons or other cells based on the RPPs computed from the multiple models fitted to data from the second time interval;

assigning weight to a neuron based on the importance or reliability of that neuron for predicting a epileptic event; and predicting or detecting the epileptic event by comparing the RPPs of the weighted sum of neurons, computed from data in (t−T, t] falling outside a confidence interval of their corresponding RPP probability distributions, above the threshold.

7. The method according to claim 3, further comprising the steps of:

fitting conditional intensity function models to each recorded neuron or other cell based on data collected during a first time interval, (t−T, t], fitting multiple conditional intensity function models to each recorded neuron or other cell based on data collected during overlapping or non-overlapping time windows from a second time interval(t−T−W,1−T];

determining a probability distribution of relative predictive powers computed under a cross-validation scheme from all of a plurality of the recorded neurons or other cells during the first time interval;

determining a probability distribution of relative predictive powers computed under a cross-validation scheme from all of the recorded neurons or other cells during the second time interval; and predicting or detecting the epileptic event by comparing whether statistical differences among the two probability distributions are above the threshold.

8. The method according to claim 3, further comprising the steps of:

fitting the point process models to each recorded neuron or other cell based on data collected during a current first time interval; (t−T, t] and a second time interval (t−T−W,t−T], where t is the current time and W is a specified amount of time greater than T; and, determining a probability distribution of relative predictive powers for all of a plurality of the recorded neurons or other cells during the first time interval;

determining a probability distribution of relative predictive powers for all of the recorded neurons or other cells during the second time interval, and predicting or detecting the epileptic event by comparing whether statistical differences among the two probability distributions are above the threshold.

9. A method for treating epilepsy in a subject, the method comprising the steps of:

applying to the subject a recording device with microelectrodes connected to a computer:

recording signals generated from single neurons or other cells in the brain of the subject: and detecting electrical signals generated from the single neurons or other cells;

measuring spiking activity with the device of at least one recorded single neuron or other cell, wherein the spiking activity of each neuron or other cell is represented as a spike train;

estimating a conditional intensity function model of the spike train for the at least one recorded neuron or other cell;

calculating, using the computer, a probability of the at least one recorded neuron or other cell spiking at a given time using the estimated conditional intensity function model;

computing a receiver operating characteristic curve for the at least one recorded neuron or other cell from its corresponding spike train and the calculated probability;

deriving a relative predictive power (RPP) measure from the receiver operating characteristic curve of the at least one recorded neuron or other cell, determining the epileptic event from the relative predictive power for the at least one recorded neuron or other cell; and treating the subject according to the epileptic event.

10. The method according to claim 9, further comprising after measuring spiking activity, fitting a history point process model to each recorded neuron or cell using the spike train.

11. The method according to claim 10 wherein the step of fitting a history point process model comprises using the following equation:

$$\log[\lambda_i(t \mid H_t)\Delta] = \mu_i + \sum_{k=1}^{p} K_{1,i,k} \cdot x_i + \sum_{j \neq i}^{C} \sum_{k=1}^{q} K_{2,i,j,k} \cdot x_j,$$

wherein t indexes discrete time, $\Delta$ a specified amount of time, and $\mu_i$, relates to a background level of spiking activity, $H_i$ is the spiking history up to, but not including, time t of all recorded neurons or other cells, $\lambda_i(t|H_i)$ is the conditional intensity function model of the ith neuron or cell conditioned on all of the recorded spiking histories, $x_i$ denotes the spiking history or spike train for the ith neuron or other cell, i=1, . . . , C, recorded neurons or other cells, $K_{1,i,k}$ and $K_{2,i,j,k}$ comprise temporal basis functions with coefficients that are estimated for intrinsic and ensemble history function respectively.

12. The method according to claim 11, further comprising choosing a temporal basis function.

13. The method according to claim 12, wherein the temporal basis function comprises a raised cosine function.

14. The method according to claim 9, further comprising after computing the receiver operating characteristic curve, measuring the area under the curve.

15. The method according to claim 9, wherein the probability is conditional on past spiking histories.

16. The method according to claim 9, the step of calculating the probability further comprises using the following equation:

$$Pr(x_{i,t}=1|H_t)=\lambda(t|H_t)\Delta+o(\Delta)\approx\lambda_i(t|H_t)\Delta$$

in which $X_{i,t} \in \{0,1\}$ denotes the state (0=no spike, 1=spike) of the ith neuron or cell at time t, $H_t$ is the spiking history up to and not including, time t of all recorded neurons or other cells, $\lambda_i(t|H_t)$ is the conditional intensity function model of the ith neuron or cell, conditioned on the recorded spiking histories, $\Delta$ is a bin size for a discretization of time, and $o(\Delta)$ relates to a probability of observing more than one spike in a specified time interval.

17. A method for treating epilepsy in a patient, the method comprising the steps of:

recording signals on a computer generated from a plurality of single neurons or other cells in the brain of the epileptic patient;
detecting electrical signals generated from the plurality of the single neurons or other cells;
measuring spiking activity of a corresponding plurality of recorded single neurons or other cells, wherein the spiking activity of each neuron or other cell is represented as a spike train;
estimating, using the computer, a conditional intensity function model of the spike train for each neuron or other cell,
deriving a graphical neuronal network connectivity model from estimated ensemble temporal filters in the conditional intensity functions for the set of recorded neurons or other cells during time interval (t−T,t], wherein:
t is the current time and
T>0,
determining a parameter from the graphical model;
predicting or detecting the epileptic event in the patient by comparing the parameter to a probability distribution of the same parameter determined during multiple windows in the time interval (t−T−W,t−T], wherein:
W>T and
occurrence of a epileptic event is predicted or detected from the comparison, and
treating the patient according to the predicted or detected epileptic event.

18. The method according to claim 17, wherein the parameter comprises graph density.

19. The method according to claim 18, wherein the graph density comprises dividing number of directed edges by total possible number of edges.

20. The method according to claim 18 wherein the method further comprises providing a diagnosis based on the prediction or detection.

21. The method according to claim 20, the method further comprising providing a prognosis based on the diagnosis.

22. A method for treating epilepsy in a subject, the method comprising the steps of:
recording signals generated from single brain neurons or other brain cells of the subject on a computer,
detecting electrical signals generated from the single neurons or other cells,
measuring spiking activity of at least one recorded single neuron or other cell;
measuring an electric field potential of at least one recorded single neuron or other cell;
estimating using the computer a pairwise spike-field spectral coherence between a spike train which is a representation of the spiking activity and the field potential at a given frequency f, for each pair of recorded neuron (or other cell) and field potential,
determining the spectral coherence according to $$C_{XY}(f) = \frac{S_{XY}(f)}{\sqrt{S_X(f)S_Y(f)}}$$

in which
X represents the spike train of a single neuron or cell from time interval (t−T,t],
Y represents the measured electric field potential at a recording microelectrode of a single neuron or cell from time interval (t−T−W,t−T],
t is the current time,
W>T>0, $S_{XY}(f)$ is cross-power at frequency f; and
$S_X(f)$ and $S_Y(f)$ correspond to autopower of X and Y at the frequency f, respectively;
computing a first and a second probability distribution of determined spike-field spectral coherences for each frequency, wherein:
the first probability distribution is current and is based on data collected during the time interval (1−T, t] and
the second probability distribution is based on at least one window from the time interval (t−T−W, t−T], in which:
t is current time, and
W equals a time period of specified duration that is greater than T,
predicting or detecting an epileptic event by comparing the first and the second probability distributions, and
treating the subject according to the predicted or detected epileptic event.

23. The method according to claim 22 wherein the electric field potential comprises multi-unit activity.

24. The method according to claim 22 wherein the second probability distribution is based on a single time window collected during the time interval (t−T−W,t−T].

25. The method according to claim 24 wherein the comparison comprises utilizing a statistical test.

26. The method according to claim 25, wherein the epileptic event is predicted or detected if the first and the second distributions are determined to be statistically different.

27. The method according to claim 26 wherein the statistical test comprises a two-sample Kolmogorov-Smirnov test.

28. The method according to claim 22 wherein the second probability distribution is based on a plurality of non-overlapping windows collected during the time interval (t−T−W,t−T].

29. The method according to claim 22, wherein a epileptic event is predicted or detected if a currently determined Spike-Field spectral coherence falls outside of a confidence interval of the second probability distribution.

* * * * *